US012702624B2

(12) United States Patent
Aon et al.

(10) Patent No.: US 12,702,624 B2
(45) Date of Patent: Aug. 11, 2026

(54) CONNECTED MEDICATION DISPENSER

(71) Applicant: NUCLEUSRX, INC., Martinsville, NJ (US)

(72) Inventors: Projit Aon, Martinsville, NJ (US); Ashok Rakhit, Warren, NJ (US); Yogesh Agarwal, Uttar Pradesh (IN); Dev Dutt, Uttar Pradesh (IN); Sai Rajendra Motamarri, Uttar Pradesh (IN)

(73) Assignee: NUCLEUSRX, INC., Martinsville, NJ (US)

(*) Notice: Subject to any disclaimer, the term of this patent is extended or adjusted under 35 U.S.C. 154(b) by 629 days.

(21) Appl. No.: 18/121,537

(22) Filed: Mar. 14, 2023

(65) Prior Publication Data

US 2023/0248614 A1 Aug. 10, 2023

Related U.S. Application Data

(63) Continuation-in-part of application No. 16/863,955, filed on Apr. 30, 2020, now Pat. No. 11,602,488.

(Continued)

(51) Int. Cl.

| | |
|---|---|
| ***A61J 7/04*** | (2006.01) |
| ***A61J 7/00*** | (2006.01) |
| ***G16H 20/13*** | (2018.01) |

(52) U.S. Cl.

CPC ........... *A61J 7/0418* (2015.05); *A61J 7/0076* (2013.01); *A61J 7/0436* (2015.05); *A61J 7/049* (2015.05);

(Continued)

(58) Field of Classification Search

CPC ...... A61J 7/0418; A61J 7/0076; A61J 7/0436; A61J 7/049; A61J 2200/30; A61J 2200/70; A61J 2200/72; A61J 2200/74; A61J 2205/00; A61J 2205/70; G16H 20/13; G16H 50/30; G16H 40/67; G06Q 10/08; G06Q 10/10; G06Q 30/015; G06Q 30/0185; G06Q 30/0281; G06Q 30/0607;

(Continued)

(56) References Cited

U.S. PATENT DOCUMENTS

| | | | |
|---|---|---|---|
| 5,642,731 | A | 7/1997 | Kehr |
| 5,812,410 | A | 9/1998 | Lion et al. |

(Continued)

*Primary Examiner* — Timothy R Waggoner

(74) *Attorney, Agent, or Firm* — Lisa E. Geary; Eckert Seamans Cherin & Mellott LLC

(57) ABSTRACT

Apparatus and associated software and methods for improving medication adherence. A connected medication dispenser includes a robotic arm adapted to deliver a prescribed medication dose to a patient in their home, and software and sensors that analyze the patient's compliance, communicate with external health sensors to monitor the patient's response to the dose, and communicate with external servers to send the result of providing the medication dose to the patient. In an illustrative example, the patient may be a chronic, acute, or terminal illness patient, and the results may be communicated with physicians, payers, caregivers, a pharmacy, and/or the patient's electronic health record. The flow of information may allow the physician or caregiver to offer real-time adjustments to the medication type, dose, and schedule to provide improved therapeutic outcomes.

26 Claims, 39 Drawing Sheets

Related U.S. Application Data

(60) Provisional application No. 62/841,211, filed on Apr. 30, 2019.

(52) U.S. Cl.
CPC .......... *G16H 20/13* (2018.01); *A61J 2200/30* (2013.01); *A61J 2200/70* (2013.01); *A61J 2200/72* (2013.01); *A61J 2200/74* (2013.01); *A61J 2205/00* (2013.01); *A61J 2205/70* (2013.01)

(58) Field of Classification Search
CPC .... G06Q 30/0613; G06Q 40/08; G06Q 50/22; G07F 17/0092
See application file for complete search history.

(56) References Cited

U.S. PATENT DOCUMENTS

| | | | | |
|---|---|---|---|---|
| 5,927,545 | A | 7/1999 | Pearson | |
| 6,256,967 | B1 | 7/2001 | Hebron et al. | |
| 6,471,087 | B1 | 10/2002 | Shusterman | |
| 6,717,598 | B1 | 4/2004 | Melton, Jr. et al. | |
| 7,122,005 | B2 | 10/2006 | Shusterman | |
| 7,530,211 | B2 | 5/2009 | McErlean et al. | |
| 7,828,147 | B2 | 11/2010 | Caracciolo et al. | |
| 8,061,109 | B2 | 11/2011 | Freudelsperger | |
| 8,600,548 | B2 | 12/2013 | Bossi et al. | |
| D733,454 | S | 7/2015 | Von Heifner et al. | |
| 9,073,206 | B2 | 7/2015 | Carson et al. | |
| 9,271,897 | B2 | 3/2016 | Costello et al. | |
| 9,358,499 | B2 | 6/2016 | Akdogan et al. | |
| 9,400,873 | B2 | 7/2016 | Kamen et al. | |
| 9,721,418 | B2 | 8/2017 | van Ooyen et al. | |
| 9,731,853 | B2 | 8/2017 | Akdogan et al. | |
| 10,025,908 | B1 | 7/2018 | Orellano et al. | |
| 10,179,411 | B2 | 1/2019 | Lessing et al. | |
| 10,246,207 | B2 | 4/2019 | Holmes | |
| 10,282,521 | B2 | 5/2019 | Hanson et al. | |
| 10,297,032 | B2 | 5/2019 | Hanina et al. | |
| 10,360,751 | B2 | 7/2019 | Berg et al. | |
| 10,993,881 | B1 * | 5/2021 | Karpman | A61J 7/0481 |
| 11,602,488 | B2 * | 3/2023 | Aon | G16H 15/00 |
| 2002/0104848 | A1 | 8/2002 | Burrows et al. | |
| 2007/0185615 | A1 | 8/2007 | Bossi et al. | |
| 2009/0299522 | A1 | 12/2009 | Savir et al. | |
| 2010/0121315 | A1 | 5/2010 | Trovato et al. | |
| 2010/0256808 | A1 | 10/2010 | Hui | |
| 2011/0201421 | A1 | 8/2011 | De Oliveira et al. | |
| 2016/0042151 | A1 * | 2/2016 | Akdogan | B25J 19/023 700/240 |
| 2016/0117484 | A1 | 4/2016 | Hanina et al. | |
| 2016/0136054 | A1 * | 5/2016 | Bunker | A61J 7/0084 340/573.1 |
| 2016/0162660 | A1 | 6/2016 | Strong | |
| 2017/0020785 | A1 | 1/2017 | McCullough | |
| 2017/0132867 | A1 * | 5/2017 | Berg | A61J 7/0481 |
| 2018/0110441 | A1 | 4/2018 | Frank et al. | |
| 2019/0027238 | A1 | 1/2019 | Hanina et al. | |
| 2019/0139640 | A1 | 5/2019 | Kamen et al. | |
| 2019/0205716 | A1 | 7/2019 | Moshkovitz et al. | |
| 2019/0322469 | A1 | 10/2019 | Haehnel et al. | |

* cited by examiner 1400
1425
1425
180
175
1605
185
1605
1425

1400
1425
180
175
1605
185
1605
1425

1400
1425
180
175
1605
1425
1605
185
1605

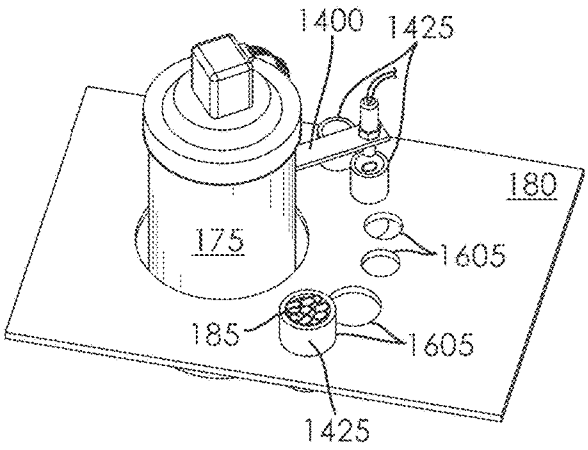
FIG. 23J
FIG. 23K
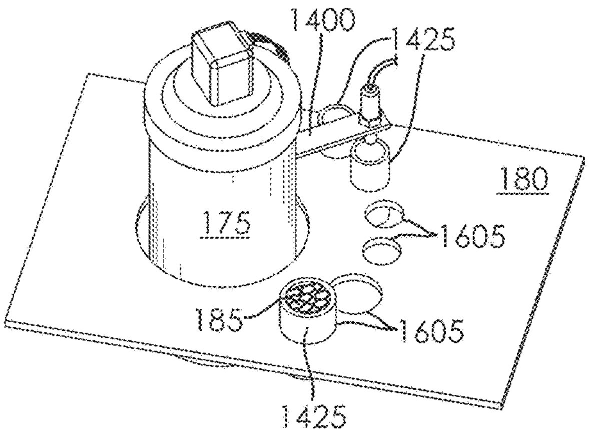
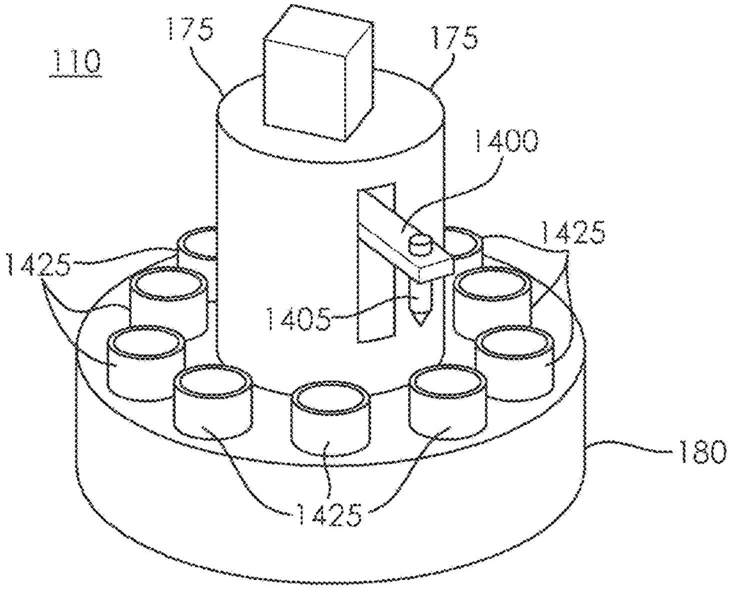
FIG. 24

CONNECTED MEDICATION DISPENSER

CROSS-REFERENCE TO RELATED APPLICATIONS

This application is a continuation-in-part of U.S. patent application Ser. No. 16/863,955, filed on Apr. 30, 2020, now U.S. Pat. No. 11,602,488, which claims the benefit of U.S. Provisional Application No. 62/841,211, titled "Connected Pill Dispenser," filed on Apr. 30, 2019. This application incorporates the entire contents of the above-referenced applications herein by reference.

TECHNICAL FIELD

Various embodiments relate to chronic, acute, seasonal, or terminal illness patient medication adherence, and systems and software methods that facilitate the medication adherence.

BACKGROUND

A chronic illness is an illness that is long-lasting. An acute illness is an illness that may be severe. A patient afflicted with an acute or chronic illness may not find a cure for the condition, even though they are treated by a physician or hospital. Some patients may receive medical treatment including medication prescribed by a physician to relieve symptoms or prevent the illness from getting worse. Some patients may need acute or limited time treatment care after release from hospital inpatient treatment, such as while the patient is still recovering.

Treatment of some illnesses may require timely adherence to multiple therapies on a given day, or drugs that require critical adherence to time of medicine intake because of a narrow therapeutic window to improve efficacy or avoid toxicity. Some patients may experience loss of short-term memory (for example, forgetfulness in early dementia, in an elderly or Alzheimer patient), or physically debilitating conditions, and hence, may be dependent on homecare without the benefit of expensive daily licensed nursing services.

Some medications used to treat chronic or acute illness may be expensive. The therapeutic effect of some medications prescribed to treat a patient's chronic or acute illness may be limited by the patient's adherence to the dosing protocol prescribed by the patient's physician. Elderly Patients simply taking multiple drugs or patients with debilitating mental or physical illness (for example, diseases like Alzheimer's, Parkinson's, dementia, or multiple sclerosis) may not remember or be physically able to take drugs on time from multiple bottles traditionally dispensed by pharmacies.

In various examples, a patient's adherence to the dosing protocol prescribed by the patient's physician may be a crucial component of caring for the patient's illness. Lack of adequate medication adherence may result in preventable disease progression and unnecessary cost to payers.

SUMMARY

Software, devices, and the associated methods disclosed herein relate to a connected medication dispenser configured to provide medication(s) needed to treat a patient's illness. The connected medication dispenser includes novel designs for at least a carousel that holds medication or object bins and is configured for bi-directional rotation, a weighing station configured to weight the object bins without removal from the carousel, and a robotic arm adapted to pick items from the item bins and deliver the items, e.g., a prescribed medication dose to a dispensing cup for patient retrieval. The connected medication dispenser may be utilized in the patient's home to deliver the medication(s) at selected times of the day and/or week; analyze the patient's response to the dose based on various sensor inputs; automatically determine whether the patient took the medicine; and provide caregivers with patient compliance data on intake of medication as well as response data from sensor inputs (e.g., example, blood pressure, heart rate, blood sugar level, etc.), such as may be suggested by the prescribing physician or remote caregiver.

In an illustrative example, the patient may be a chronic illness patient, an acute illness patient, or a patient needing short term treatment during home care for any illness. The medication dose may be, for example, medications prescribed by a physician or remote caregiver to be taken a specific number at specific times, e.g., throughout a day and/or week. In some embodiments, the connected medication dispenser may automatically notify the patient when a medication dose is due. Various embodiments of the connected medication dispenser may determine if the patient consumed a medication dose based on machine vision, audio, or other sensor data, permitting caregiver notification of patient medication adherence, medication compliance, or non-adherence. Various methods may advantageously direct the medication adherence, compliance, or non-adherence information to providers (for example, pharmacists, physicians, remote caregiver) and payers (for example, insurance companies, or Centers for Medicare and Medicaid services), in addition to directing this information to caregivers.

Various embodiments may achieve one or more advantages. For example, some embodiments may improve a patient's medication adherence. This facilitation may be a result of a system configured to encourage a patient to take the right medication in the right amount at the right time. In some embodiments, a patient's disease treatment outcome may be improved. Such improved treatment outcomes may be a result of more consistent medication dosing provided by a system configured to deliver the prescribed medication to the patient at the time the medication is to be consumed. Some embodiments may reduce the time required for a physician or remote caregiver to adjust dosage levels. Such reduced dosage adjustment time may be a result of connecting medication prescribers to real-time patient medication adherence data. In some embodiments, caregivers may be automatically notified of missed doses, permitting rapid caregiver intervention in critical illness care. Such automatic caregiver notification of missed doses may reduce a patient's exposure to undesirable effects due to inconsistent dosing.

Various embodiments may provide physicians and remote caregivers with a real-time patient physical parameter response monitoring capability, permitting a patient to remain at home while receiving care for an acute or chronic illness, or even care during terminal illness. Exemplary real-time patient physical parameter response monitoring capability may include measurement and reporting of patient blood pressure, blood oxygen, heart rate, blood sugar level, calorie consumption, and/or body temperature, or other home health monitoring parameters medically advisable or prescribed by a physician or remote caregiver. Various embodiments may provide remote care providers with cumulative data on patient physical parameters such as daily activity levels, daily or weekly body weight, daily sleep duration and patterns, or other home health monitoring parameters medically advisable or prescribed by a physician or remote caregiver.

In some embodiments, the effort required to adjust a patient's medication may be reduced, hence reducing drug cost, reducing adverse health events, or even optimizing overall treatment outcomes. Such treatment optimization may use real-time data collected by the connected medication dispenser disclosed herein and/or patient sensors and is the result of the novel software and configuration of the connected medication dispenser to deliver customized dosages of various medications retained in a variable-access dispensing tray. The connected medication dispenser may send patient treatment adherence and associated patient response data to a physician, remote caregiver, or pharmacist in time for the next visit, or in real-time as indicated hereinabove.

Some embodiments may provide a physician or remote caregiver with the capability to adjust doses remotely as per the patient's condition, in the event dynamic or immediate intervention is medically indicated, such as a change in a dose amount, dose administration timing, or even treatment interruption if medically necessary. In various embodiments, a physician's or remote caregiver's application (mobile or via a web portal) may have the capability to set patient-specific physical parameter thresholds to be notified or alerted automatically.

Some embodiments may reduce a pharmacy's inventory cost. This facilitation may be a result of a connected medication dispenser capable of managing medication counts and generating alerts for the pharmacy to replenish the medication for the patient on time.

The details of various embodiments are set forth in the accompanying drawings and the description below. Other features and advantages will be apparent from the description and drawings, and from the claims.

BRIEF DESCRIPTION OF THE DRAWINGS

Aspects, features, benefits, and advantages of the embodiments disclosed herein will be apparent with regard to the following description, appended claims, and accompanying drawings. In the following figures, like numerals represent like features in the various views. It is to be noted that features and components in these drawings, illustrating the views of various embodiments of the present invention, unless stated to be otherwise, are not necessarily drawn to scale.

FIGS. 23A-23K together depict operational top perspective views of an exemplary connected medication dispenser robotic arm according to the aspects of the present disclosure, wherein the robotic arm is shown dispensing a medication dose, based on gripping the medication retained by an embodiment medication container and releasing the dose into an exemplary dispensing chute.

FIG. 24 depicts a top perspective view of an exemplary center core robotic arm design according to the aspects of the present disclosure.

FIGS. 37A and 37B depict an exemplary connected medication dispenser according to aspects of the present disclosure, wherein FIG. 37B shows the outer housing of the connected medication dispenser as transparent to depict internal components.

FIGS. 38A and 38B depict an exemplary object bin according to aspects of the present disclosure for use in the connected medication dispenser shown in FIG. 37A, wherein FIG. 38A shows the object bin in the closed state and FIG. 38B shows the object bin in the open state.

FIGS. 39A and 39B depict an exemplary portable connected medication dispenser according to aspects of the present disclosure, wherein FIG. 39B shows the outer housing of the portable connected medication dispenser as transparent to depict internal components.

DETAILED DESCRIPTION

Figure 1:
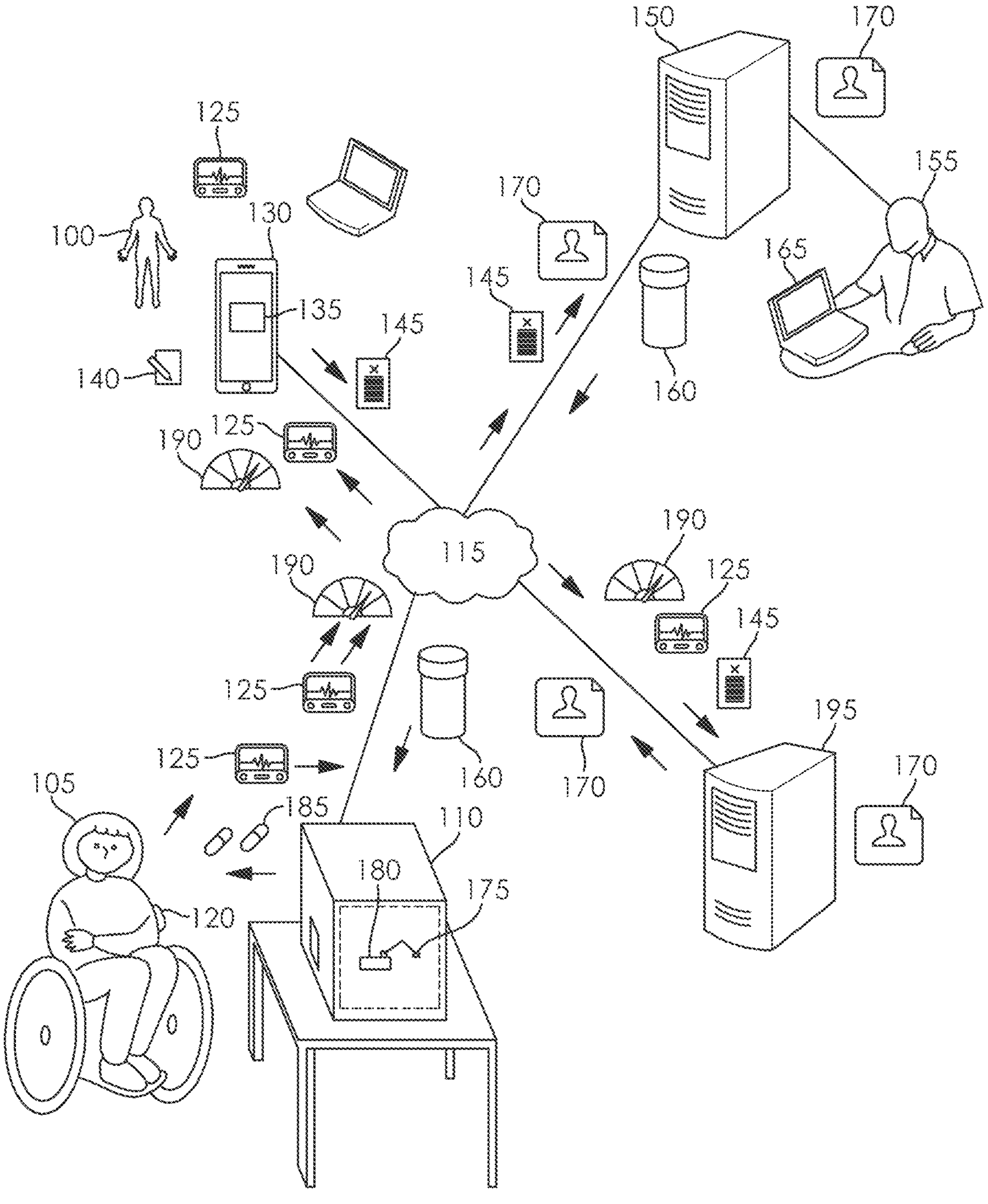
FIG. 1 depicts an illustrative operational scenario of the software, connected devices, and methods for improving patient therapeutic outcomes according to embodiments of the present disclosure, wherein a physician or remote caregiver treats an illness of a patient using an exemplary connected medication dispenser configured to provide medication(s) needed to treat a patient's illness, wherein the connected medication dispenser delivers a prescribed medication dose to a patient in their home, analyzes the patient's response to the dose based on various sensor inputs, automatically detects with high predictability whether the patient took the medicine, and provides caregivers the result of providing the medication dose to the patient, including a summary of the compliance data.

To aid understanding, this document is organized as follows: First, illustrative usage of an exemplary connected medication dispenser and associated software configured to improve a patient's medication adherence is briefly introduced with reference to FIG. 1. Embodiment design examples illustrating hardware, information infrastructure, and networks configured to improve a patient's medication adherence are described with reference to FIGS. 2-16. Finally, with reference to FIGS. 17A-39B, various embodiment connected medication dispensers and component designs are presented to explain improvements in medication adherence technology.

The devices, software program products, systems, and methods of the present disclosure enable improved patient medication adherence, and thus improved therapeutic outcomes, reduced time required for a physician or caregiver to adjust a dosage level, and automatic notification of missed doses to caregivers that permit rapid caregiver intervention in critical illness care.

As used herein, the term "caregiver" may be understood to mean a patient's personal caregiver, such as a relative or friend tasked with helping the patient, or an in-home non-prescribing health care assistant who lives with the patient or visits the patient daily or weekly. In certain instances, such a caregiver may be referred to as a local caregiver.

The term "caregiver" may also be understood to encompass a remote healthcare provider capable of diagnosing, treating, or prescribing medication for a patient, such as a physician or remote care team (e.g., nurses, physician's assistants, physical therapists, respiratory therapists, and the like), while the patient is at home or while the patient is in a hospital, rehabilitation center, nursing home, or the like. Such a caregiver may be referred to as a remote caregiver.

Thus, reference to a physician may also include reference to a prescribing remote caregiver.

Unless specifically defined, use of the term caregiver is inclusive of either a local caregiver or remote caregiver, or both.

The software, devices, and associated methods disclosed herein relate to a connected medication dispenser configured to provide medication(s) needed to treat a patient's illness. The connected medication dispenser includes novel designs for internal components, such as a carousel that holds medication or object bins and is configured for bi-directional rotation, a weighing station configured to weight the object bins without removal from the carousel, and a robotic arm adapted to pick items from the item bins and deliver the items, e.g., a prescribed medication dose to a dispensing cup for patient retrieval. The connected medication dispenser may be utilized in the patient's home to deliver the one or more medications at selected times and/or days. The connected medication dispenser may be part of a system that includes a software program product configured to provide communication amongst two or more of the patient, the connected medication dispenser, physician, pharmacy, caregiver, patient's electronic health record, patient worn health sensor, payer (e.g., insurance provider), and the like.

Accordingly, the presently disclosed invention may take the form of an entirely hardware embodiment, an entirely software embodiment (including firmware, resident software, micro-code, etc.), or an embodiment combining software and hardware aspects that may all generally be referred to herein as a "system". Furthermore, the presently disclosed invention may take the form of a computer program product embodied in any tangible medium of expression having computer useable program code embodied in the medium.

Operational Overview of the Systems and Devices for Improved Patient Medication Adherence An illustrative operational scenario is shown in FIG. 1 wherein a physician or remote caregiver treats an illness of a patient using an exemplary connected medication dispenser and software program product configured to improve medication adherence. The connected medication dispenser and software program product enable delivery of a prescribed medication dose to a patient in their home, analysis of the patient's response to the dose based on various sensor inputs (i.e., patient worn sensors, sensors on certain medical devices used by the patient, and/or sensors on the connected medication dispenser), automatic detection with high predictability of patient medication compliance (i.e., whether the patient took the medicine), and provides remote caregivers the results of providing the medication dose to the patient, including a summary of the compliance data.

In FIG. 1, the physician or remote caregiver 100 treats the patient 105 using the exemplary connected medication dispenser 110 via the network cloud 115. The patient 105 may employ a wearable device 120 configured with sensors adapted to measure patient physical parameters 125. In the depicted embodiment, the wearable device 120 is communicatively and operably coupled with the network cloud 115 and sends the measured patient physical parameters 125 to the physician's or remote caregiver's mobile device 130 via the network cloud 115. The measured patient physical parameters 125 may also be sent to the physician's or remote caregiver's web application accessed by a desktop computer. Moreover, the measured patient physical parameters 125 may also be collected at a central server 195. In the depicted embodiment, the mobile device 130 is configured with a mobile app ("mobile app") 135 adapted to assist the physician or remote caregiver 100 in treatment of the patient 105.

In the illustrated embodiment, the physician or remote caregiver 100 diagnoses the illness of the patient 105 and determines a prescription protocol 140 to treat the patient 105 illness. The mobile app 135 of the mobile device 130 creates a prescription 145, based on the prescription protocol 140 determined by the physician or remote caregiver 100. Alternatively, the prescription 145 may be created/sent by the physician's or remote caregiver's web portal.

With continued reference to FIG. 1, the mobile app 135 may send the prescription 145 to a pharmacy server 150 that is communicatively and operably coupled with the network cloud 115. A pharmacist 155 may issue an authorized prescription 160 using a pharmacy web portal 165 and/or pharmacy mobile app. In the depicted embodiment, the prescription 160 is authorized based on patient treatment profile data 170. In various embodiments, the patient treatment profile data 170 may include medications or treatments that a payer has authorized for the patient 105. As such, the pharmacy server 150 sends the authorized prescription 160 to the connected medication dispenser 110.

In the depicted embodiment shown in FIG. 1, a robotic arm 175 of the connected medication dispenser 110 locates and picks the authorized prescription 160 medication from a dispensing tray 180 or carousel. In the illustrated embodiment, the robotic arm 175 of the connected medication dispenser 110 delivers a prescription medication dose 185 to the patient 105. Further, the connected medication dispenser 110 collaborates with the patient wearable device 120 to determine if the patient 105 consumed the prescription medication dose 185. In various examples, the connected medication dispenser 110 and wearable device 120 may determine if the patient consumed the medication dose 185 based on sensor input, including, for example, image analysis, audio analysis, motion detection, by asking the patient 105 and recording the patient 105 answer, or by measuring patient 105 biological response to the prescription medication dose 185. In various embodiment implementations, several distinct activities may be measured to determine compliance/adherence. For example, upon receiving a dose reminder, the patient or authorized caregiver may identify himself/herself using the biometric sensors on the device to begin the dispense action. An image/video/motion or voice analysis can be performed by the device, correlated with the dispense event to determine a higher degree of compliance. Additionally, or alternatively, a biological response collected by the patient wearable device 120 may be correlated with the dispense or the intake event to determine a higher degree of compliance.

In the illustrated embodiment of FIG. 1, the connected medication dispenser 110 determines a medication adherence score 190 to represent the probability the patient 105 consumed the medication dose 185, based on sensor input. In the depicted embodiment, the connected medication dispenser 110 sends the medication adherence score 190 and related adherence information to the central server 195 via the network cloud 115, which distributes the information to parties that are interested in such information, which may include, for example, the physician's or remote caregiver's mobile app 135, a web portal providing authorized access to a web application, a pharmacy server 150, or the payer's server (insurer's server, also referred to herein as a payer management server, which may include the patient's electronic health record). In the illustrated embodiment, the physician's or remote caregiver's 100 mobile app 135 sends the medication adherence score 190, the measured patient physical parameters 125, and the prescription 145, to the payer management server 195. In the depicted embodiment, the central server 195 updates the patient treatment profile data 170 based on the real-time medication adherence score 190, the measured patient physical parameters 125, and the prescription 145. Of note, this same flow of information may also be directed to the payer management server, which would mimic the flow shown for the central server 195. Thus, the physician's or remote caregiver's 100 mobile app 135 may additionally or alternatively send the medication adherence score 190, the measured patient physical parameters 125, and the prescription 145, to the payer management server, wherein the payer management server updates the patient treatment profile data 170 based on the received data.

Figure 2:
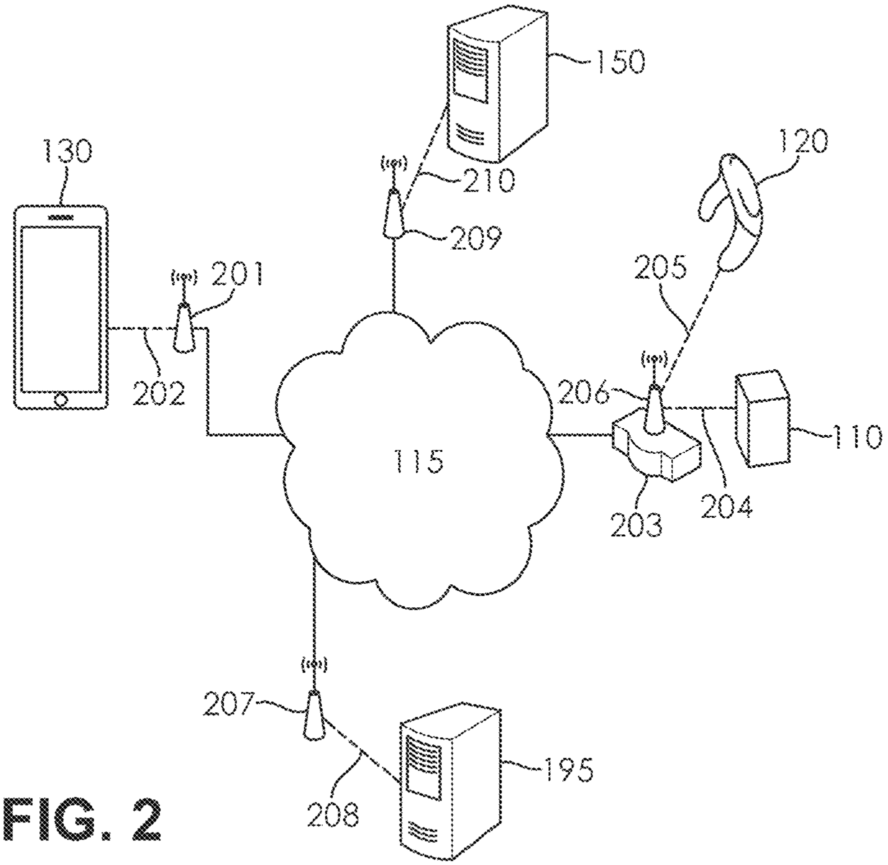
FIG. 2 depicts a schematic view of an exemplary medication adherence network according to aspects of the present disclosure configured to automatically determine whether a patient took a prescribed medicine dose provided by an embodiment connected medication dispenser.

FIG. 2 depicts a schematic view of an exemplary medication adherence network configured to automatically determine whether a patient took a prescribed medicine dose provided by any of the various embodiments of the connected medication dispenser disclosed herein. For example, according to an exemplary embodiment of the present disclosure, data may be transferred to the system, stored by the system and/or transferred by the system to users of the system across local area networks (LANs), wide area networks (WANs), or Wireless WAN (WWAN), such as, for example, cellular networks. In accordance with various embodiments, the system may include numerous servers, data mining hardware, computing devices, or any combination thereof, communicatively connected across one or more LAN, WAN, or WWAN. One of ordinary skill in the art would appreciate that there are numerous manners in which the system could be configured, and embodiments of the present disclosure are contemplated for use with any configuration.

With continued reference to FIG. 2, a schematic overview of a system in accordance with an embodiment of the present disclosure is shown. In the depicted embodiment, an exemplary system includes a connected medication dispenser 110 configured to improve the patient's medication adherence. In the illustrated embodiment, the connected medication dispenser 110 includes a computing device and network interface enabling communication 204 via the cloud 115; the wearable device 120 includes a computing device with sensors adapted to measure patient physical parameters; the mobile device 130 is a smartphone; and the pharmacy server 150 is a computing device configured to host and manage data. In the depicted example, the server 195 is a computing device configured to host and manage data. For example, the server 195 may be the central server that collects information from the connected medication dispenser 110, or prescription from the customer (i.e., patient) and/or prescription configuration from the pharmacists, and feeds information to various parties as and when needed.

In various scenarios, the central server 195 may be configured to perform a payer management function, in addition to other functions. The server 195 could be implemented on a public, private, or hybrid cloud infrastructure. Further, the mobile device 130 is communicatively and operably coupled by a wireless access point 201 and wireless link 202 with the network cloud 115 (for example, the Internet) to send, retrieve, and/or manipulate information in storage devices, servers, and network components, and exchange information with various other systems and devices via the network cloud 115. In the depicted example, the illustrative system includes a router 203 configured to communicatively and operably couple the connected medication dispenser 110 to the network cloud 115 via a communication link 204 and wireless access point 206. In the illustrated example, the router 203 also communicatively and operably couples the wearable device 120 to the network cloud 115 via a communication link 205 and wireless access point 206. Further, the payer 195, i.e., payer management server, may be communicatively and operably coupled with the network cloud 115 by a wireless access point 207 and a wireless communication link 208.

In the embodiment illustrated in FIG. 2, the pharmacy server 150 is communicatively and operably coupled with the network cloud 115 by a wireless access point 209 and a wireless communication link 210. In various examples, one or more of: the connected medication dispenser 110, wearable device 120, mobile device 130, pharmacy, remote caregiver, or physician server 150, or central cloud server or payer management server 195 may include an application server configured to store or provide access to information used by the system. In various embodiments, one or more application servers 150 may retrieve or manipulate information in storage devices and exchange information through the network cloud 115. In some examples, one or more of: the connected medication dispenser 110, wearable device 120, mobile device 130, pharmacy, remote caregiver, or physician server 150, or central could server or payer management server 195 may include various applications implemented as processor-executable program instructions. Various processor-executable program instruction applications may also be used to manipulate information stored remotely and process and analyze data stored remotely across the network cloud 115 (for example, the Internet).

According to an exemplary embodiment, as shown in FIG. 2, exchange of information through the network cloud 115 or other network may occur through one or more high speed connections. In some cases, high speed connections may be over-the-air (OTA), passed through networked systems, directly connected to one or more network cloud 115, or directed through one or more routers. In various implementations, one or more routers may be optional, and other embodiments in accordance with the present disclosure may or may not utilize one or more routers. One of ordinary skill in the art would appreciate that there are numerous ways any or all of the depicted devices may connect with the network cloud 115 for the exchange of information, and embodiments of the present disclosure are contemplated for use with any method for connecting to networks for the purpose of exchanging information. Further, while this application may refer to high speed connections, embodiments of the present disclosure may be utilized with connections of any useful speed.

In an illustrative example, components or modules of the system may connect to one or more of: the connected medication dispenser 110, wearable device 120, mobile device 130, pharmacy server 150, payer management server 195, or the web portal 165 (depicted in FIG. 1, representing the physician's or remote caregiver's office, pharmacy, or the payer) via the network cloud 115 or other network in numerous ways. For instance, a component or module may connect to the system i) through a computing device directly connected to the network cloud 115, ii) through a computing device connected to the network cloud 115 through a routing device, or iii) through a computing device connected to a wireless access point. One of ordinary skill in the art will appreciate that there are numerous ways that a component or module may connect to a device via network cloud 115 or other network, and embodiments of the present disclosure are contemplated for use with any network connection method.

In various examples, one or more of: the connected medication dispenser 110, wearable device 120, mobile device 130, pharmacy, remote caregiver, or physician server 150, or central cloud server or payer management server 195 could include a personal computing device, such as a smartphone, tablet computer, wearable computing device, cloud-based computing device, virtual computing device, or desktop computing device, configured to operate as a host for other computing devices to connect to. In some examples, one or more communications means of the system may be any circuitry or other means for communicating data over one or more networks or to one or more peripheral devices attached to the system, or to a system module or component. Appropriate communications means may include, but are not limited to, wireless connections, wired connections, cellular connections, data port connections, Bluetooth® connections, near field communications (NFC) connections, or any combination thereof. One of ordinary skill in the art will appreciate that there are numerous communications means that may be utilized with embodiments of the present disclosure, and embodiments of the present disclosure are contemplated for use with any communications means.

Figure 3:
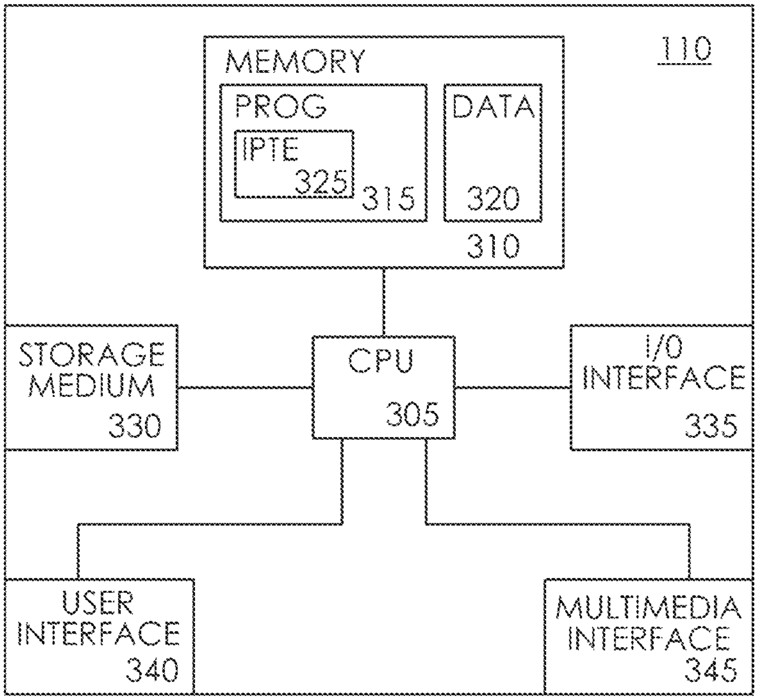
FIG. 3 depicts a structural view of an exemplary connected medication dispenser according to aspects of the present disclosure configured to improve a patient's medication adherence.

FIG. 3 depicts a structural view of an exemplary connected medication dispenser configured to improve a patient's medication adherence. In FIG. 3, the block diagram of the exemplary connected medication dispenser 110 includes a processor 305 and a memory 310. The processor 305 is in electrical communication with the memory 310. The depicted memory 310 includes program memory 315 and data memory 320. The depicted program memory 315 includes processor-executable program instructions implementing the IPTE (Interactive Patient Treatment Engine) 325. In some embodiments, the IPTE 325 may be upgradeable remotely via over-the-air (OTA) methods, or locally using methods such as Bluetooth connection with a mobile device, a thumb drive using a USB port, or via a wired connection for manual upgrade.

In some embodiments, the illustrated program memory 315 of FIG. 3 may include processor-executable program instructions configured to implement an OS (Operating System). In various embodiments, the OS may include processor executable program instructions configured to implement various operations when executed by the processor 305. In some embodiments, the OS may be omitted.

In some embodiments, the illustrated program memory 315 may include processor executable program instructions configured to implement various Application Software. In various embodiments, the application software may be upgradeable remotely via over-the-air (OTA) methods, or locally using methods such as Bluetooth connection with a mobile device, a thumb drive using USB port, or by a wired connection for manual upgrade. In various embodiments, the application software may include processor executable program instructions configured to implement various operations when executed by the processor 305. In some embodiments, the application software may be omitted. In the depicted embodiment, the processor 305 is communicatively and operably coupled with a storage medium 330. In the depicted embodiment, the processor 305 is communicatively and operably coupled with an I/O (Input/Output) interface 335. In the depicted embodiment, the I/O interface 335 includes a network interface. In various implementations, the network interface may be a wireless network interface, a Wi-Fi interface, a Bluetooth interface, or a cellular WAN (WWAN) interface. In an illustrative example, the connected medication dispenser 110 may include more than one network interface. In some designs, the network interface may be a wireline interface. In some designs, the network interface may be omitted.

In the depicted embodiment of FIG. 3, the processor 305 is communicatively and operably coupled with a user interface 340. In various implementations, the user interface 340 may be adapted to receive input from a user or send output to a user. The user interface 340 may be adapted to an input-only or output-only user interface mode. The user interface 340 may include an imaging display and/or an audio interface. For example, the audio interface may include an audio input and/or an audio output. In some implementations, the user interface 340 may be touch-sensitive.

In some embodiments, the user interface 340 may include an input sensor array. In various implementations, the input sensor array may include one or more imaging sensors, one or more audio transducers, a radio-frequency detector, and/or an ultrasonic audio transducer. In some embodiments, the input sensor array may include image sensing subsystems or modules configurable by the processor 305 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection. In some embodiments, the input sensor array may include audio sensing subsystems or modules configurable by the processor 305 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection.

In various embodiments, the connected medication dispenser 110 may include an accelerometer operably coupled with the processor 305, a GPS module operably coupled with the processor 305, and/or a magnetometer operably coupled with the processor 305.

In various implementations, the depicted memory 310 may contain processor executable program instruction modules configurable by the processor 305 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection. In various implementations, the depicted memory 310 may contain processor executable program instruction modules configurable by the processor 305 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection.

In the depicted embodiment, the processor 305 is communicatively and operably coupled with a multimedia interface 345, which may include interfaces adapted for input and output of audio, video, and image data. In some embodiments, the multimedia interface 345 may include one or more still image camera or video camera, and one or more microphone. In some implementations, the multimedia interface 345 may include a wireless communication means configured to operably and communicatively couple the multimedia interface 345 with a multimedia data source or sink external to the connected medication dispenser 110. In assorted designs, the multimedia interface 345 may include interfaces adapted to send, receive, or process encoded audio or video; one or more video, image, or audio encoders; and/or one or more video, image, or audio decoders. In various implementations, the multimedia interface 345 may include interfaces adapted to send, receive, or process one or more multimedia stream. In various implementations, the multimedia interface 345 may include a GPU. In some embodiments, the multimedia interface 345 may be omitted.

Useful examples of the computing devices of the illustrated connected medication dispenser 110, and or computing devices they which the connected medication dispenser 110 may communicate include, but are not limited to, personal computers, servers, tablet PCs, smartphones, or other computing devices. In some embodiments, multiple connected medication dispenser 110 devices may be operably linked to form a computer network in a manner as to distribute and share one or more resources, such as clustered computing devices and server banks/farms. Numerous examples of such general-purpose multi-unit computer networks suitable for embodiments of the disclosure, their typical configuration and many standardized communication links are well known to one skilled in the art, as explained in more detail in the foregoing FIG. 2 description.

In some embodiments, an exemplary connected medication dispenser 110 design may be realized in a distributed implementation. In an illustrative example, some connected medication dispenser 110 designs may be partitioned between a client device, such as, for example, a phone, and a more powerful server system, as depicted, for example, in FIG. 2. In distinct designs, a connected medication dispenser 110 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work. In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary connected medication dispenser 110 may be configured to operate on a device with less processing power, such as, for example, various gaming consoles, which may not have sufficient processor power, or a suitable CPU architecture, to adequately support the connected medication dispenser 110. Various embodiment designs configured to operate on a such a device with reduced processor power may work in conjunction with a more powerful server system.

Figure 4:
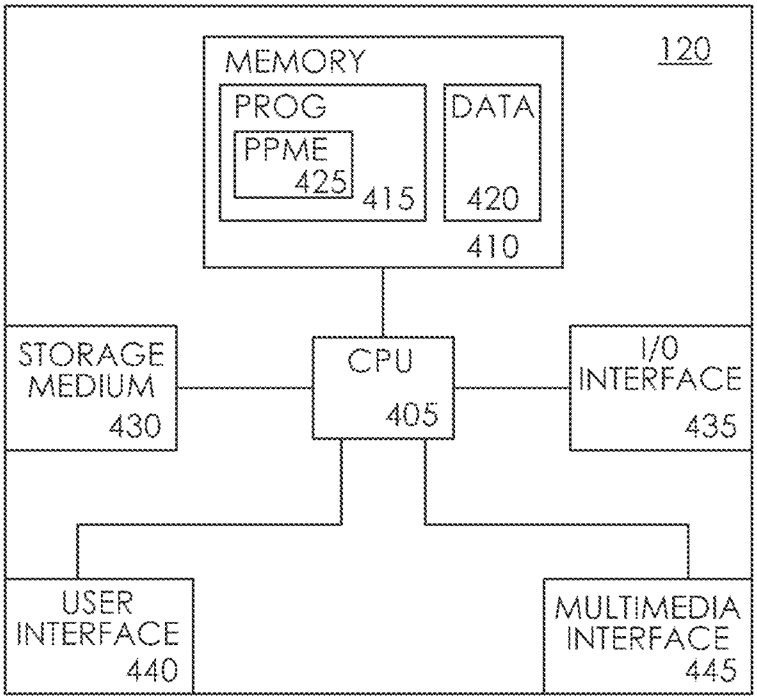
FIG. 4 depicts a structural view of an exemplary patient-wearable computing device configured to provide patient physical parameter data to various connected devices according to aspects of the present disclosure.

FIG. 4 depicts a structural view of an exemplary patient-wearable computing device 120 configured to improve a patient's medication adherence. In FIG. 4, the block diagram of the exemplary wearable device 120 includes a processor 405 and a memory 410. The processor 405 is in electrical communication with the memory 410. The depicted memory 410 includes program memory 415 and data memory 420. The depicted program memory 415 includes processor-executable program instructions implementing the PPME (Patient Parameter Monitoring Engine) 425. In some embodiments, the PPME 425 may be upgradeable remotely via over-the-air (OTA) methods, or locally using methods such as Bluetooth connection with a mobile device, a thumb drive using a USB port, or by a wired connection for manual upgrade.

In some embodiments, the illustrated program memory 415 may include processor-executable program instructions configured to implement an OS (Operating System). In various embodiments, the OS may include processor executable program instructions configured to implement various operations when executed by the processor 405. In some embodiments, the OS may be omitted.

In some embodiments, the illustrated program memory 415 may include processor-executable program instructions configured to implement various Application Software. In various embodiments, the application software may be upgradeable remotely via over-the-air (OTA) methods, or locally using methods such as Bluetooth connection with a mobile device, a thumb drive using USB port, or by a wired connection for manual upgrade. In various embodiments, the application software may include processor executable program instructions configured to implement various operations when executed by the processor 405. In some embodiments, the application software may be omitted.

In the depicted embodiment, the processor 405 is communicatively and operably coupled with the storage medium 430. In the depicted embodiment, the processor 405 is communicatively and operably coupled with the I/O (Input/Output) interface 435. In the depicted embodiment, the I/O interface 435 includes a network interface. In assorted designs, the I/O interface may include input and/or output configured to operably govern and communicate with patient parameter sensors communicatively coupled with the wearable device. Exemplary patient parameter sensors may monitor any one or more of blood pressure, blood sugar level, blood oxygen level, heart rate, and/or body temperature, or other home health monitoring parameters medically advisable or prescribed by a physician or remote caregiver.

Additional monitoring is possible using the systems, software, and connected medication dispensers disclosed herein. For example, at home devices also exist for measuring body weight (e.g., scale); monitoring lung congestion, such as via thoracic impedance or tissue dielectric sensors (e.g., ReDS™ vest); monitoring hemodynamics, such as via pulmonary artery pressure (e.g., CardioMEMS™) or left atrial pressure monitoring; and defibrillators or cardiac resynchronization therapy (CRT). Data from each of these worn or used devices may be communicated from the device via the internet, i.e., internet capable devices), or may be entered manually by the patient or a caregiver. In preferred embodiments, the word and/or used health monitoring devices are internet enables.

Various embodiments may provide remote caregivers with cumulative data on patient physical parameters such as daily activity levels, daily or weekly body weight, daily sleep duration and patterns, or other home health monitoring parameters medically advisable or prescribed by a physician or remote caregiver.

In various implementations, the network interface may be a wireless network interface. In some designs, the network interface may be a Wi-Fi interface. In some embodiments, the network interface may be a Bluetooth interface or cellular WAN (WWAN) interface. In an illustrative example, the wearable device 120 may include more than one network interface. In some designs, the network interface may be a wireline interface. In some designs, the network interface may be omitted.

In the depicted embodiment of FIG. 4, the processor 405 is communicatively and operably coupled with the user interface 440. In various implementations, the user interface 440 may be adapted to receive input from a user or send output to a user. In some embodiments, the user interface 440 may be adapted to an input-only or output-only user interface mode. In various implementations, the user interface 440 may include an imaging display. In some embodiments, the user interface 440 may include an audio interface. In some designs, the audio interface may include an audio input. In assorted designs, the audio interface may include an audio output. In some implementations, the user interface 440 may be touch-sensitive.

In some designs, the wearable device 120 may include an accelerometer, GPS module, magnetometer, or the like operably coupled with the processor 405.

In some embodiments, the user interface 440 may include an input sensor array. In various implementations, the input sensor array may include one or more imaging sensor. In assorted designs, the input sensor array may include one or more audio transducer, a radio-frequency detector, or an ultrasonic audio transducer. In some embodiments, the input sensor array may include image sensing subsystems or modules configurable by the processor 405 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection. In various implementations, the depicted memory 410 may contain processor executable program instruction modules configurable by the processor 405 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection.

In some embodiments, the input sensor array may include audio sensing subsystems or modules configurable by the processor 405 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In various implementations, the depicted memory 410 may contain processor executable program instruction modules configurable by the processor 405 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection.

In the depicted embodiment, the processor 405 is communicatively and operably coupled with the multimedia interface 445. In the illustrated embodiment, the multimedia interface 445 includes interfaces adapted to input and output of audio, video, and image data. In some embodiments, the multimedia interface 445 may include one or more still image camera or video camera and/or, microphone. In some implementations, the multimedia interface 445 may include a wireless communication means configured to operably and communicatively couple the multimedia interface 445 with a multimedia data source or sink external to the wearable device 120. In assorted designs, the multimedia interface 445 may include interfaces adapted to send, receive, or process encoded audio or video. In various embodiments, the multimedia interface 445 may include one or more video, image, or audio encoder. In assorted designs, the multimedia interface 445 may include one or more video, image, or audio decoder. In various implementations, the multimedia interface 445 may include interfaces adapted to send, receive, or process one or more multimedia stream. In various implementations, the multimedia interface 445 may include a GPU. In some embodiments, the multimedia interface 445 may be omitted.

Useful examples of the illustrated wearable device 120 include, but are not limited to, personal computers, servers, tablet PCs, smartphones, or other computing devices. In some embodiments, multiple wearable device 120 devices may be operably linked to form a computer network in a manner as to distribute and share one or more resources, such as clustered computing devices and server banks/farms. Numerous examples of such general-purpose multi-unit computer networks suitable for embodiments of the disclosure, their typical configuration and many standardized communication links are well known to one skilled in the art, as explained in more detail in the foregoing FIG. 2 description.

In some embodiments, an exemplary wearable device 120 design may be realized in a distributed implementation. In an illustrative example, some wearable device 120 designs may be partitioned between a client device, such as, for example, a phone, and a more powerful server system, as depicted, for example, in FIG. 2. In various designs, a wearable device 120 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work. In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary wearable device 120 may be configured to operate on a device with less processing power, such as, for example, various gaming consoles, which may not have sufficient processor power, or a suitable CPU architecture, to adequately support wearable device 120. Various embodiment designs configured to operate on a such a device with reduced processor power may work in conjunction with a more powerful server system.

Figure 5:
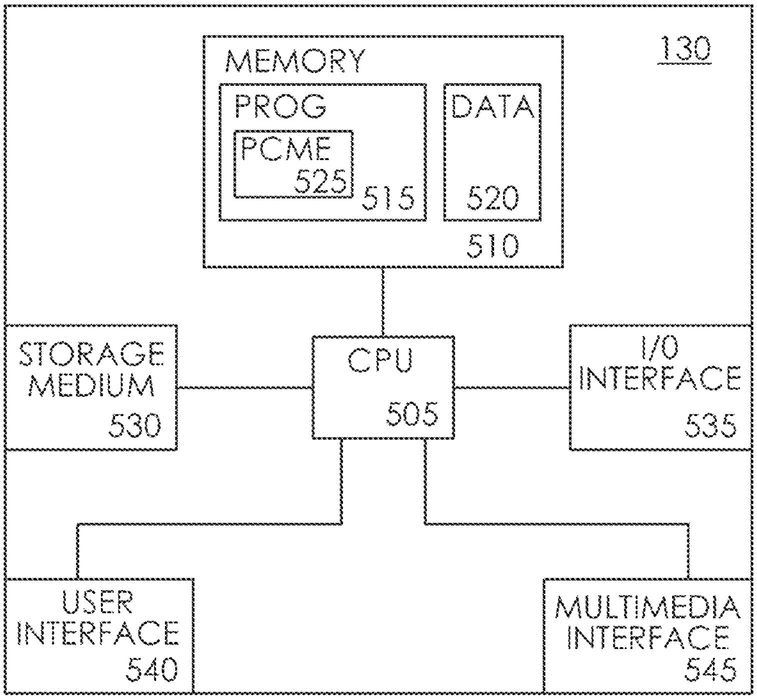
FIG. 5 depicts a structural view of an exemplary physician's or remote caregiver's mobile computing device configured to improve a patient's medication adherence according to aspects of the present disclosure.

FIG. 5 depicts a structural view of an exemplary physician's or remote caregiver's mobile computing device configured to improve a patient's medication adherence. In various examples, the exemplary mobile computing device 130 depicted by FIG. 5 may be representative of a mobile device used by a patient, pharmacy, or non-physician caregiver (i.e., local caregiver), as well as by a physician or remote caregiver. In FIG. 5, the block diagram of the exemplary mobile device 130 includes processor 505 and memory 510. The processor 505 is in electrical communication with the memory 510. The depicted memory 510 includes program memory 515 and data memory 520. The depicted program memory 515 includes processor-executable program instructions implementing the PCME (Patient Care Management Engine) 525. In some embodiments, the PCME 525 may be upgradeable remotely via over-the-air (OTA) methods, or locally using methods such as Bluetooth connection with a mobile device or a thumb drive using USB port for manual upgrade.

In some embodiments, the illustrated program memory 515 may include processor executable program instructions configured to implement an OS (Operating System). In various embodiments, the OS may include processor executable program instructions configured to implement various operations when executed by the processor 505. In some embodiments, the OS may be omitted. In some embodiments, the illustrated program memory 515 may include processor-executable program instructions configured to implement various Application Software. In various embodiments, the application software may be upgradeable remotely via over-the-air (OTA) methods, or locally using methods such as Bluetooth connection with a mobile device or a thumb drive using USB port for manual upgrade. In various embodiments, the application software may include processor executable program instructions configured to implement various operations when executed by the processor 505. In some embodiments, the application software may be omitted.

In the depicted embodiment, the processor 505 is communicatively and operably coupled with the storage medium 530. In the depicted embodiment, the processor 505 is communicatively and operably coupled with the I/O (Input/Output) interface 535. In the depicted embodiment, the I/O interface 535 includes a network interface. In various implementations, the network interface may be a wireless network interface. In some designs, the network interface may be a Wi-Fi interface. In some embodiments, the network interface may be a Bluetooth interface which could be utilized to connect to the connected medication dispenser 110 to perform various operations. In various embodiments, the network interface may include a cellular WAN (WWAN) interface. In an illustrative example, the mobile device 130 may include more than one network interface. In some designs, the network interface may be a wireline interface. In some designs, the network interface may be omitted.

In the depicted embodiment, the processor 505 is communicatively and operably coupled with the user interface 540. In various implementations, the user interface 540 may be adapted to receive input from a user or send output to a user. In some embodiments, the user interface 540 may be adapted to an input-only or output-only user interface mode. In various implementations, the user interface 540 may include an imaging display. In some embodiments, the user interface 540 may include an audio interface. In some designs, the audio interface may include an audio input. In various designs, the audio interface may include an audio output. In some implementations, the user interface 540 may be touch-sensitive.

In some designs, the mobile device 130 may include an accelerometer, magnetometer, and/or GPS module operably coupled with the processor 505.

In some embodiments, the user interface 540 may include an input sensor array. In various implementations, the input sensor array may include one or more imaging sensor, one or more audio transducer, a radio-frequency detector, and/or an ultrasonic audio transducer. In some embodiments, the input sensor array may include image sensing subsystems or modules configurable by the processor 505 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection.

In various implementations, the depicted memory 510 may contain processor executable program instruction modules configurable by the processor 505 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection. In some embodiments, the input sensor array may include audio sensing subsystems or modules configurable by the processor 505 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection.

In various implementations, the depicted memory 510 may contain processor executable program instruction modules configurable by the processor 505 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In the depicted embodiment, the processor 505 is communicatively and operably coupled with the multimedia interface 545. In the illustrated embodiment, the multimedia interface 545 includes interfaces adapted to input and output of audio, video, and image data. In some embodiments, the multimedia interface 545 may include one or more still image camera or video camera and/or one or more microphone.

In some implementations, the multimedia interface 545 may include a wireless communication means configured to operably and communicatively couple the multimedia interface 545 with a multimedia data source or sink external to the mobile device 130. In assorted designs, the multimedia interface 545 may include interfaces adapted to send, receive, or process encoded audio or video. In various embodiments, the multimedia interface 545 may include one or more video, image, or audio encoder. In various designs, the multimedia interface 545 may include one or more video, image, or audio decoder. In various implementations, the multimedia interface 545 may include interfaces adapted to send, receive, or process one or more multimedia stream. In various implementations, the multimedia interface 545 may include a GPU. In some embodiments, the multimedia interface 545 may be omitted.

Useful examples of the illustrated mobile device 130 include, but are not limited to, personal computers, servers, tablet PCs, smartphones, or other computing devices. In some embodiments, multiple mobile device 130 devices may be operably linked to form a computer network in a manner as to distribute and share one or more resources, such as clustered computing devices and server banks/farms. Numerous examples of such general-purpose multi-unit computer networks suitable for embodiments of the disclosure, their typical configuration and many standardized communication links are well known to one skilled in the art, as explained in more detail in the foregoing FIG. 2 description.

In some embodiments, an exemplary mobile device 130 design may be realized in a distributed implementation. In an illustrative example, some mobile device 130 designs may be partitioned between a client device, such as, for example, a phone, and a more powerful server system, as depicted, for example, in FIG. 2. In various designs, a mobile device 130 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work. In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary mobile device 130 may be configured to operate on a device with less processing power, such as, for example, various gaming consoles, which may not have sufficient processor power, or a suitable CPU architecture, to adequately support mobile device 130. Various embodiment designs configured to operate on a such a device with reduced processor power may work in conjunction with a more powerful server system.

Figure 6:
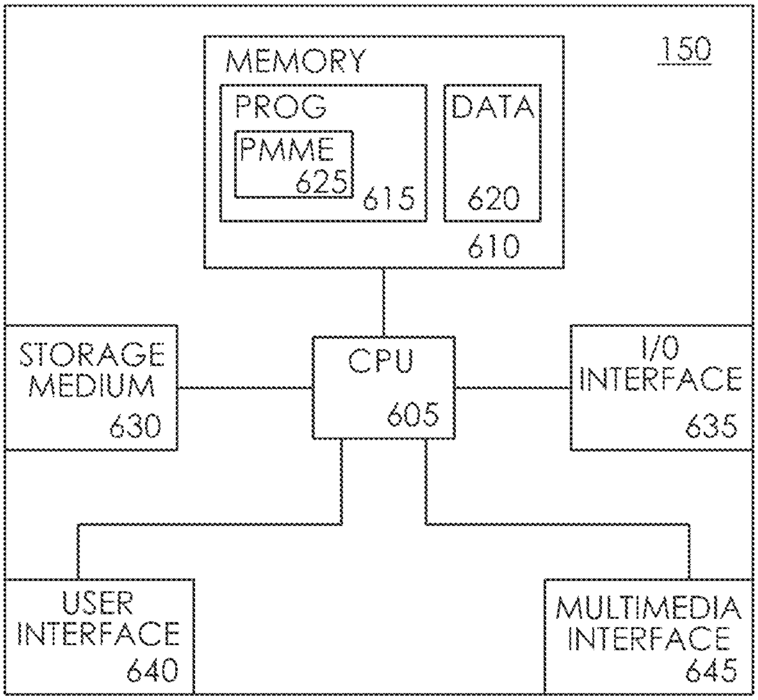
FIG. 6 depicts a structural view of an exemplary pharmacy computing device configured to improve a patient's medication adherence according to aspects of the present disclosure.

FIG. 6 depicts a structural view of an exemplary pharmacy computing device configured to improve a patient's medication adherence. In some examples, the exemplary pharmacy server 150 depicted by FIG. 6 may be representative of a computing device used by a physician's or remote caregiver's office, or a payer, as well as by a pharmacy. In FIG. 6, the block diagram of the exemplary pharmacy server 150 includes processor 605 and memory 610. The processor 605 is in electrical communication with the memory 610. The depicted memory 610 includes program memory 615 and data memory 620. The depicted program memory 615 includes processor-executable program instructions implementing the PMME (Prescription Medication Management Engine) 625.

In some embodiments, the PMME 625 may be upgradeable remotely via over-the-air (OTA) methods, or locally using methods such as Bluetooth connection with a mobile device or a thumb drive using USB port for manual upgrade. In various implementations, the processor-executable program instructions implementing the PMME 625 may be fetched from a central server or web portal. In some embodiments, the illustrated program memory 615 may include processor-executable program instructions configured to implement an OS (Operating System). In various embodiments, the OS may include processor executable program instructions configured to implement various operations when executed by the processor 605. In some embodiments, the OS may be omitted.

In some embodiments, the illustrated program memory 615 may include processor-executable program instructions configured to implement various application software. In various embodiments, the application software may be upgradeable remotely via over-the-air (OTA) methods, or locally using methods such as Bluetooth connection with a mobile device or a thumb drive using USB port for manual upgrade. In various embodiments, the application software may include processor executable program instructions configured to implement various operations when executed by the processor 605. In some embodiments, the application software may be omitted.

In the depicted embodiment, the processor 605 is communicatively and operably coupled with the storage medium 630. In the depicted embodiment, the processor 605 is communicatively and operably coupled with the I/O (Input/Output) interface 635. In the depicted embodiment, the I/O interface 635 includes a network interface. In various implementations, the network interface may be a wireless network interface. In some designs, the network interface may be a Wi-Fi interface. In some embodiments, the network interface may be a Bluetooth interface. In various embodiments, the network interface may include a cellular WAN (WWAN) interface. In an illustrative example, the pharmacy server 150 may include more than one network interface. In some designs, the network interface may be a wireline interface. In some designs, the network interface may be omitted.

In the depicted embodiment, the processor 605 is communicatively and operably coupled with the user interface 640. In various implementations, the user interface 640 may be adapted to receive input from a user or send output to a user. In some embodiments, the user interface 640 may be adapted to an input-only or output-only user interface mode. In various implementations, the user interface 640 may include an imaging display. In some embodiments, the user interface 640 may include an audio interface. In some designs, the audio interface may include an audio input. In various designs, the audio interface may include an audio output. In some implementations, the user interface 640 may be touch-sensitive.

In some designs, the pharmacy server 150 may include an accelerometer, GPS module, and/or magnetometer operably coupled with the processor 605.

In some embodiments, the user interface 640 may include an input sensor array. In various implementations, the input sensor array may include one or more imaging sensor. In various designs, the input sensor array may include one or more audio transducer, a radio-frequency detector, and/or an ultrasonic audio transducer.

In some embodiments, the input sensor array may include image sensing subsystems or modules configurable by the processor 605 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection. In various implementations, the depicted memory 610 may contain processor executable program instruction modules configurable by the processor 605 to be adapted to provide image input capability, image output capability, image sampling, spectral image analysis, correlation, autocorrelation, Fourier transforms, image buffering, image filtering operations including adjusting frequency response and attenuation characteristics of spatial domain and frequency domain filters, image recognition, pattern recognition, or anomaly detection.

In some embodiments, the input sensor array may include audio sensing subsystems or modules configurable by the processor 605 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In various implementations, the depicted memory 610 may contain processor executable program instruction modules configurable by the processor 605 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection.

In the depicted embodiment, the processor 605 is communicatively and operably coupled with the multimedia interface 645. In the illustrated embodiment, the multimedia interface 645 includes interfaces adapted to input and output of audio, video, and image data. In some embodiments, the multimedia interface 645 may include one or more still image camera or video camera and/or one or more microphone. In some implementations, the multimedia interface 645 may include a wireless communication means configured to operably and communicatively couple the multimedia interface 645 with a multimedia data source or sink external to the pharmacy server 150. In various designs, the multimedia interface 645 may include interfaces adapted to send, receive, or process encoded audio or video. In various embodiments, the multimedia interface 645 may include one or more video, image, or audio encoder. In various designs, the multimedia interface 645 may include one or more video, image, or audio decoder. In various implementations, the multimedia interface 645 may include interfaces adapted to send, receive, or process one or more multimedia stream. In various implementations, the multimedia interface 645 may include a GPU. In some embodiments, the multimedia interface 645 may be omitted.

Useful examples of the illustrated pharmacy server 150 include, but are not limited to, personal computers, servers, tablet PCs, smartphones, or other computing devices. In some embodiments, multiple pharmacy server 150 devices may be operably linked to form a computer network in a manner as to distribute and share one or more resources, such as clustered computing devices and server banks/farms. Various examples of such general-purpose multi-unit computer networks suitable for embodiments of the disclosure, their typical configuration and many standardized communication links are well known to one skilled in the art, as explained in more detail in the foregoing FIG. 2 description.

In some embodiments, an exemplary pharmacy server 150 design may be realized in a distributed implementation. In an illustrative example, some pharmacy server 150 designs may be partitioned between a client device, such as, for example, a phone, and a more powerful server system, as depicted, for example, in FIG. 2. In various designs, a pharmacy server 150 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work.

In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary pharmacy server 150 may be configured to operate on a device with less processing power, such as, for example, various gaming consoles, which may not have sufficient processor power, or a suitable CPU architecture, to adequately support pharmacy server 150. Various embodiment designs configured to operate on a such a device with reduced processor power may work in conjunction with a more powerful server system.

Figure 7:
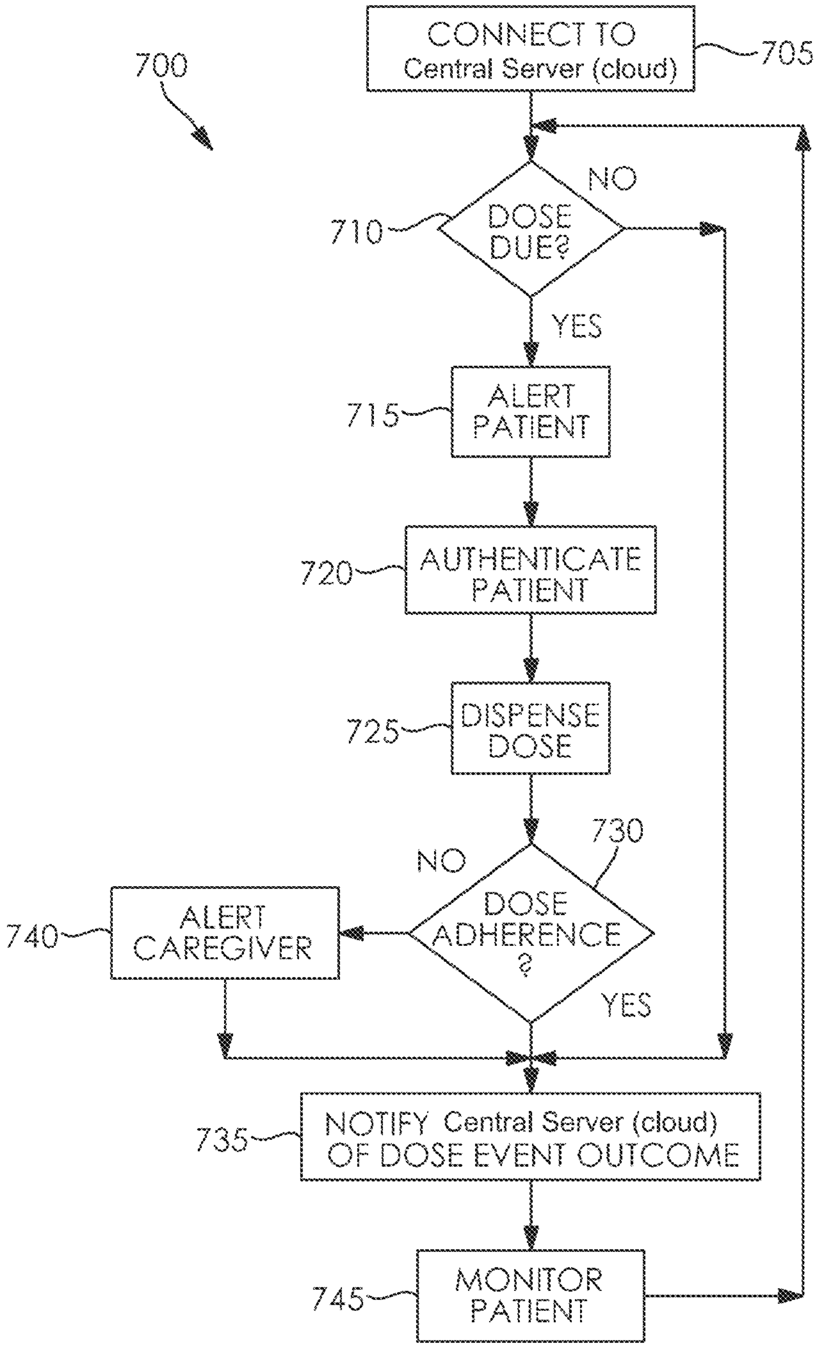
FIG. 7 depicts an exemplary process flow of an embodiment Interactive Patient Treatment Engine (IPTE) for improving a patient's medication adherence according to aspects of the present disclosure.

FIG. 7 depicts an exemplary process flow of an embodiment Interactive Patient Treatment Engine (IPTE) for improving a patient's medication adherence. The method depicted in FIG. 7 is shown from the perspective of the IPTE 325 implemented via processor-executable program instructions executing on the processor 305 of the connected medication dispenser 110, depicted in FIG. 3. In the illustrated embodiment, the IPTE 325 executes as program instructions on the processor 305 configured in the IPTE 325 host connected medication dispenser (110, 1800, 1900). In some embodiments, the IPTE 325 may execute as a cloud service communicatively and operatively coupled with system services, hardware resources, or software elements local to and/or external to the IPTE 325 on the host connected medication dispenser 110.

The depicted method 700 begins at step 705 with the processor 305 connecting to the cloud platform (e.g., cloud server or central server 195 via the cloud 115). The method continues at step 710 with the processor 305 performing a test to determine if a dose is due. Upon a determination by the processor 305 at step 710 that a dose is not due, the method continues at step 735 with the processor 305 notifying the cloud platform that a dose was not delivered because a dose was not due, and the method continues at step 745 with the processor 305 monitoring the patient. Upon a determination by the processor 305 at step 710 that a dose is due, the method continues at step 715 with the processor 305 alerting the patient that a dose is due. The method continues at step 720 with the processor 305 authenticating the patient, followed by step 725 with the processor 305 causing the connected medication dispenser to dispense the dose.

The method continues at step 730 with the processor 305 determining dose adherence, including determining based on sensor input if the patient consumed the dose. Upon a determination by the processor 305 at step 730 the patient did not consume the dose, the method continues at step 740 with the processor 305 alerting the caregiver of the missed dose, and at step 735 with the processor 305 notifying the Nucleus Rx cloud of the dose event outcome. Upon a determination by the processor 305 at step 730 the patient did consume the dose, the method continues at step 735 with the processor 305 notifying the cloud platform of the dose event outcome. For example, at step 735 the processor 305 may notify the cloud platform of a dose event outcome including: dose missed, dose dispensed, erroneous dispense, or dispense failed. The method continues at step 745 with the processor 305 monitoring the patient, and at step 710 with the processor 305 performing a test to determine if a dose is due.

Figure 8:
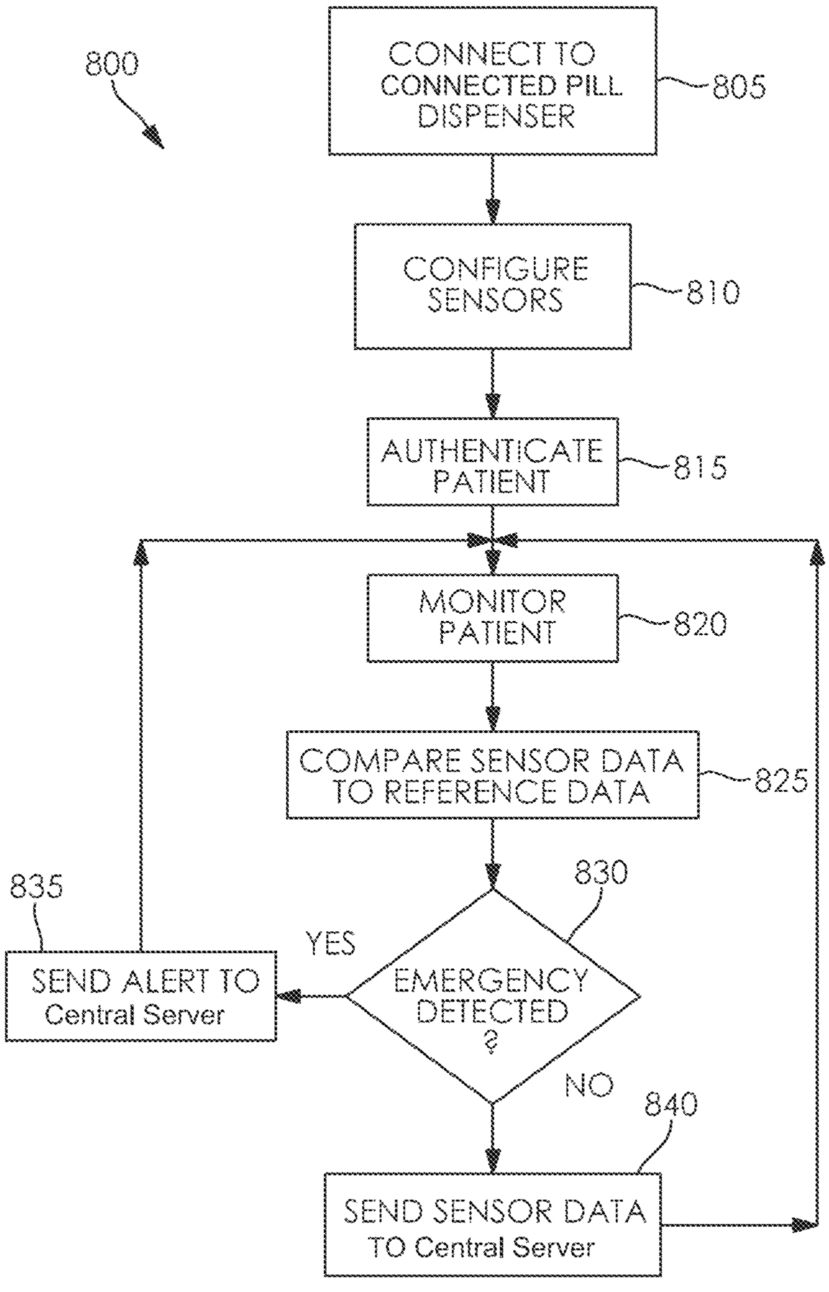
FIG. 8 depicts an exemplary process flow of an embodiment Patient Parameter Monitoring Engine (PPME) for improving a patient's medication adherence according to aspects of the present disclosure.

FIG. 8 depicts an exemplary process flow of an embodiment Patient Parameter Monitoring Engine (PPME) for improving a patient's medication adherence. The method depicted in FIG. 8 is shown from the perspective of the PPME 425 implemented via processor-executable program instructions executing on the processor 405 of the wearable device 120 depicted in FIG. 4. In the illustrated embodiment, the PPME 425 executes as program instructions on the processor 405 configured in the PPME 425 host wearable device 120, depicted in at least FIG. 1, FIG. 2, and FIG. 4. In some embodiments, the PPME 425 may execute as a cloud service communicatively and operatively coupled with system services, hardware resources, or software elements local to and/or external to the PPME 425 host wearable device 120.

The depicted method 800 begins at step 805 with the processor 405 connecting to the connected medication dispenser. In addition to connecting with the dispenser, the wearable device could be connected to the pharmacy or the authorized caregiver's mobile app for configuration. In an illustrative example, configuration parameters can be pushed by the physician's or remote caregiver's office or the pharmacist via the connected medication dispenser to the patient's wearable device. In some examples, similar configuration may be achieved by the pharmacist's mobile app during a face-to-face set up, or similarly with the authorized caregiver's mobile app. In various embodiments, the connection to the dispenser will also be required for external patient authentication (for example, using touch ID of the wearable) for dispensing meds. In some scenarios, for the purpose of configuration of patient parameters, the wearable could be connected to the central server 195. The method continues at step 810 with the processor 405 configuring patient monitoring sensors, followed by step 815 wherein the processor 405 authenticates the patient based on sensor input. The method continues at step 820 with the processor 405 monitoring the patient based on the sensor data, and at step 825 with the processor 405 comparing the sensor data to reference sensor data representative of patient baseline condition.

At step 830, the processor 405 performs a test to determine if a patient emergency condition is detected by the processor 405, based on the comparison performed by the processor 405 at step 825. Upon a determination by the processor 405 at step 830 that a patient emergency condition is detected, the method continues at step 835 with the processor 405 sending an alert representative of the emergency condition to cloud platform (e.g., cloud server or central server 195 via the cloud 115), and the method continues at step 820 with the processor 405 monitoring the patient. Upon a determination by the processor 405 at step 830 that a patient emergency condition is not detected, the method continues at step 840 with the processor 840 sending the patient monitor sensor data to cloud platform, and the method continues at step 820 with the processor 405 monitoring the patient.

Figure 9:
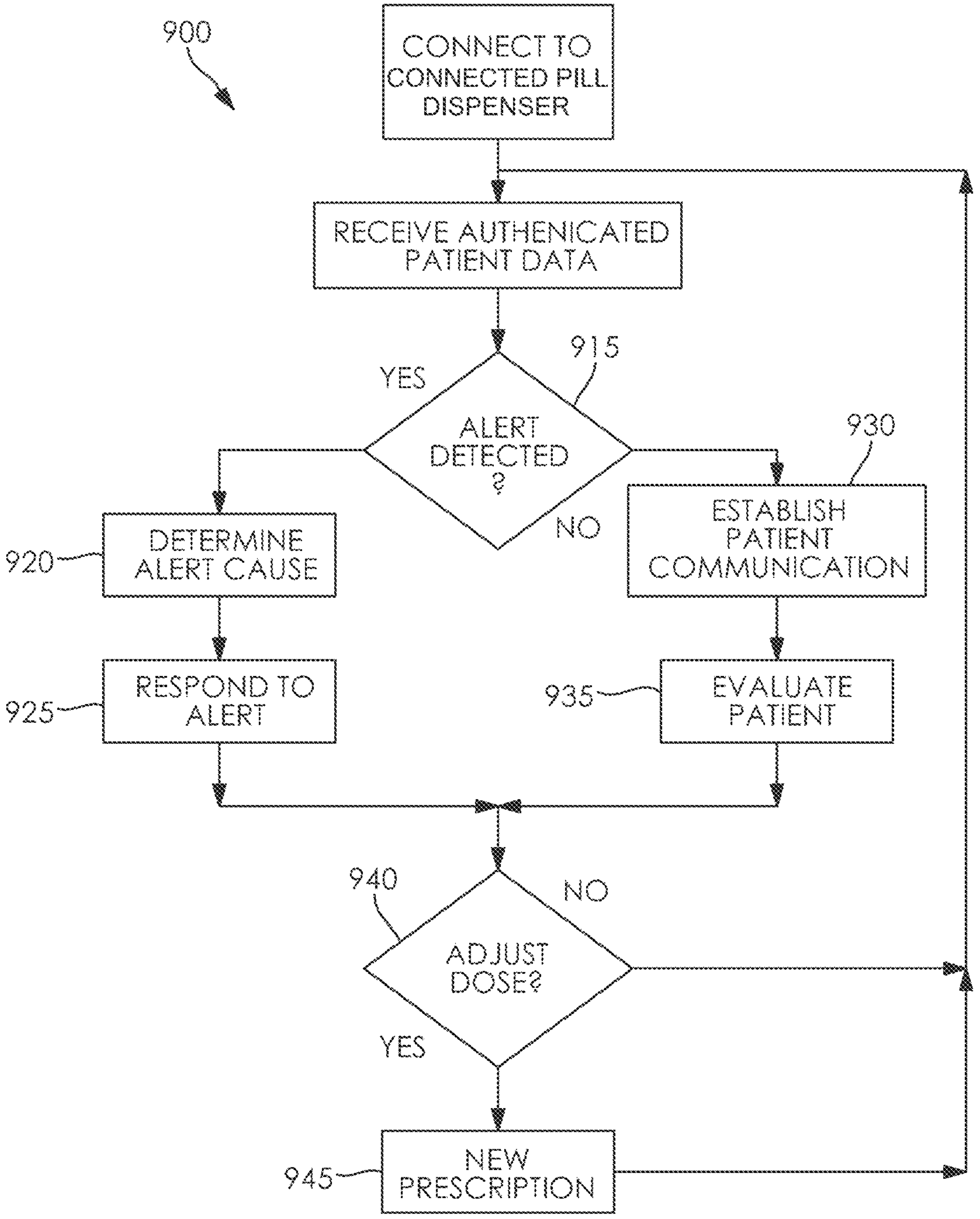
FIG. 9 depicts an exemplary process flow of an embodiment Patient Care Management Engine (PCME) for improving a patient's medication adherence according to aspects of the present disclosure.

FIG. 9 depicts an exemplary process flow of an embodiment Patient Care Management Engine (PCME) for improving a patient's medication adherence. The method depicted in FIG. 9 is shown from the perspective of the PCME 525 implemented via processor-executable program instructions executing on the mobile device 130 processor 505, depicted in FIG. 5. In various embodiment implementations, the scope of PCME 525 target computing platforms may include collaborative computing distributed across multiple cloud and device-centric processors. In an illustrative example, the main computation may take place on the central server or the cloud platform. The central server or the cloud platform may collect data from the dispenser and the wearable, and compute against the prescription configured by the pharmacy and the patient parameters set by the physician's or remote caregiver's office. The platform may then disseminate action and information to the subscribed parties, e.g., physician's mobile device and/or web portal, pharmacist's mobile device and/or web portal, caregiver's mobile device and/or web portal.

In some designs, the prescription configuration by the pharmacists, and the patient parameters set by the physician's or remote caregiver's office, may be mutually exclusive activities. Prescription information and medication count may alert the pharmacy about replenishment requirements, whereas patient's parameters may allow a physician or remote caregiver to adjust medication, which may in-turn adjust the medication replenishments needs for the pharmacy. In the illustrated embodiment, the PCME 525 executes as program instructions on the processor 505 configured in the PCME 525 host mobile device 130, depicted in at least FIG. 1, FIG. 2, and FIG. 5. In some embodiments, the PCME 525 may execute as a cloud service communicatively and operatively coupled with system services, hardware resources, or software elements local to and/or external to the PCME 525 host mobile device 130.

The depicted method 900 begins at step 905 with the processor 505 connecting to the connected medication dispenser. The method continues at step 910 with the processor 505 receiving authenticated patient data and continues at step 915 with the processor 505 performing a test to determine if an alert is detected. Upon a determination by the processor 505 at step 915 an alert was detected, the method continues with the processor 505 at step 920 determining the alert cause, and the processor 505 at step 925 responding to the alert. Upon a determination by the processor 505 at step 915 an alert was not detected, the method continues with the processor 505 at step 930 establishing patient communication, and the processor 505 at step 935 evaluating the patient. the method continues at step 940 with the processor 505 performing a test to determine if the patient's dose should be adjusted, in response to either the alert or evaluation. Upon a determination by the processor 505 at step 940 the dose should be adjusted, the method continues a step 945 with the processor 505 generating a new prescription based on a prescribed treatment protocol, and at step 910 with the processor 505 receiving authenticated patient data.

Figure 10:
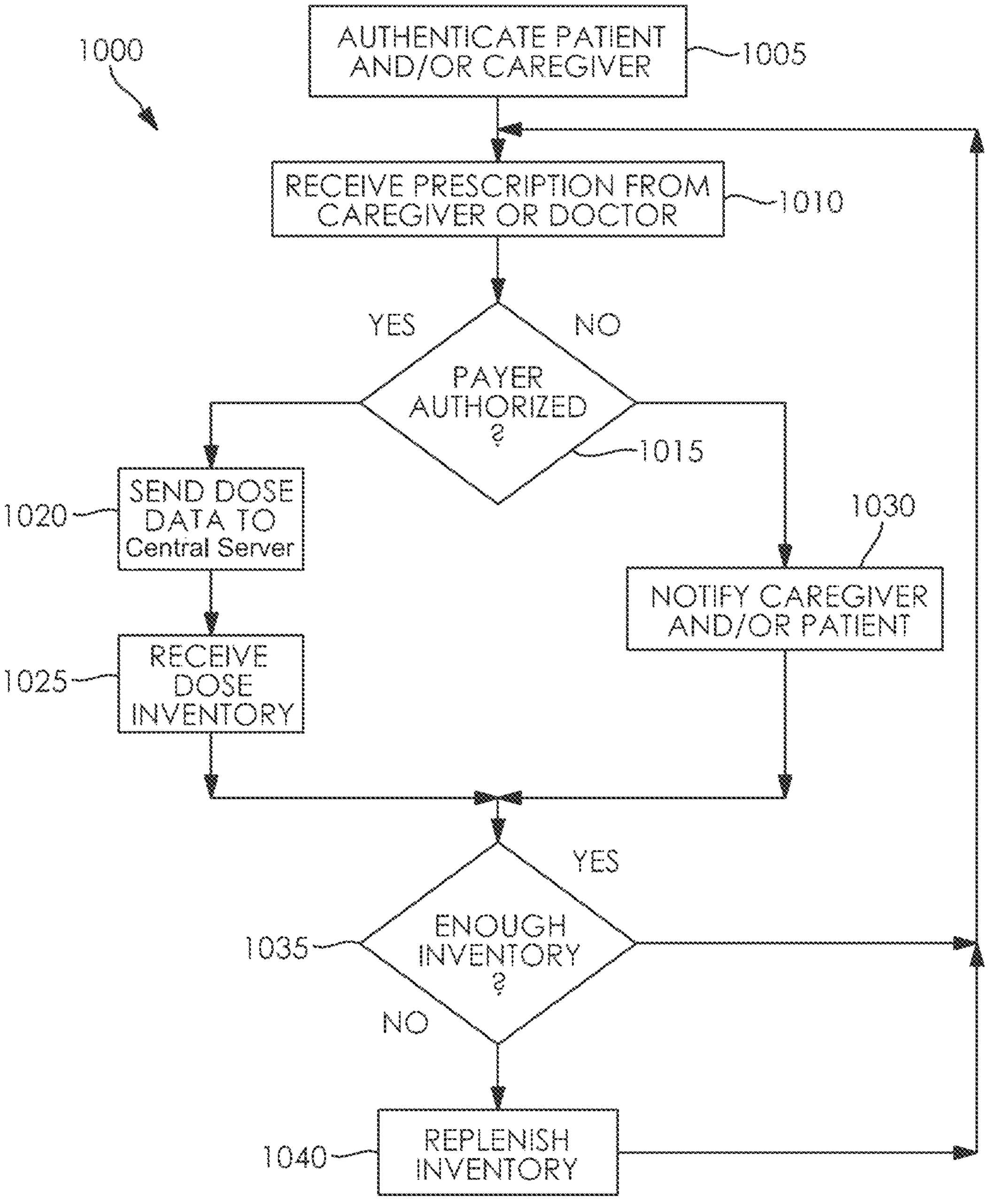
FIG. 10 depicts an exemplary process flow of an embodiment Prescription Medication Management Engine (PMME) for improving a patient's medication adherence according to aspects of the present disclosure.

FIG. 10 depicts an exemplary process flow of an embodiment Prescription Medication Management Engine (PMME) improving a patient's medication adherence. The method depicted in FIG. 10 is given from the perspective of the PMME 625 implemented via processor-executable program instructions executing on the pharmacy server 150 processor 605, depicted in FIG. 6. In the depicted example, the pharmacy manages through a web portal or a mobile app, and the information exchange is through the cloud platform (i.e., cloud server). In the illustrated embodiment, the PMME 625 executes as program instructions on the processor 605 configured in the PMME 625 host pharmacy server 150, depicted in at least FIG. 1, FIG. 2, and FIG. 6. In some embodiments, the PMME 625 may execute as a cloud service communicatively and operatively coupled with system services, hardware resources, or software elements local to and/or external to the PMME 625 host pharmacy server 150.

The depicted method 1000 begins at step 1005 with the processor 605 authenticating the patient and/or caregiver and continues at step 1010 with the processor 605 receiving a new prescription from the caregiver or physician. In some embodiments, the treatment regime using the connected medication dispenser is recommended by the physician or remote caregiver and the payer pays for the treatment. In this case, the physician or remote caregiver writes the new prescription including the connected medication dispenser.

The prescription may come directly from the physician or remote caregiver to the pharmacy system, or the patient/local caregiver may manually provide the prescription to the pharmacy. In various implementations, when the device is paid for by the provider (for example, a hospital, or a healthcare facility), the local caregiver/patient will provide the prescription.

At step 1015, the processor 605 performs a test to determine if the prescription received from the caregiver is authorized by a payer. Upon a determination by the processor 605 at step 1015 the prescription is authorized, the method continues with the processor 605 at step 1020 sending dose data to the connected medication dispenser, and the processor receiving at step 1025 dose inventory data from the connected medication dispenser. Upon a determination by the processor 605 at step 1015 the prescription is not authorized, the processor 605 at step 1030 notifies the caregiver and/or patient the prescription is not payer authorized. The method continues at step 1035 with the processor 605 performing a test to determine if the connected medication dispenser has sufficient medication dose inventory. Upon a determination by the processor 605 at step 1035 that the connected medication dispenser does not have sufficient medication dose inventory, the method continues at step 1040 with the processor 605 requesting that the dose inventory of medication in the connected medication dispenser be replenished. The method continues at step 1010 with the processor 605 receiving a prescription from the remote caregiver or physician.

Figure 11:
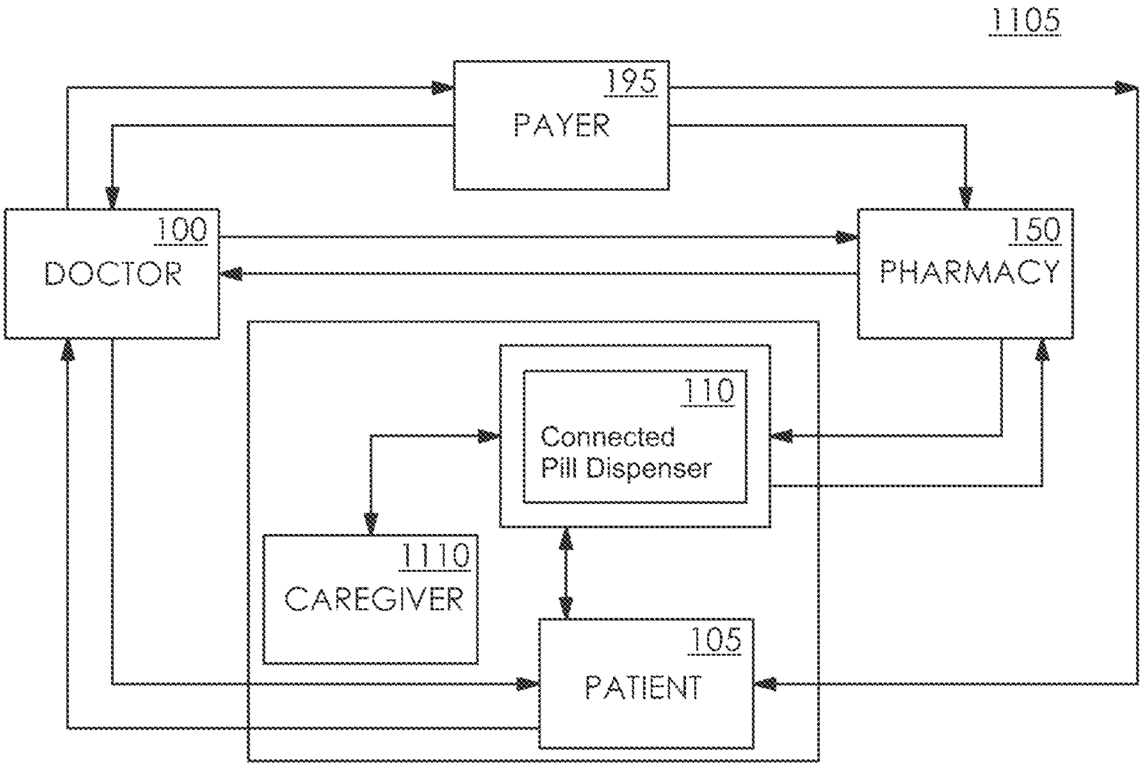
FIG. 11 depicts an exemplary collaboration diagram illustrating communication among patient and patient worn devices, physician, pharmacy, payer, caregiver, a central server, and a connected medication dispenser to enhance a patient's medication adherence according to aspects of the present disclosure.

FIG. 11 depicts an exemplary collaboration diagram illustrating patient, provider (physician or remote caregiver), and payer interaction to enhance a patient's medication adherence. In FIG. 11, the physician 100 prescribes medication to treat the patient 105 with the assistance of the connected medication dispenser 110. In the depicted example, the connected medication dispenser 110 gets medications for the patient 105, and sends alerts when doses are missed. In various embodiments, the connected medication dispenser 110 may send a missed dose alert to one or more caregiver 1110. In some embodiments, the connected medication dispenser 110 may send a missed dose alert to the patient 105 or to the physician 100. Various connected medication dispenser 110 designs may notify the caregiver 1110 or physician 100 of medication adherence or medication compliance determined by the connected medication dispenser 110 as a function of sensor data.

In various embodiments, medication adherence or medication compliance may be determined by the connected medication dispenser 110 as a function of data captured by one or more sensor configured in a patient-controlled device, a patient wearable device, or the connected medication dispenser 110. In the illustrated embodiment, the connected medication dispenser 110 sends patient 105 vital and parametric information collected from one or more wearable device to the physician 100. In the depicted example, the physician 100 prescribes a modified patient 105 medication dose adjusted as a function of the patient 105 vital and parametric information received from the connected medication dispenser 110. In the illustrated embodiment, the physician 100 sends the modified patient 105 medication dose to the connected medication dispenser 110. In the depicted example, the caregiver 1110 may also receive medications from the connected medication dispenser 110, receive alerts from the connected medication dispenser 110 on a missed dose, or receive notification of compliance from the connected medication dispenser 110.

In various embodiments, the physician or remote caregiver 100 may diagnose a medical condition of the patient 105 based on an evaluation of the patient 105 medical history. In some examples, the physician or remote caregiver 100 may determine treatment of the medical condition of the patient 105 includes use of the connected medication dispenser 110, such as based on the patient 105 medical condition as diagnosed by the physician or remote caregiver 100. For example, the physician or remote caregiver 100 may prescribe the connected medication dispenser 110 to the patient based on the patient 105 medical condition. In the illustrated example, the physician or remote caregiver 100 forwards scripts or a change of scripts to the pharmacy server 150, and the pharmacy server 150 forwards manual patient 105 compliance reports to the physician or remote caregiver 100. In the depicted example, the connected medication dispenser 110 alerts the pharmacy server 150 for refills, and further, notifies the pharmacy server 150 of compliance. In the depicted example, the pharmacy fills the prescriptions, programs medication schedules into the connected medication dispenser 110, and trains both patients and caregivers. In the illustrated example, the payer authorizes the patient 105 treatment using the connected medication dispenser 110, such as via a payer management server (e.g., 195) and the payer pays the physician or remote caregiver 100 for services via communications from the same or a different server. In the depicted example, the payer pays the pharmacy for medications, the use of the connected medication dispenser 110, and the pharmacy dispensing services.

Figure 12:
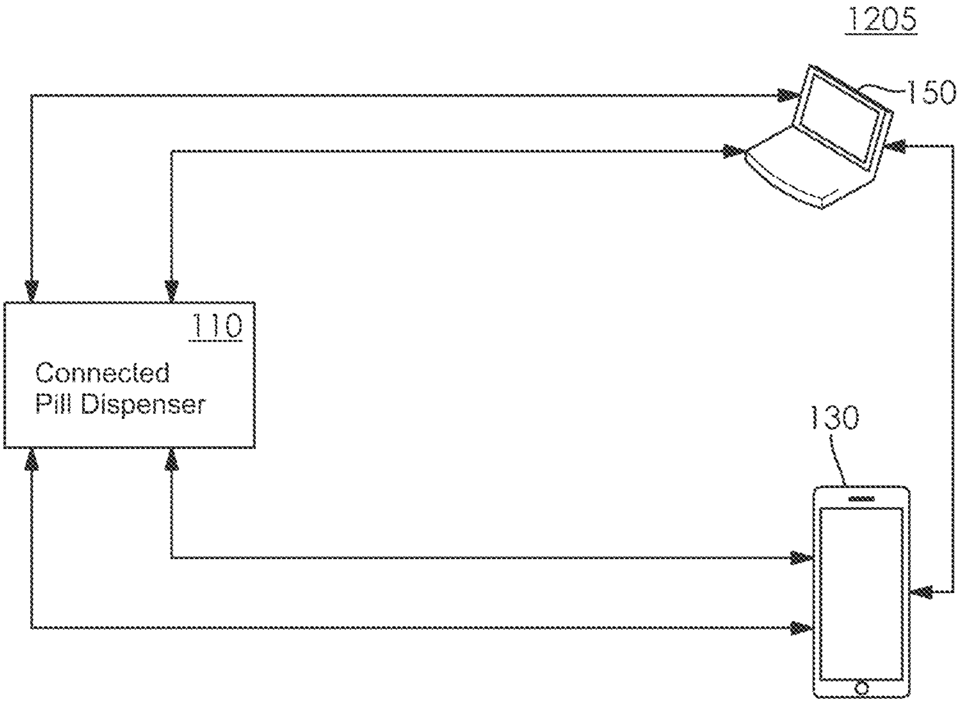
FIG. 12 depicts an exemplary conceptual diagram illustrating software, and various components and interactions therebetween to enhance a patient's medication adherence according to aspects of the present disclosure.

FIG. 12 depicts an exemplary conceptual diagram illustrating the connected medication dispenser 110 and interactions with a mobile device 130, which may be a device of the patient, pharmacy, non-physician caregiver, or a physician, and a pharmacy server 150, to enhance a patient's medication adherence. In FIG. 12, the connected medication dispenser 110 collaborates with the pharmacy server 150 and the mobile app on the mobile device 130. In the depicted example, the connected medication dispenser 110 alerts the pharmacy server 150 of medication quantity and notifies of compliance for payers and physicians. In the illustrated example, the connected medication dispenser 110 provides dose reminders to patients and compliance alerts to patients and caregivers.

In the depicted example, the mobile app on the mobile device 130 of the physician/caregiver enables remote adjustment of doses per script in the connected medication dispenser 110, such as via the patient/local caregiver mobile app. Communication between a physician, remote caregiver, pharmacist, and the patients/local caregivers may also be possible via the mobile app on the patient and physician/remote caregiver's mobile devices. In some exemplary scenarios, if a patient/caregiver does not respond to a timed dispense of medication after a time window set by the pharmacist and/or physician/remote caregiver, a missed dose may not be dispensed until time for next dosing to avoid multiple doses within a short interval contrary to the prescribed dosing interval. Some embodiments may include a pre-set time window to authenticate and dispense meds. In an illustrative example, if the patient/caregiver does not respond within the given time window, the medications may not be dispensed, and the event may be noted as "missed dose." For example, if the patient/caregiver successfully authenticates him/herself to dispense doses, but the machine falters, the event may be recorded as an unsuccessful/erroneous dispense.

Authorization is generally expected within a set period, for example, within an hour of the first reminder. Once the patient or caregiver has obtained authorization, the connected medication dispenser may trigger release of the patient's medications, such as to a small cup or bin, or the like. The medications may be dispensed from the connected medication dispenser as per preset programs based on a patient's prescriptions and patient input (i.e., standard wake and sleep times, times of meals, etc.), for example, one of medication A on waking and two of medication B and one of medication C after breakfast. When the medications are dispensed within the pre-defined time threshold, an event is generated indicating positive adherence for the particular dose, i.e., scheduled dose. The patient may be directed by the connected medication dispenser to take the medications such that their actions can be captured by a camera on the dispenser. For example, real-time video and image analysis may be performed utilizing computer vision and machine learning techniques to identify whether the patient took the medication. Such analysis enables improved accuracy for recording patient adherence per dose, such as noting medication ingestion/use actions and the timing of the adherence and may also improve patient compliance.

If a dose is missed, that is, the patient or the caregiver does not trigger medication release from the connected medication dispenser by lack of successful authorization or non-interaction with the system or connected medication dispenser, an event may be generated indicating negative adherence for that particular dose. Further, the connected medication dispenser will also act as a hub for reading vital signs through wearable gadgets worn by the patients and communicating them to central server for storing and forwarding to interested parties, such as, physician's office or the caregiver. In some embodiments, the change in patient parameters and vital signs read from the wearable devices would determine even higher degree of compliance in addition to a positive dispensing event and/or the image/video/voice analysis.

Figure 13:
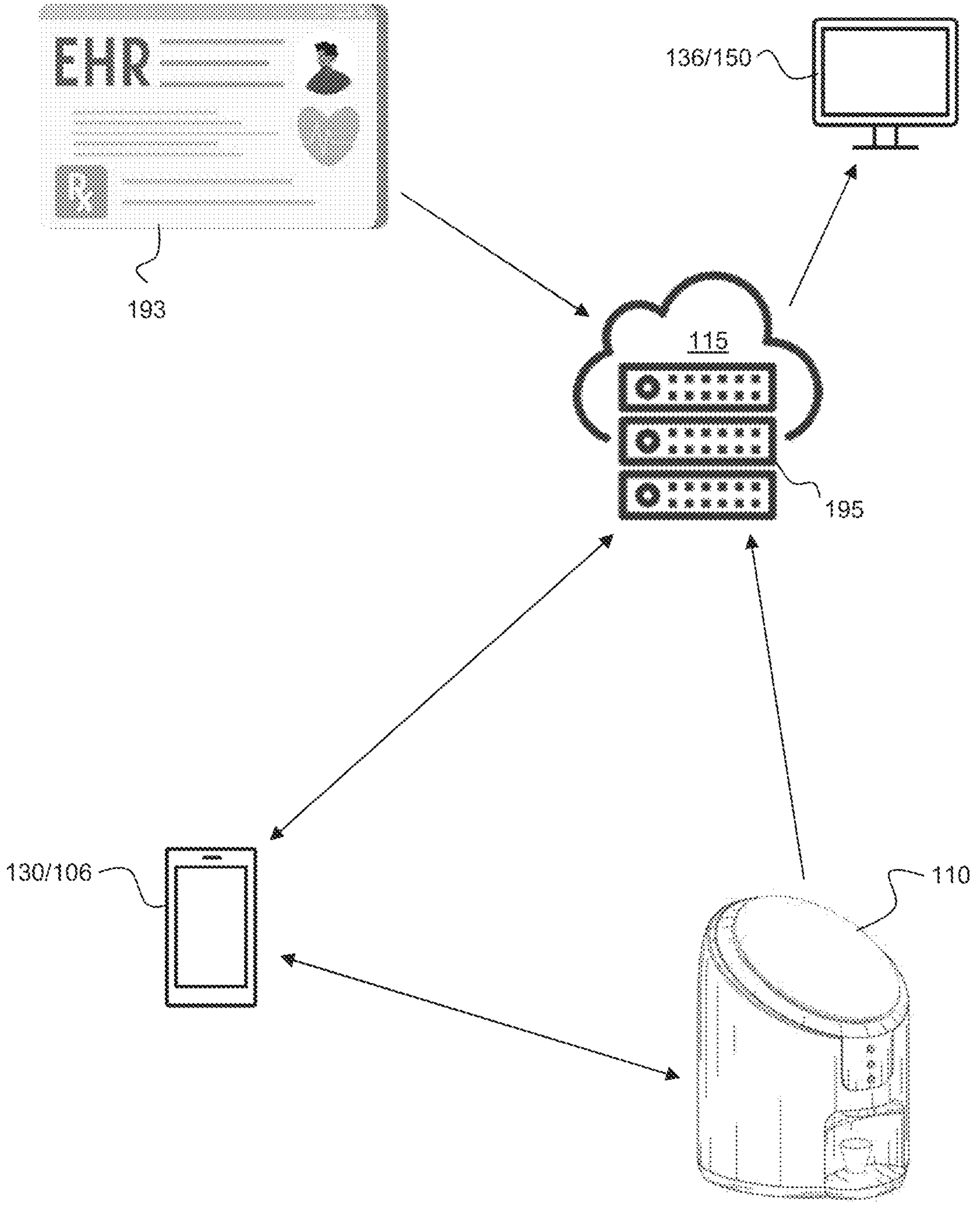
FIG. 13 depicts a schematic view of an exemplary medication adherence network according to aspects of the present disclosure.

FIG. 13 depicts another schematic view of an exemplary medication adherence network configured to automatically determine whether a patient took a prescribed medicine dose provided by any of the various embodiments of the connected medication dispenser disclosed herein. The network and devices involved will include at least those discussion regarding FIG. 1 and may include additional connections and software applications as discussed below. An exemplary system includes a connected medication dispenser 110 configured for communication via the cloud 115 with a mobile device, such as the mobile device of a patient or local or remote caregiver (106), pharmacy, or physician (130). The system may also provide web-based communication via the cloud 115 with a web portal providing authorized access to a web application configured for specific services, such as pharmacy-centric, physician-centric, remote-caregiver-centric, patient/local-caregiver-centric services 136, or various web accessible servers, such as a pharmacy, remote caregiver, or physician server 150, payer management server or central cloud server 195, and the electronic health record 193 of the patient, that may be stored on a payer (insurer) or physician's or remote caregiver's server.

While not shown in this FIG. 13 for simplicity's sake, the system may further include a patient wearable device 120 and/or other home health monitoring devices that may communicate with the connected medication dispenser 110, such as via a mobile device 106 of the patient or local caregiver. In certain cases, data collected from devices that are not communication enabled, i.e., not connected to or connectable with the patient/caregiver mobile device, may be entered manually by an authenticated user. Also not shown is communication between the central cloud server 195 or mobile applications on the mobile devices (130/106) with third party connected laboratory services requested remotely by the healthcare provider and/or connected rehabilitation services requested by the healthcare provider.

In the depicted example, the cloud server 195 is a computing device configured to host and manage data. For example, the cloud server 195 may be the central server that collects information from the connected medication dispenser 110, prescription data from the pharmacy server 150, information from the payer or physician or remote caregiver, such as the electronic health record 193 of the patient, information from the patient mobile device, etc. The cloud server 195 could be implemented on a public, private, or hybrid cloud infrastructure. Accordingly, the cloud server 195 has the capability to integrate with one or multiple different electronic health record (EHR) systems of healthcare providers. It establishes two-way communication with the EHR system to fetch information from and send information to the EHR system based on patient authorization.

Specifically, the presently disclosed system may authenticate a patient and pass patient authorization to the server housing the EHR to request selected patient data elements, such as patient records (e.g., patient coordinates and selective health data elements), patient active and past electronic prescription data, patient lab report data, and the like. The system may then populate the patient's interfaces (mobile app on patient's/caregiver's mobile device 130/106, patient connected medication dispenser 110) with selected patient record and prescription data to assist the patient or the caregiver and/or program the connected medication dispenser 110 based on the electronic prescription data.

Moreover, the cloud server 195 may collect real-time EHR records when healthcare providers update patient prescriptions and push such updated information to the connected medication dispenser and update the dispense programming accordingly. For example, a medication may be suspended or cancelled from subsequent dispense actions by the connected pill dispenser 110 if the provider stops a medication mid-cycle. A medication dose may be increased or decreased at the next dispense action of the connected pill dispenser 110 if the provider increases or decreases doses of certain medications. A dose may be delivered immediately by the connected medical dispenser 110, i.e., not within the normal dispense schedule, if the provider deems immediate intervention is medically advised. The healthcare provider, i.e., physician's office, or remote caregiver, or larger medical systems, may access web applications via a web portal (150/136), such as hosted on a central server 195, to perform such medication updates remotely.

The presently disclosed systems also provide mobile app(s) configured for the patients or the caregivers of the patients that are accessible via the patient/caregiver mobile devices 106. The mobile applications may be configured to perform specific tasks. Exemplary tasks include allowing the patient and/or caregiver to load medications, such as prescription medication or over the counter medications, to the connected medication dispenser. Such actions may be based on a physician's or remote caregiver's prescription, such as electronically transmitted to the patient/local caregiver mobile device(s) and/or connected medication dispenser. Based on the instructions of the electronic prescriptions, the mobile app on the patient/local caregiver mobile device(s)

guides the patient or the local caregiver through an effortless process to load medication in the most error-free way possible.

The patient/caregiver mobile app(s) may also remind the patient or caregiver about scheduled medication doses and provide an alert when a next scheduled dose is available. Before receiving the next medication dose from the connected medication dispenser, the patient/caregiver must authenticate a dispense. That is, the patient/caregiver must use one of several means to provide positive identification to the connected medication dispenser. For example, the mobile app may use the patient/caregiver mobile device's (e.g., a smartphone or a tablet computer) inbuilt biometric sensor to authenticate the user (patient or the caregiver). The mobile app may also allow the patient/caregiver to delay, i.e., snooze, a dose for a pre-determined time or skip a dose, such as when valid reasons are provided to the system.

The mobile app may remind the patient/caregiver to take daily wellness checks via a pre-set questionnaire personalized by the patient's remote provider, i.e., remote provider may be the physician or remote caregiver using their provider web application to personalize the patient's questionnaire based on the diagnosis and treatment plan. In general, such questionnaire are designed to provide simplified choices of response to enhance patient compliance. The mobile app may remind the patient/caregiver to collect the patients' physiologic data via pre-configured connected physiologic devices (e.g., wearable devises that provide blood pressure, heart rate, weight, electrocardiogram, blood glucose level, etc., or home-based devices as described hereinabove). The data from such devices may be recorded automatically via the cloud 115 to the central server for patient/caregiver's view through their mobile app, as well as for the remote healthcare provider's view through their mobile app or web portal.

The mobile app may remind the patient/local caregiver of healthy habits related to diet and lifestyles. Such reminders may be pre-set and personalized by the healthcare provider using the provider's mobile app or web portal. Moreover, the mobile app may provide disease-related educational content for patients or caregivers to keep up to date about management of the patients' diseases.

The physician/remote caregiver may access a web-based software application, i.e., via a web portal, which provides a complete view of a patient's record of medicine adherence, physiologic data, daily wellness data and lab data. Such data may assist the physician/remote caregiver to perform holistic patient assessments remotely.

Figure 14A:
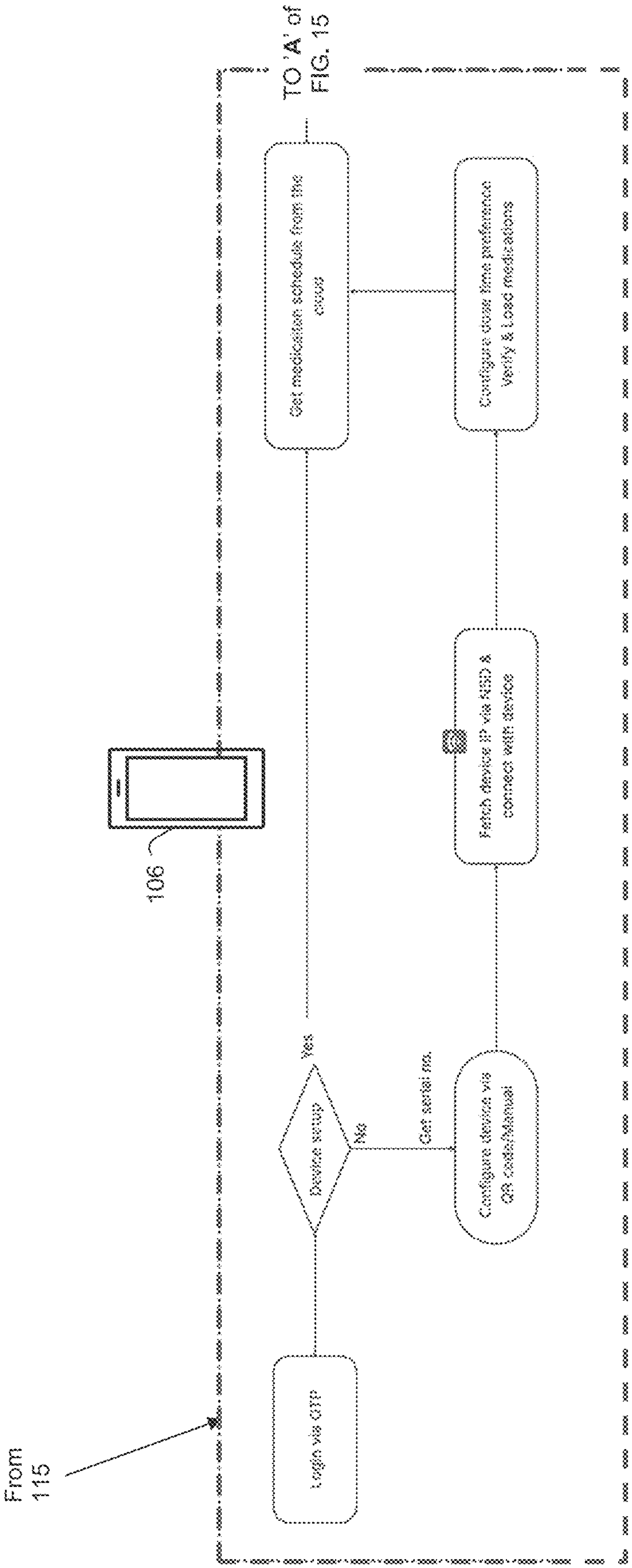
FIGS. 14A-14C depict an exemplary process flow of a software application executing on a mobile device of a patient or caregiver according to aspects of the present disclosure.
Figure 14B:
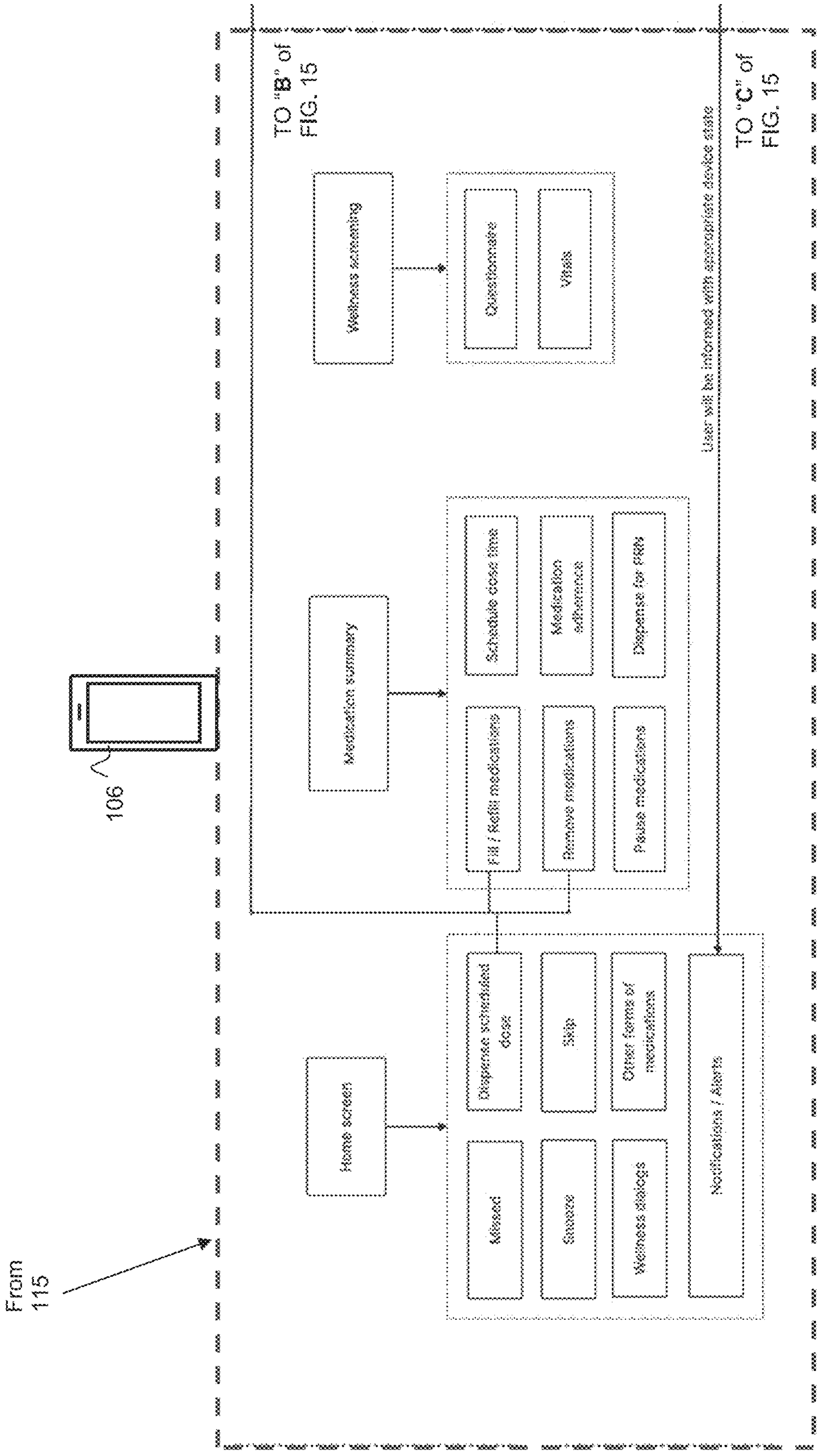
Figure 14C:
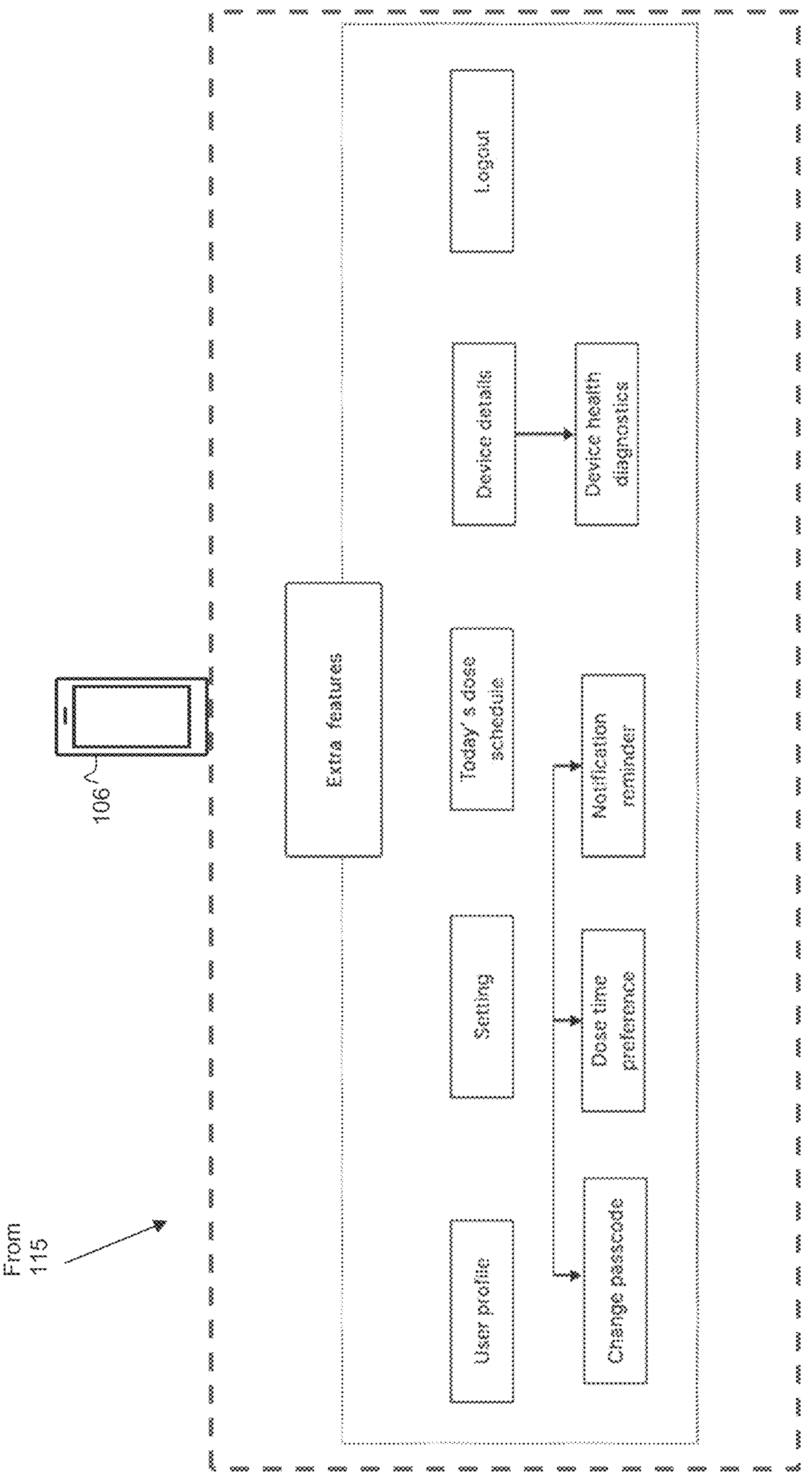

With reference to FIGS. 14A-14C, exemplary communication from the central cloud server 115 to the mobile app on the patient/caregiver device 106 are illustrated. With specific reference to FIG. 14A, on a first use of the disclosed systems and devices, the patient/caregiver may download a mobile app to their mobile device 106 and may login and/or setup an authorized account using a one-time password, such as previously created or provided by the physician or payer. If the patient/caregiver has not yet connected their mobile device to a connected medication dispenser, they may scan a QR code, or other authorization code, provided on a screen of their connected medication dispenser, such as screen 1802 of the device 1800 shown in FIG. 25.

Figure 15:
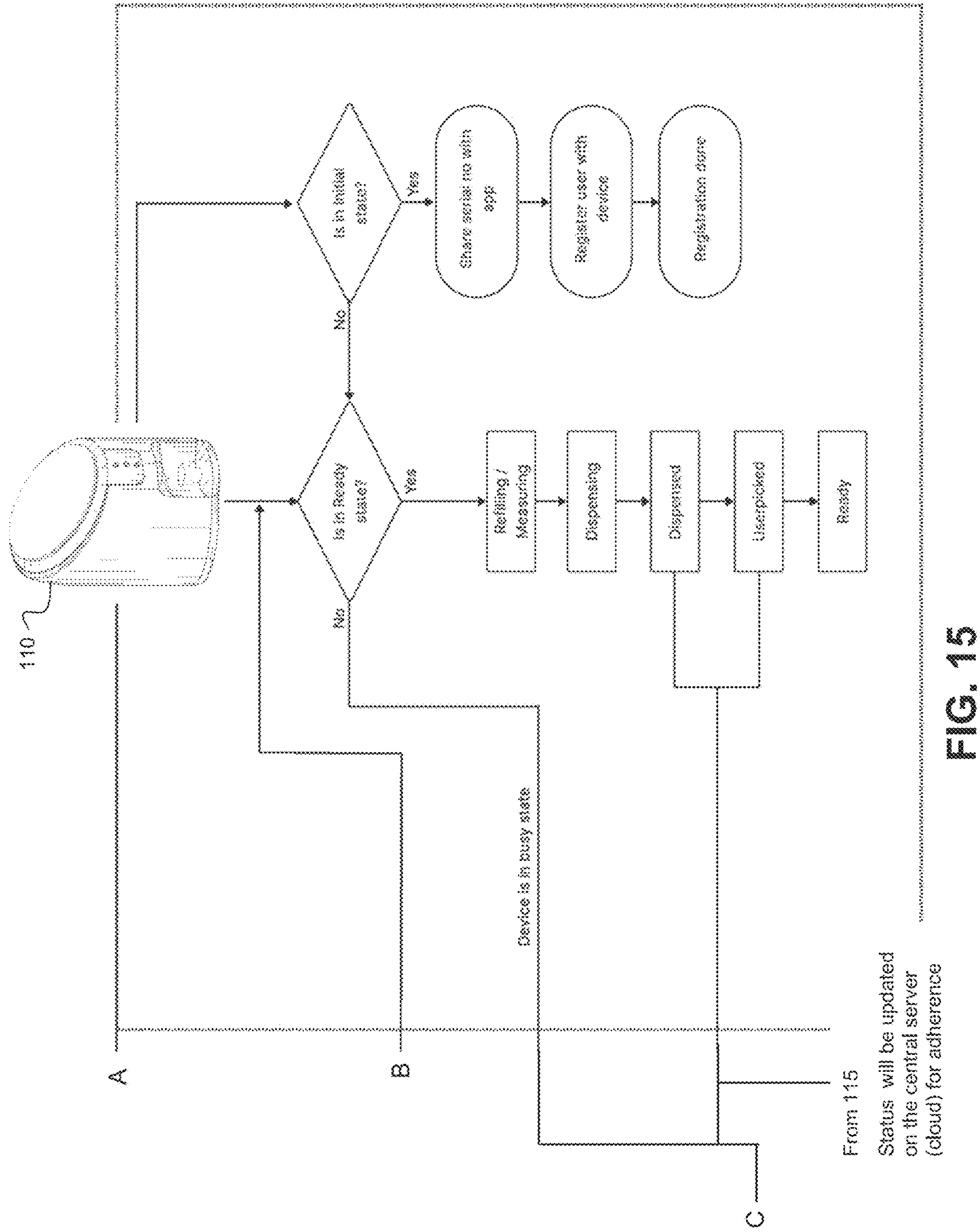
FIG. 15 depicts an exemplary process flow of a connected medication dispenser according to aspects of the present disclosure.
Figure 16:
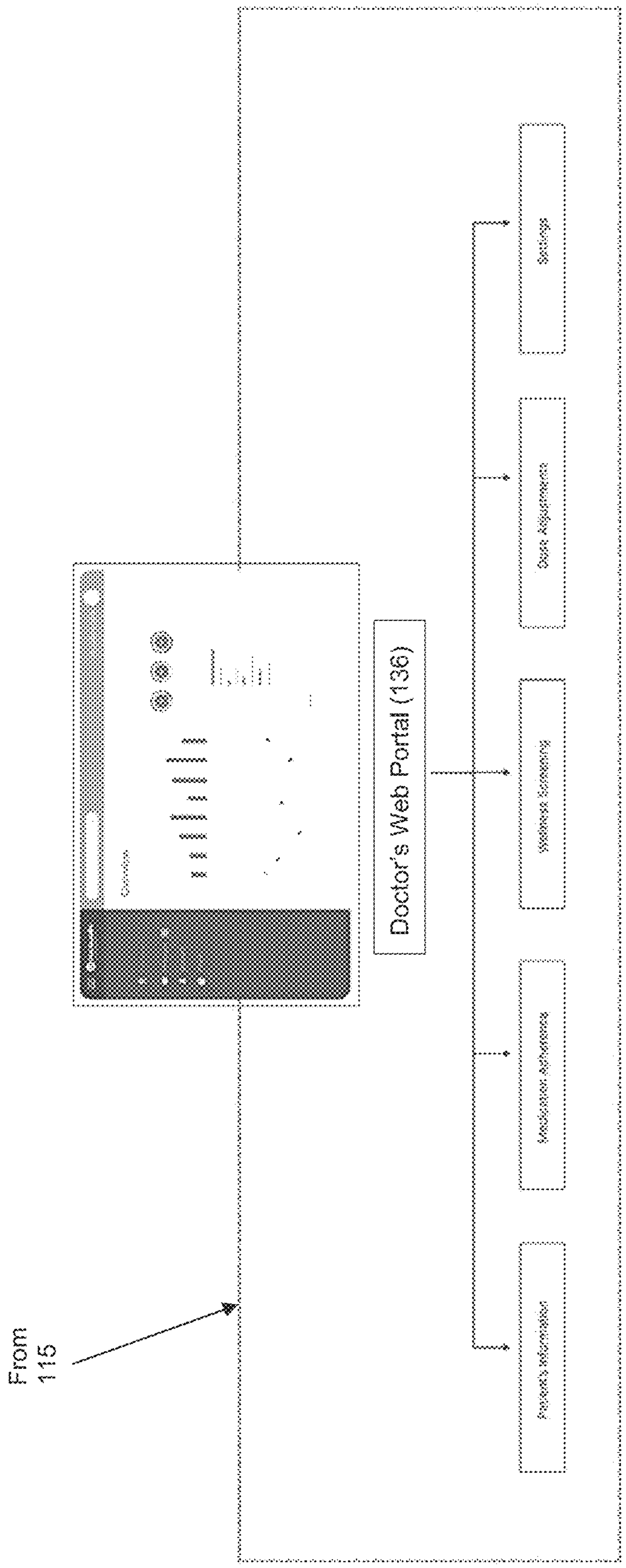
FIG. 16 depicts an exemplary process flow of a software application executing via a web portal of a providers computing device according to aspects of the present disclosure.

As shown in FIG. 15, when a dispenser 110 is first received by a patient or on first use by the patient, it may be in an initial state. In this state, the dispenser 110 may share the QR code with the user, which causes a serial number of the device to be shared, allowing the user to register their specific connected medication dispenser. Further, the QR code links the connected medication dispenser with the mobile app running on their mobile device. Alternatively, the patient/caregiver may link their connected medication device manually by entering a serial number of the device to the mobile app running on their mobile device to a patient/caregiver-centric web portal via a desktop computer. Of note, the mobile app or patient account on the web portal may also be connected to the patient information on the central cloud server 195 as described herein and thus, on connecting to a specific connected medication dispenser, the patient's medications, doses, and dose scheduling may be downloaded to the linked connected medication dispenser. For a mobile device and connected medication dispenser that have already been linked, the user may simply login to their account on the mobile app (authenticate).

As shown in FIG. 14B, the mobile app on the patient/caregiver device 106 includes a home screen that allows the patient/caregiver to receive and send various information, such as alerts regarding upcoming doses, the ability to snooze the alert for a specified amount of time (patient and/or physician authorized snooze times), and/or indicate the dose is to be skipped or has been missed. A missed dose may also be indicated to the central cloud server via other non-patient/caregiver reporting means, such as information provided by the connected pill dispenser or via the patient worn or used health monitoring devices or sensors.

Each interaction with the web app may be recorded and reported to the central cloud server 195 and/or the connected medication dispenser, either directly or indirectly through the web 115. Further, the mobile app may allow the patient/caregiver to communicate directly with the connected medication dispenser to authenticate the user identity, such as via a password, one time use code or password, biometric sensor on the mobile device and/or connected pill dispenser, and the like. Once authenticated, the mobile app may allow the user to communicate with the connected medication dispenser to request the medication be picked and/or released to a user accessible cup.

With reference to FIGS. 14B and 14C, the user may also review their scheduled doses and medications (e.g., by day, week, month), fill or refill medications in the connected medication dispenser and/or request refills from a pharmacy, such as via a pharmacy server, schedule preferred dose times, and other actions as shown. For example, the mobile app may present the patient/caregiver with a questionnaire regarding their health and wellbeing, such as sleep patterns, pain levels, eating habits, symptoms, cognition, and the like. The answers to such a questionnaire may be provided to the physician, caregiver, and/or stored in the patient's EHR. Further, based on patient permission, certain portions of the patient provided data from such questionnaires may be stored to the central cloud server.

The mobile app may allow the patient/caregiver to set/change a password, change user profile information, set type of dose reminder (type and magnitude of audible, visual, or a combination), review details of the connected medication dispenser, perform diagnostics on the connected medication dispenser, and the like.

With reference to FIG. 15, the interactions with an embodiment of the connected medication dispenser 110 are illustrated as a flowchart. As indicate, the connected medication dispenser may receive information regarding the linked patient's medications, doses, and dose schedule, as well as updates thereto from the central cloud server. The "linked patient" is the patient who has linked their connected medication dispenser to their mobile application using the QR code (or other code) provided on setup of the device and software application, and thus has linked their connected medicine to the patient's record stored in the central cloud server, which then provides communication regarding the patient between and among the pharmacy, physician. EHR, etc., as described herein.

The patient/caregiver may receive a notification on their mobile app and/or from the connected medication dispenser (audible via speaker, visual via light on device or image on the screen of the device, or any combination thereof) that a dose is scheduled and is ready to be picked up (i.e., taken). The patient/caregiver may then interact with the mobile app and/or connected medication dispenser to authenticate their identity (password, biometric, etc.) to alert the connected pill dispenser to pick the dose from various object bins within the dispenser and release the medication to a collection cup. The connected medication dispenser may include a limit switch or other means to determine when the collection cup has been removed from the dispenser, i.e., the patient/caregiver has received the dose. Specific examples of medication picking and dispensing actions are described herein below.

Information collected from the patient/local caregiver, such as patient survey responses provided to the mobile app, sensor data from worn or used health monitoring devices, medication adherence, etc. may be provided to the physician/remote caregiver for review using the physician mobile app or physician-centric web portal. Such information may assist the physician in rendering improved treatment plans and allow the physician to make real-time adjustments to the patient's treatment plan, such as increase, decrease, suspend, or add doses and medications.

In various implementations of the embodiment systems of the present disclosure, multiple services are provided. Exemplary services include an auto alert that is sent out based on collected response data that is out of range(s) set by the physician/remote caregiver for a specific patient condition. The alert may be escalated to an emergency alert sent by the patient/local caregiver devices if any emergency arises on patient's immediate health summary of compliance with 'out of expected range data' (for example, <90% compliance on intake of medicine, out of range collected response data, such as measured by a patient worn or used sensor), or any unexpected emergency health data may be sent to the physician (primary) or pharmacist (secondary) for any immediate need of response by the physician or pharmacist. Moreover, if any dose adjustment or change of medication is needed, the physician may send a new prescription to the pharmacist's attention, who can provide home delivery of the changed medication, such as in a standard prescription bottle, or a delivery tray, or specific device centric prescription bottle (see FIGS. 38A and 38B). Additionally, the pharmacist or pharmacy server may notify the physician and patient/local caregiver of such changes.

Additional exemplary services include notifications of duplicate medications. For example, when a patient visits more than one physician for their comorbid conditions they may end up getting duplicate medications prescribed, i.e., drugs with the same generic medications but of varied brands. The system of the present disclosure may determine that duplicate therapy/drugs have been prescribed for the patient and alert the patient as well as their physicians (if not already alerted by pharmacy server into the EHR). The patient's physician can review and remove duplicate medications if possible.

The disclosed system may also review prescribed medications to provide information regarding drug-drug interactions or other information regarding precautions related to drug administration. For example, when the patient is taking more than one medication, the system can periodically perform drug-drug adverse interaction checks and alert the patient and their physician if any interactions are found. This may be supplementary to any adverse interaction alerts provided by the pharmacy server to the patient/local caregiver and/or the patient's EHR. In such a case, the physician may then prescribe an alternative medication for the patient.

The disclosed system may also review the patient's EHR to check for drug allergy interactions. For example, when the patient's medication allergies are documented in the EHR, the system can perform drug-allergy adverse interaction check and alert the patient, pharmacist, and their physician if any medication that they are currently taking contains any compound to which they have a documented allergy. Adverse allergy events while takin a medication may also be input to the system, and thus the EHR for future reference.

The disclosed system may also review the patient's total intake quantity for each of their medications and alert healthcare provider if any medication exceeds a maximum tolerated dose, such as based on documented notices, patient condition, or other patient parameters (e.g., weight) to prevent drug toxicity.

This listing of services and actions of the systems and software disclosed herein is not comprehensive, as other services and software actions are possible, some of which are listed elsewhere within this disclosure.

Connected Medication Dispenser Overview

The connected medication dispensers disclosed herein include novel components and component designs. For example, the connected medication dispenser may include an electro-mechanical robotic arm for picking and placing medications (i.e., pills, doses of liquids, injectables, and the like). The connected medication dispenser may further include a specially designed removable medication tray that holds multiple medication containers (referred to as object bins) to facilitate medications of variable sizes and shapes. The removable medication tray may be equipped with an electro-mechanical locking mechanism for opening, closing, and replacing of the medication tray, and may be controlled by the pharmacist or the caregiver via a local or remote interface.

In various embodiment designs, the connected medication dispenser may be configured to store a number of diverse types of medications such as pills, doses of liquids, injectables, and the like, that may be automatically dispensed to a patient. For example, the connected medication dispenser may generate visual and audible reminders when the medications are due based on pre-programmed schedules. Further, digitally transmitted medication reminders can be given, such as via the mobile app installed on patient/local caregiver's mobile or wearable devices. The patient or caregiver may then authorize release of the medication by identifying themselves, i.e., authorizing release of the medication. Exemplary identification methods can be via any of, singly or in combination (i.e., one step or two step identification), a fingerprint scanner (biometric), retina scanner (biometric), voice identification (artificial intelligence), image identification (computer vision), password, one time code or password, or the like.

A tamper-resistant sensor may be included to monitor against events where the device or the lock on the door to the medication tray is tampered (for example, to facilitate prevention against opioid abuse or overdosing). The connected medication dispenser may further include a medication dispense chute where the medications may be dispensed for retrieval and consumption by the patient, a digital touchscreen interface to control the connected medication dispenser, which may have a configurable dashboard to allow interfaces for the patient, caregiver, and the pharmacist. For example, the screen may be configured to include a video screen for video communication between the patient, caregiver, pharmacist, and the physician. Additional components, such as a microphone and a speaker system may enable such communication, and/or may also provide voice communication for Alexa/Siri/Google voice, audio or video instructions, music, and the like.

The connected medication dispenser may include a cellular modem interface that can be configured as the primary connectivity option or as a backup connectivity option to connect with the internet in a secured fashion. Further, the connected medication dispenser may further include Bluetooth® or another form of NFC type of communication modules, which may be configured to communicate with wearable sensors to measure a patient's vital statistics, as well as to another mobile device to configure the connected medication dispenser. An interface to tether with popular voice activated systems, such as, Amazon Alexa, Apple Siri, Google Home etc. may also be included.

The connected medication dispenser also includes one or more micro-controller units (MCU) or a micro-processor units (MPU) that will facilitate central computing functions, act as controller(s) for the robotic arm, act as controller for peripherals such as an OLED/LCD touchscreen display, microphone, speaker, biometric sensors (e.g., touch sensor), and/or provide communication modules, such as a cellular module, Wi-Fi module, blue-tooth or other near-field communication modules, and the like.

A general description of the main components of the connected medication dispensers of the present disclosure are described herein below, with a more detailed description of various embodiments following.

Robotic Arm

The designs for various embodiments of the connected medication dispenser (e.g., 110 of FIGS. 17A and 17B; 1800 of FIG. 25; 1900 of FIGS. 37A and 37B) according to the present disclosure include a programmable robotic arm that is particularly designed to pick medications such as pills of varied sizes and shapes, and injectables such as syringes. The arm may be small enough to fit within an outer housing of the connected medication dispenser. In illustrative non-limiting examples, various robotic arm implementations may include a robotic suction gripper enabling picking of objects, e.g., medications or syringes, of varied size, shape, and weight from an object bin (bin containing one or a plurality of medication units). As such, exemplary systems may include a vacuum pump and feed lines connecting the pump to the suction gripper.

Figure 18:
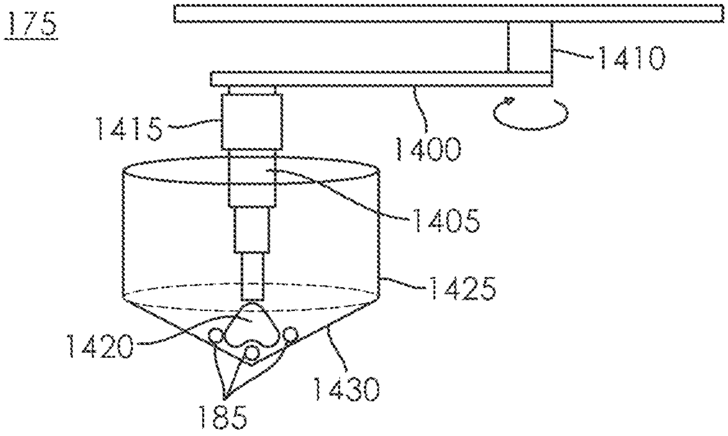
FIG. 18 depicts a perspective view of an exemplary robotic arm of a connected medication dispenser according to aspects of the present disclosure.
Figure 26:
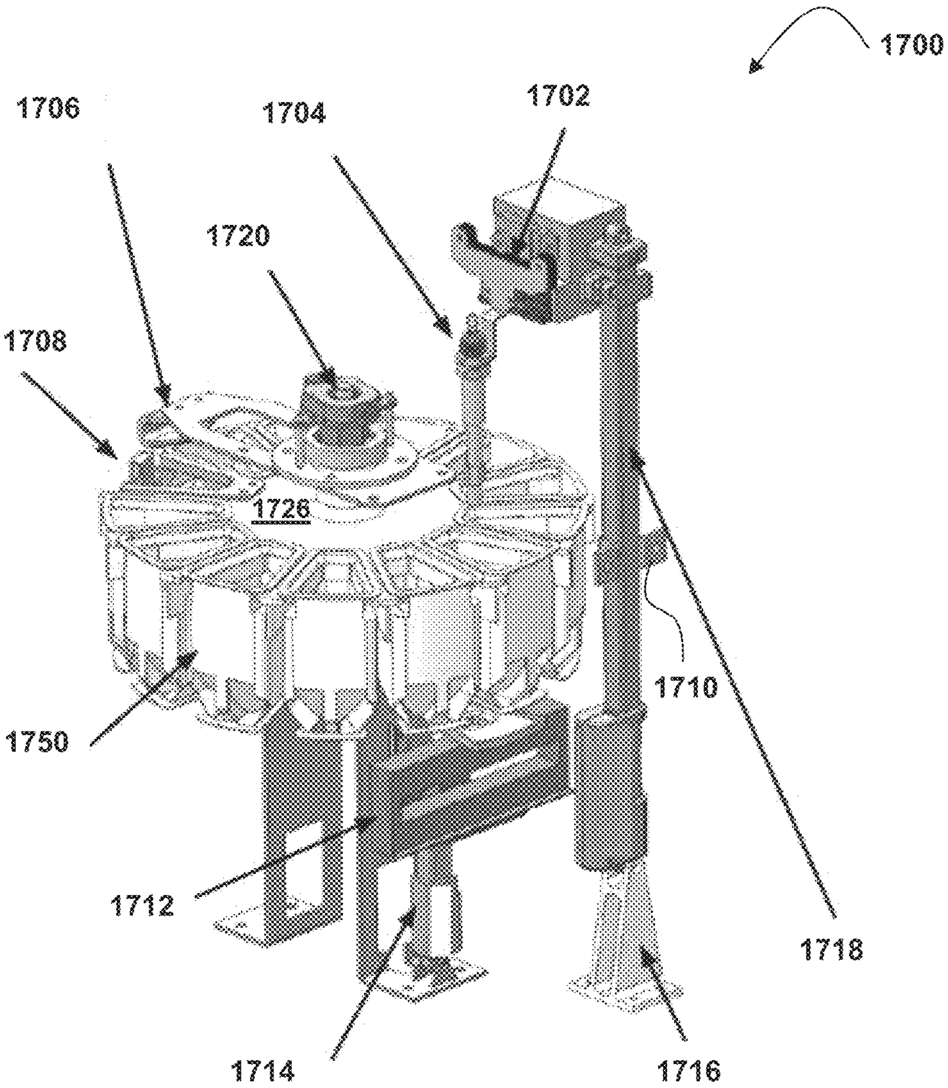
FIG. 26 depicts an exemplary connected medication dispenser showing a robotic arm and carousel holding several object bins and a dispensing bin according to the aspects of the present disclosure.

The connected medication dispenser may include a center core design (FIG. 24), where the stem or the core can rotate by substantially 360 degrees on the horizontal plane to position the robotic arm over a desired medication bin. In other implementations, the robotic arm may be positioned above a carousel and may include a pivot point (FIG. 18) allowing substantially 360 degrees on the horizontal plane to position the robotic arm over a desired medication bin. The connected medication dispenser may alternatively position the robotic arm adjacent an outer circumference of the medication container tray or carousel holding the medication bins, wherein the carousel rotates to position a desired medication bin under the robotic arm (FIGS. 18 and 26).

In some embodiment implementations, the robotic arm with the gripper may be configured to move up and down on the vertical plane such that the robotic arm can be positioned to grip medications at the upper level of a full bin, as well as move downward into the medication bin when the medications are at the bottom of the bin. Such a design works for both a replaceable medication tray (FIG. 21A) and fixed medication tray (FIGS. 21B and 26) designs. Additionally, in certain implementations, the robotic arm may be configured for transverse movement (FIG. 26) such as via a rack and pinion system to allow lateral repositioning of the suction gripper within a desired medication bin.

Medication Container Tray or Carousel and Object Bins

Medication containers and bins, also referred to herein as "object bins", are designed to facilitate simple movements of the robotic arm to facilitate picking of medications. For example, the bins may be shaped conically at the bottom such that the robotic arm can pick from the center of the bins. Due to the conical shape (FIG. 19), and in some examples, bins having tapered bottoms with shapes other than conical, the medications naturally gravitate towards the center of the bins and facilitate easy picking all medications from the bins.

In certain embodiments, the objects bins may be sized and shaped to accept larger medications such that the medication comes out one at a time from a bottom of the bins. In this case, the robotic arm picks the medications from an area below the object bin, such as a receiving tray.

Figure 21A:
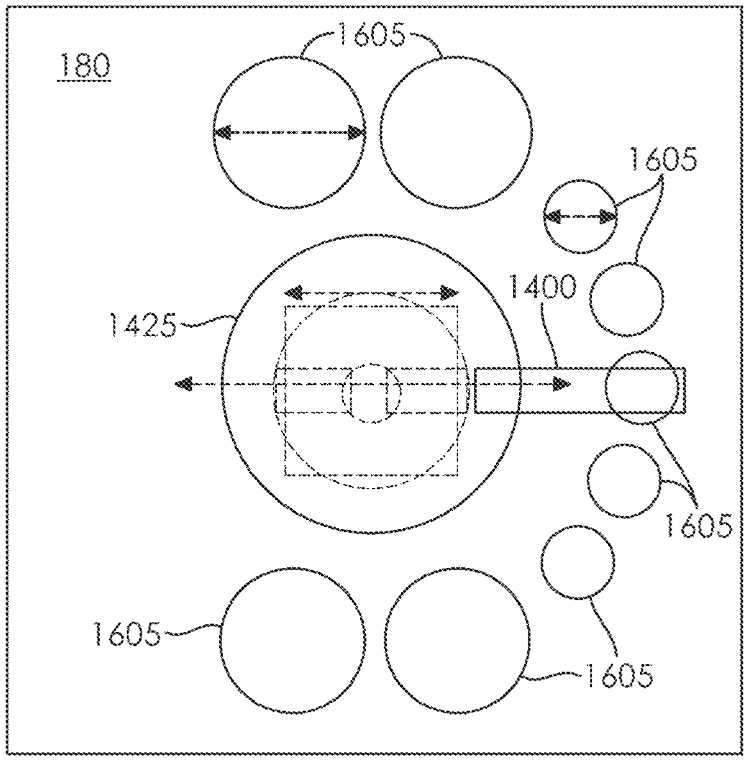
FIGS. 21A and 21B depict an exemplary platform for replaceable medication containers and fixed medication containers, respectively, according to the aspects of the present disclosure.
Figure 21B:
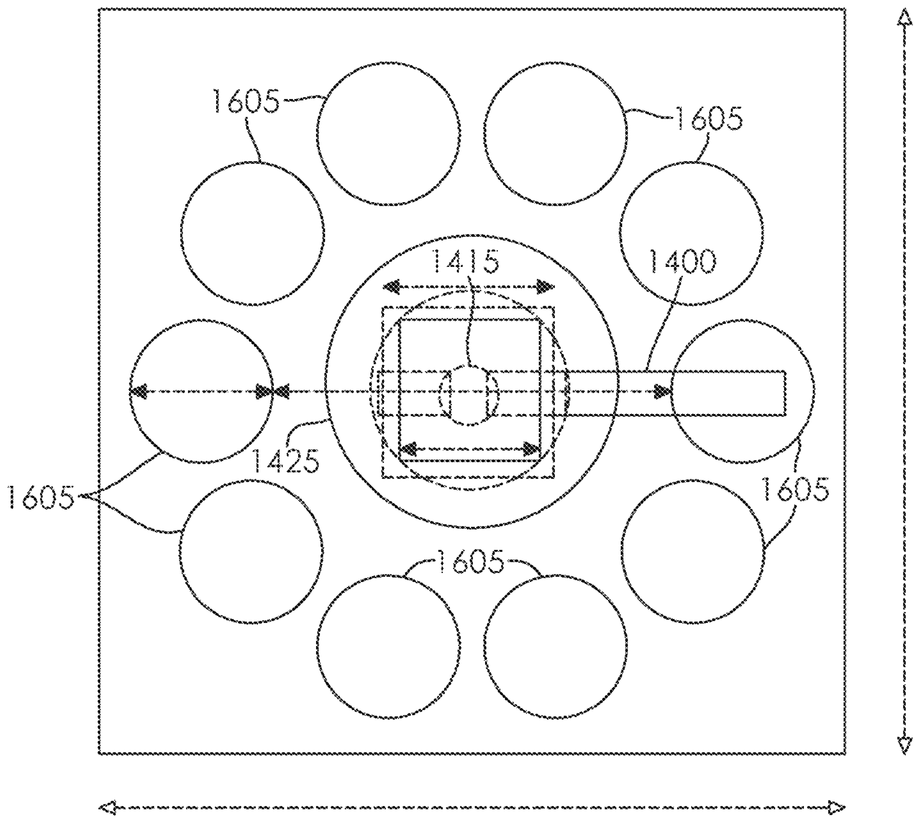

As shown in FIG. 21A, the carousel may be designed such that it can be easily ejected and replaced from the connected medication dispenser without compromising the medication bin positions for the robotic arm to operate. In the depicted example, the replaceable medication container tray wraps around the center core of the device that constitutes the stem of the robotic arm. To maximize space, the exemplary tray includes a mix of both narrow cylindrical containers for small medications, and large cylindrical containers for large medications. Alternatively, as shown in FIG. 21B, the carousel may be fixed within the device. For example, the carousel is shown as wrapping around the stem of the robotic arm. The fixed carousel may be configured to include object bins of a standard shape and size positioned concentrically about the center core of the device. In an illustrative example, the cylindrical medication containers are of the same shape and size to facilitate no restrictions on the medication size and shape the patients can choose to take. Another illustrative example of a fixed medication tray or carousel having removeable object bins is shown in FIG. 26. Of note, while each of the exemplary carousels of FIGS. 21B and 26 depict object bins having uniform shapes and sizes, the carousels can also be configured to include one or more object bins having a different shape and/or size, such as, for example, a bin configured to hold a different type or size of medication (e.g., injectables) and/or a bin configured to dispense medications from the connected medication dispenser.

Additional Components

The connected medication dispensers disclosed herein include a processor, memory comprising processor executable instruction, and a network interface that provides communication via a data network with one or more of a pharmacy server of a pharmacy, a physician server of a prescribing physician of the patient, a caregiver device, patient selected third parties, a payer server or network, and a user device of the patient. The processor executable instructions are configured to allow control of the medicine dispenser with at least one of the pharmacy server and the physician server to deliver a dose to the patient based on a prescription data, authentication of an authorized user such as the authorized user is selected from the patient or an authorized caregiver.

The connected medication dispensers disclosed herein may include a motor to cause rotation of the carousel. The connected medication dispensers may include a motor to provide rotation of the robotic arm, such as shown in FIG. 18 or FIG. 22, and/or an actuator that drives vertical motion of the suction gripper of the illustrated robotic arms, e.g., FIG. 26, and/or a rack and pinion system that includes a motor. Exemplary motors include DC motors, stepper motors, and the like. The various motors and actuators may be electrically and communicatively connected to a processor of the connected medication dispenser.

The connected medication dispensers disclosed herein may include an encoder to sense a relative or absolute position of components of the dispenser. For example, when the carousel holding the object bins is configured for axial rotation, an absolute or incremental encoder may be included to sense a position of the carousel relative to a start position under the robotic arm or a dispense position.

The robotic arm includes a suction gripper to facilitate picking of medications from the object bins. The suction provided to the gripper may be delivered from a vacuum pump positioned within the housing of the connected medication dispenser.

In certain embodiments, the connected medication dispenser comprises a weighing station positioned below the carousel and configured to weight each of the object bins. The weighing station may include a linear actuator configured for vertical movement and a load cell position on a top portion of the linear actuator and communicatively coupled to the processor and the memory. For example, the weighing station may be configured to weigh each of the object bins by (i) moving the load cell to a position under the object bin by vertical upward movement of the linear actuator so that a full weight of the object bin rests on the load cell, wherein the load cell registers the full weight of the object bin and communicates the full weight of the object bin to the processor, and (ii) moving the load cell to a position beneath the carousel and separated from the object bin by vertical movement downward of the linear actuator.

Each of the exemplary connected medication dispensers include an outer housing that in certain embodiments includes a screen for display of visual information. Such a screen may be a touch sensitive screen enabling patient/caregiver interaction with the device having a controller electrically and communicatively connected to a processor of the connected medication dispenser.

Figure 17A:
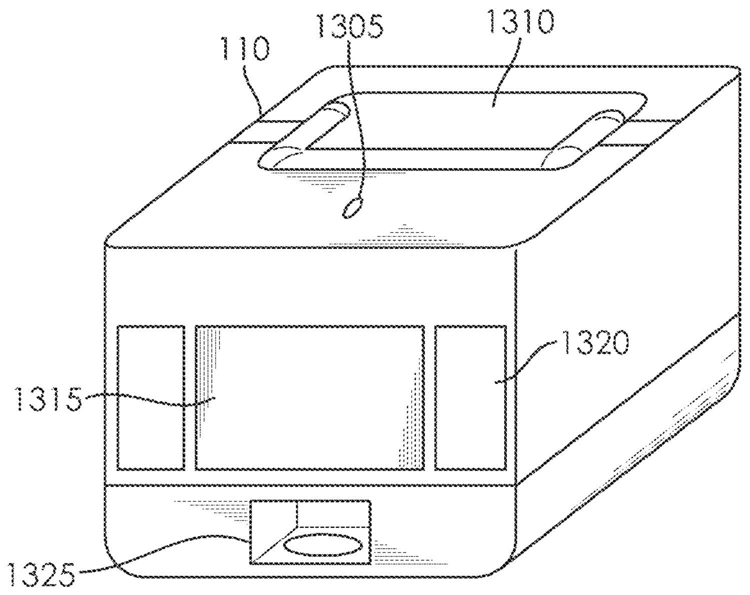
FIGS. 17A-17B depict perspective views of an exemplary connected medication dispenser according to aspects of the present disclosure.
Figure 17B:
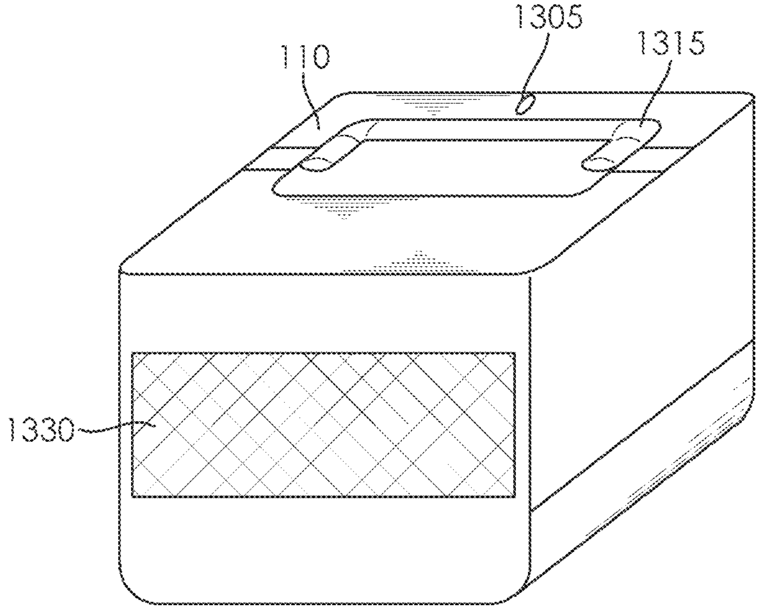

The connected medication dispensers disclosed herein may include biometric sensors configured to collected biometric verification/authentication of a patient/local caregiver. For example, as shown in FIG. 17A, the connected medication dispenser 110 may include a fingerprint scanner 1305. Additionally, or alternatively, a fingerprint scanner may be included as part of the display screen 1802 of the device shown in FIG. 25. The connected medication dispenser may include one or more cameras configured to capture images of the patient to provide authentication and/or evidence of medication adherence. For example, the cameras may capture time stamped images of patient actions after a pill collection cup is removed from the device, such as after a limit switch on a cup platform has been triggered. Such biometric components and/or cameras may include controllers that are electrically and communicatively connected to the processor of the connected medication dispenser.

The connected medication dispensers disclosed herein may include lights that illuminate a portion of the outer surface of the housing and/or speakers to provide communication with the patient/local caregiver. Additional components may include a limit switch to register when a collection cup comprising the dispensed medication is removed from the connected medication dispenser, solenoids to control mechanical components of the connected medication dispenser, such as a door lock.

The list of additional components provided herein is not exhaustive as additional components are possible and within the scope of a standard electronic device such as, for example, a battery and/or connection for a standard power source (e.g., electrical cord), additional controllers, microcontrollers, transformers, relays, fuses, and the like. for example, each of the motors and/or actuators may include a controller and motor driver that interfaces with the processor of the connected medication dispenser.

Software Systems

Software to Manage Personalized Medicine

Utilizing the web portal or the mobile app, the systems disclosed herein may be configured for the physician's office or remote caregiver to monitor the individual patients directly and regulate dosage as needed. For example, the device software may push events as frequently as necessary to the central cloud server. Exemplary events include the patient's vitals collected from wearable devices worn by the patients, such as body temperature, blood pressure, heart rate, blood oxygen level ($SPO_2$), blood sugar level, EKG, sleep pattern, exercise information, information of the programmed medicine, records of medicine compliance, and the like. Exemplary events may also include patient's vitals collected from at home devices, such as from lung congestion monitoring devices (e.g., thoracic impedance or tissue dielectric sensors), hemodynamics monitoring devices that measure pulmonary artery pressure (e.g., CardioMEMS™) or left atrial pressure, and data from defibrillators or cardiac resynchronization therapy (CRT).

The web portal may allow physician's office or remote caregiver to set patient-specific rules based on the patient's conditions and vitals. The software may alert the physician's office or remote caregiver by any of a number of methods per the preset patient-specific rules, such as visual and sound alerts on the mobile app and desktop portal based on the level of urgencies preset by the physician's office for individual patient, text message to designated phone numbers, and email messages.

Based on the nature of the alert, the physician's office or remote caregiver could take a number of different actions. For example, the physician or remote caregiver may adjust a dosage of medicine remotely and cause the connected medication dispenser to automatically dispense medications according to the adjusted dosage. The pharmacist may be notified of the change. In some scenarios, a change of dose may require a change of medications in the dispensing tray (carousel). Hence, changes in medication or medication dose may be performed by the pharmacist to patient at the direction of physician or remote caregiver. For existing medications, the pharmacist does not need to perform the change, therefore notification only will suffice. For new medications, a pharmacist may have to intervene. In response to intervention by the pharmacist, the software may identify such actions based on the change of script.

Communications between the patient and/or physician or remote caregiver to discuss conditions and decide on the next course of action may occur via video communication with the patient, such as via the display screen on the connected medication dispenser and/or on the patient's mobile or desktop device, messaging with the patient or the local caregiver using the mobile app, or phone call to the patient or the local caregiver using the web portal's inbuilt Web-RTC feature or a of the mobile app. Based on the patient's observed vitals over a pre-determined period of time, the software can make determination of the patient's health and will generate reports on a periodic basis. Physicians may have the ability to approve such reports before they get released to any other interested parties. For example, reports can be made available to the patient as well as the insurance companies to evaluate improvement or degradation of the patients' conditions. Such reports may also be stored in the patient's EHR.

The systems disclosed herein may maintain, within regulatory guideline where appropriate, such reports in a database for the purpose of 3rd party utilization and monetization.

Secured Communication Channel

The connected medication dispenser may be capable of messaging, voice, and video communications. However, per the patient, or the caregiver's preference, s/he can choose to use her/his smart phone to communicate with the eco-system of providers. For example, the voice or the video communication from the physician's office may follow patient's choice of device, such as smart phone or wearable device or the connected medication dispenser. In illustrative, non-limiting examples, the software may be capable of configuring patients' choice of devices and order for the choice of communication and creating a secured channel for communication between the providers (physicians, pharmacists) and the patients or caregiver. The system may be further capable of directing the established communication from the provider to the choice of patient's device in a prioritized fashion. For example, physician's office may be able to make a WebRTC based call to the patient's smart phone or the wearable device without having to choose one or the other, or without having to know where the call will be directed to. Such a WebRTC based call may occur based on pre-configuration and the choice made by the patient.

Medication Database and Scanning

In an illustrative, non-limiting example, the software system may be capable of maintaining a dynamic database of available medications in the market and their meta information, such as color, weight, shape, and other producer and production related information, such as batch information.

The pharmacists may be able to scan medicines that may be filled in a patient's dispenser and based on the meta information, the software may direct the pharmacist to fill the medication bins and automatically update the medication information for the particular bin. Once the meds are all scanned and filled in their respective medication bins, the software may guide the pharmacists to schedule them per the physician's prescription.

The system may allow the physician's office or remote caregiver to identify individual patients and write script(s) for that patient utilizing software applications accessible via a web portal or on a mobile device (i.e., mobile app). In some examples, when the pharmacist pulls the script and scans medication to fill in the medication bin, all he or she will have to do is to make sure the right medication bins are associated with physician's script and schedule. This process will make the pharmacist's job efficient and less error-prone.

With a search on the web portal or the mobile device, the physician, remote caregiver, or pharmacist can track any patient that may be taking medications who are listed in the software systems of the present disclosure. In such an illustrative example, any medications with safety issues or problems (for example, medications made in a particular batch of production that may be defective) can be localized to patients utilizing the presently disclosed systems. This feature may address an overall safety risk from such production issues or prevention of usage of a drug distributed in a malicious fashion, such as, for example, counterfeit drugs.

Patient Behavior Management

Managing patients' behavior towards medication adherence is an integral part of the design since reminders and automatic management of the medication are not enough to help with non-compliance of the patients. Certain techniques may be employed by the systems and devices of the present disclosure to gamify the system such that patients are nudged towards medicine compliance.

Personalized Medication Reminder

Medication reminder by the device shall constitute of techniques such as, playing favorite music when a dose is due, or having the voice of a favorite person (for example, spouse, kids, grandchildren, or a friend) announce when it is time for the meds. Patients choosing to get reminded by the mobile app can have a favorite voice reminder or a combination of a preferred sound and a visual reminder utilizing a favorite image.

Social Gamification Via Mobile App

Using various mobile app designs of the present disclosure, the patients may be able to find and follow friends and relatives to keep track of each other's health progress and medication adherence. For example, in some implementations, upon patient's choosing, the software may notify the follower via mobile app that the patient has taken his/her doses, which can turn into an emoji/sign indicating a "kudo" or "like" by the patient's followers. Similarly, a missed dose may result into an emoji/sign indicating an encouragement for compliance.

Reward System

In some implementations, every time a patient dispenses the meds, the software may record the event and assign the patient a point. A missed dose may result in a negative point. This may tally up to a weekly/monthly total target point. In an illustrative example, when an exemplary target point is met, the caregiver, the pharmacist or the physician's office can send encouraging "canned" messages or custom messages via the display of the device, by messaging through the mobile app, or by making a phone call or text. Similarly, a missed goal may be greeted by further encouragement such that the patient would try his/her best to adhere to the medication regime.

The Data

The data from the systems and connected medication dispenser, such as types of medications, refill frequencies, adherence information, patients' vital statistics, patients' medical information, and the like, may be stored on the cloud based on patients' consent, as well as, when applicable, regulatory guidelines. In some scenarios illustrative of various embodiment implementations' design or usage, the stored information may benefit the healthcare industry in many ways, for example and not limited to: assist with clinical studies; provide insights on how to improve the personalized medicine for a greater patient outcome; enable study of patient behavior and how to increase medical adherence; provide information for the insurance providers to learn about various aspects of the overall patient management such that they can work towards newer reimbursement models with a focus on keeping the healthcare cost low; and offer insights on patients' recovery and outcome based on many factors such as, medical adherence, combinations of medications taken, demographics, etc.

Exemplary Connected Medication Dispensers

One exemplary design for a connected medication dispenser useful as part of the systems disclosed herein is shown in FIGS. 17A-24. For example, FIGS. 17A-17B depict perspective views of an exemplary connected medication dispenser 110, wherein FIG. 17A provides a front perspective view illustrating a position of a medication retrieval region below a medication dispense chute 1325. In the depicted embodiment, a top of the dispenser is depicted as including and a fingerprint scanner 1305 and a carry handle 1310, which is illustrated in a closed storage configuration. In the illustrated embodiment, the connected medication dispenser front panel includes a touch-screen display 1315 and a speaker grill 1320. In the illustrated example, the dispenser chute 1325 retains the depicted medication, such as in a small cup positioned below the dispense chute. In FIG. 17B, the exemplary connected medication dispenser 110 rear perspective view includes the object tray door 1330.

Figure 19:
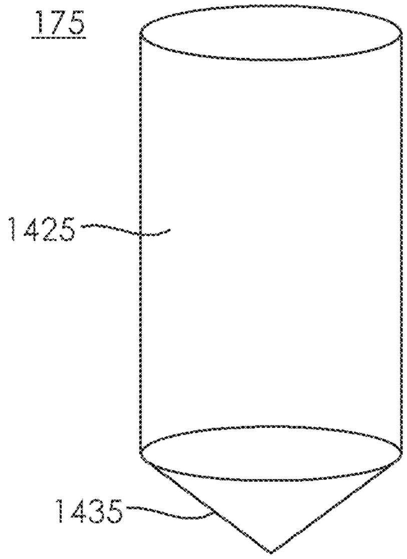
FIG. 19 depicts an exemplary object bin for use in the connected medication dispenser according to aspects of the present disclosure.

FIG. 18 depicts an exemplary robotic arm 175 of connected medication dispenser. The robotic arm 175 includes telescopic arms 1400 and 1405 configured to retract and expand. In the depicted embodiment, the exemplary robotic arm 175 is pivotally secured at the first swivel 1410 to rotate 360 degrees in thirteen positions about the depicted first axis. In the illustrated embodiment, the telescopic arm 1405 is pivotally secured at the second swivel 1415 to rotate about a second axis distal from the first axis. In the illustrated embodiment, the telescopic arm 1405 includes a suction grip 1420 configured to extend into an object bin 1425 to grab one or more payload 1430 items. In the depicted example, each payload 1430 item is a medication dose 185. In the illustrated example, each medication dose 185 may be a medication. In FIG. 19, a depicted object bin 1425 is shown to include the tapered bottom 1435. However, rounded bottoms, or a bottom region have a slope on one side, and the like are also possible and within the scope of the present disclosure.

Figure 20A:
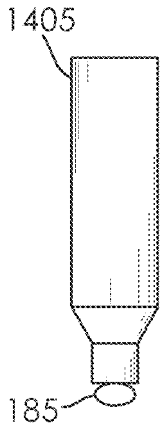
FIGS. 20A-20H depict side views of an exemplary connected medication dispenser robotic arm suction grip of the present disclosure in various illustrative operational configurations.
Figure 20B:
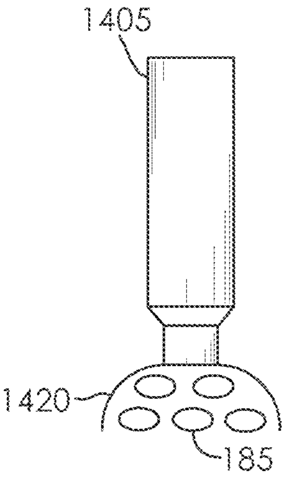
Figure 20C:
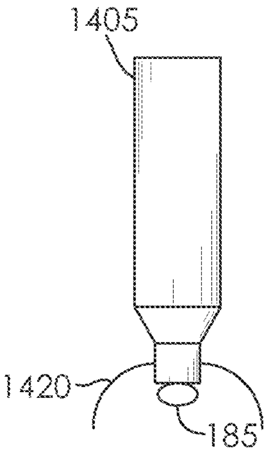
Figure 20D:
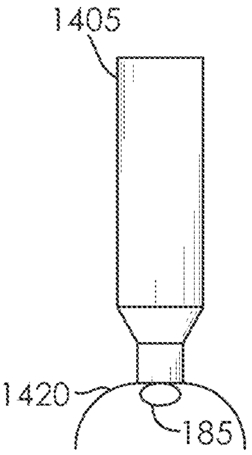
Figure 20E:
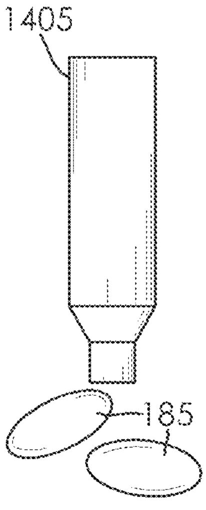
Figure 20F:
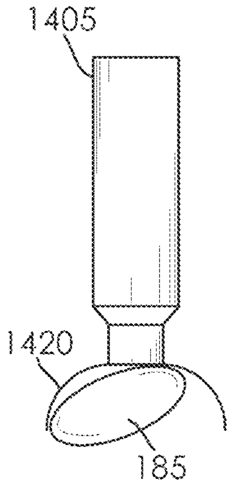
Figure 20G:
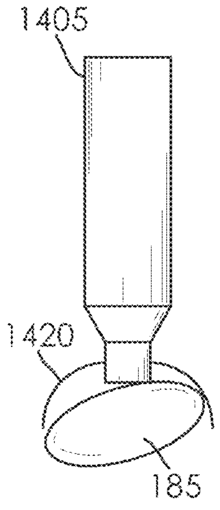
Figure 20H:
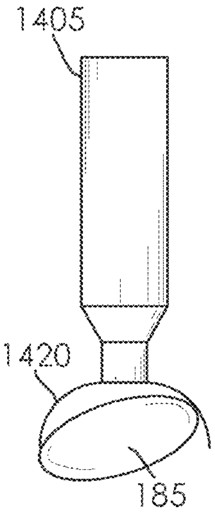

FIGS. 20A-20H depict side views of an exemplary connected medication dispenser robotic arm suction grip in various illustrative operational configurations. In FIG. 20A, the exemplary telescopic arm 1405 directly grabs the medication dose 185 with a suction nozzle configured in the telescopic arm 1405. In the illustrative operational configurations depicted by FIGS. 20B-20H, the exemplary telescopic arm 1405 includes the suction grip 1420 configured to aid grabbing by the suction nozzle configured in the telescopic arm 1405 an individual medication dose 185 having varied size or shape, presented in varied orientations.

FIG. 21A depicts an exemplary replaceable medication container design. In FIG. 21A, the exemplary replaceable medication container 180 includes the medication bins 1605 having a variety of sizes in an illustrative replaceable configuration. In the depicted embodiment, the medication container 180 is configured with the connected medication dispenser telescopic arm 1400 pivotally secured to access the object bin 1425 and the medication bins 1605.

FIG. 21B depicts an exemplary fixed medication container design. In FIG. 21B, the exemplary fixed medication container includes the medication bins 1605 in an illustrative fixed configuration. In the depicted embodiment, the medication container is configured with the connected medication dispenser telescopic arm 1400 pivotally secured at the second swivel 1415 to access the object bin 1425 and the medication bins 1605.

Figure 22A:
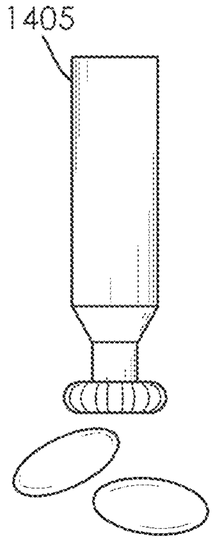
FIGS. 22A-22C together depict operational views of an exemplary vacuum suction gripper according to the aspects of the present disclosure, wherein the vacuum suction gripper includes a tube-shaped rubber skirt configured around the suction nozzle.
Figure 22B:
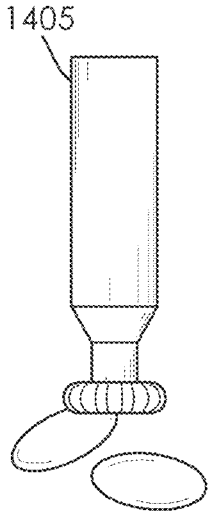
Figure 22C:
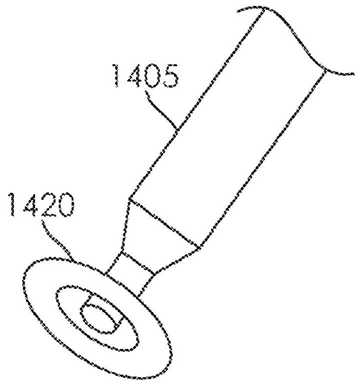

FIGS. 22A-22C together depict operational views of an exemplary vacuum suction gripper including a tube-shaped rubber skirt configured around the suction nozzle. In the embodiment depicted by FIGS. 22A-22C, the tube-shaped rubber skirt configured around the suction nozzle is adapted to create a suction vacuum around the edges of the elongated medications. In an illustrative example, the inner surface curvature of the tube-shaped skirt urges the elongated medications toward the gripper based on rotationally aligning the medications with the gripper suction nozzle force, thereby enhancing the ability of the gripper to grip medications of diverse sizes and shapes. In FIG. 22A, the exemplary gripper configured in the telescopic arm 1405 is depicted approaching the medication. In FIG. 22B, the gripper slightly pushes against the medication with the tube and creates a vacuum suction to grip the medication. In FIG. 22C, the bottom of the tube skirt 1420 is depicted after release of the medication into a dispensing chute.

Figure 23A:
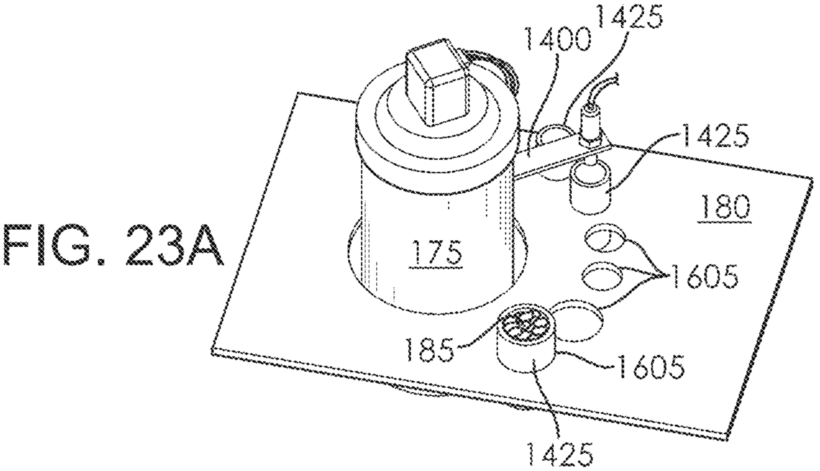
Figure 23B:
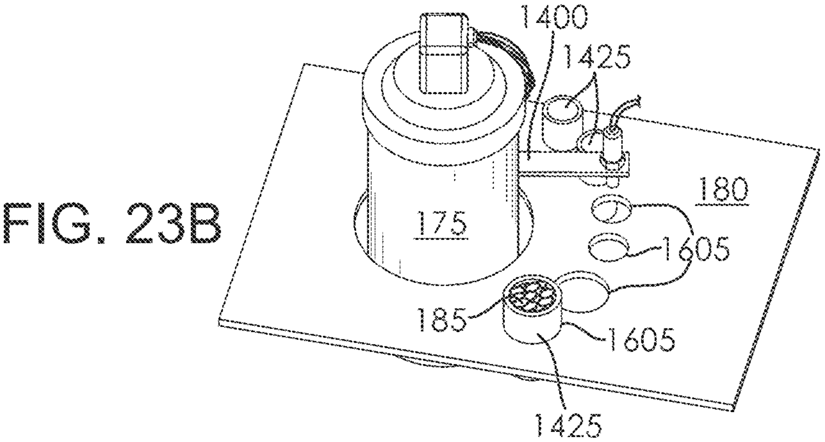
Figure 22C:
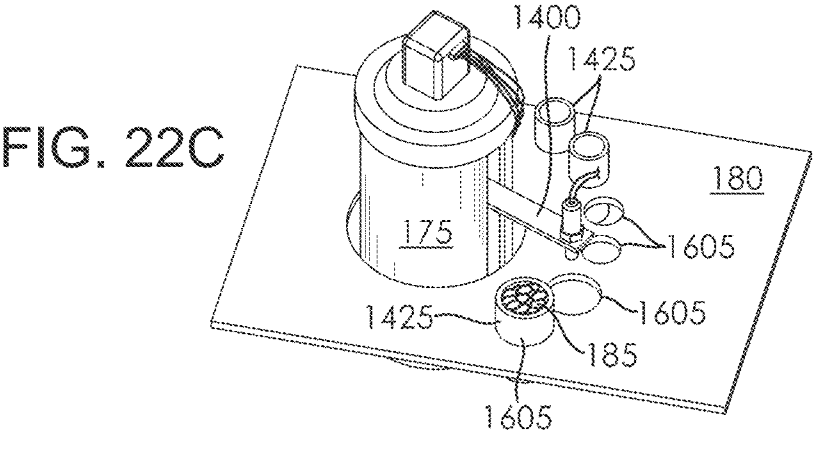
Figure 23D:
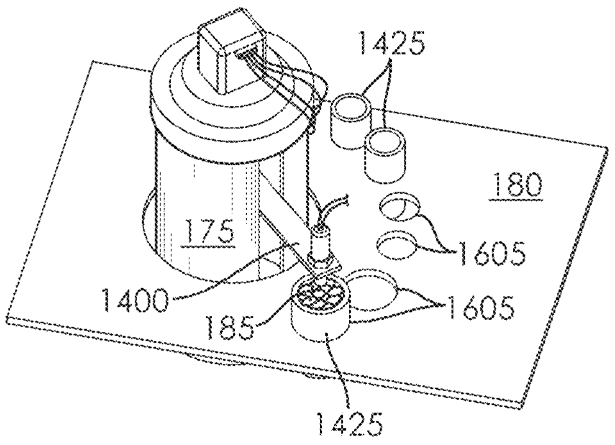
Figure 22E:
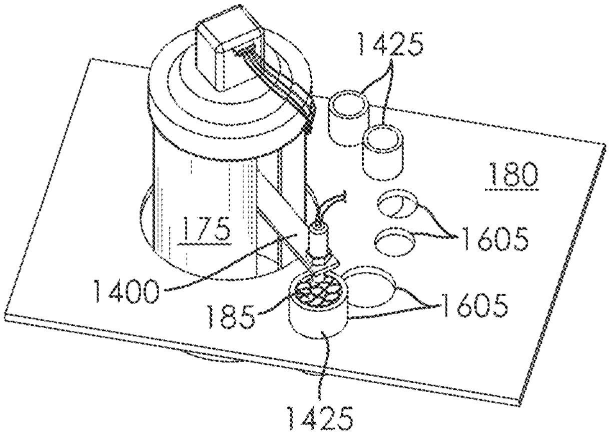
Figure 23F:
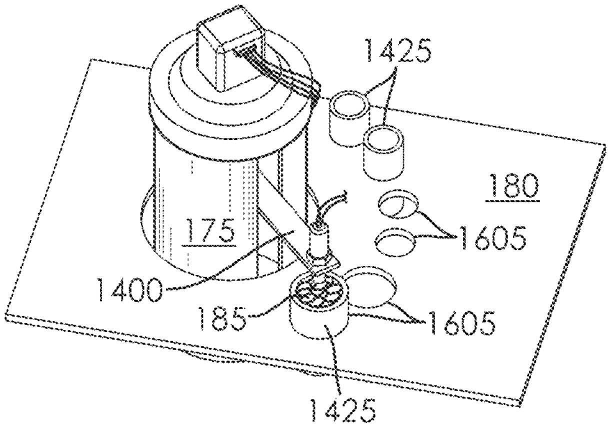
Figure 23G:
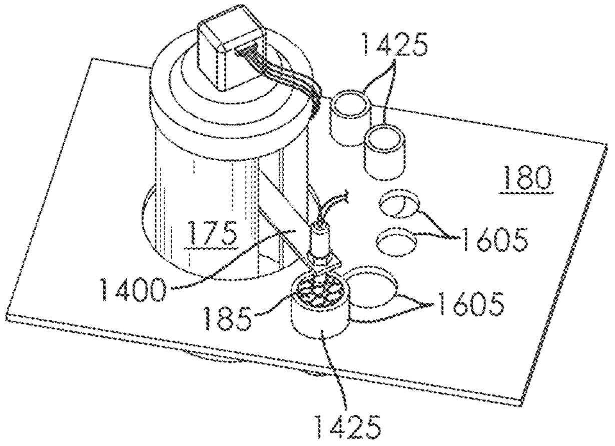
Figure 23H:
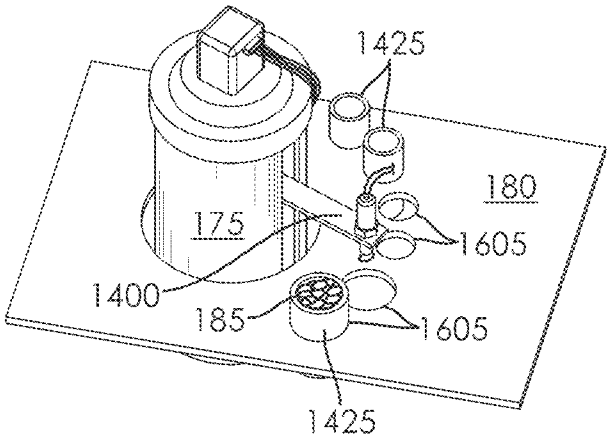
Figure 23I:
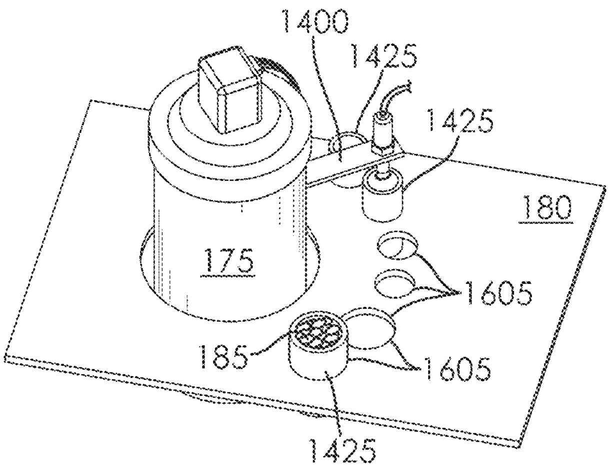

FIGS. 23A-23K together depict operational top perspective views of an exemplary connected medication dispenser robotic arm dispensing a medication dose, based on gripping the medication retained by an embodiment medication container and releasing the dose into an exemplary dispensing chute. In FIG. 23A, the exemplary connected medication dispenser is depicted in an illustrative medication dose dispensing starting mode with the robotic arm 175 including the telescopic arm 1400 disposed in a first position distal from the medication dose 185 retained in the exemplary object bin 1425 by the medication bin 1605. In FIG. 23B, the exemplary connected medication dispenser robotic arm 175 has begun to move toward the medication dose 185. In FIG. 23C, the exemplary connected medication dispenser robotic arm 175 continues in motion to the medication dose 185. In FIG. 23D, the exemplary connected medication dispenser robotic arm 175 motion stops when the telescopic arm 1400 reaches the medication dose 185. In FIG. 23E, the connected medication dispenser robotic arm 175 descends to position the gripper and suction nozzle for access to the medication dose 185. In FIG. 23F, the connected medication dispenser robotic arm 175 gripper securely grabs the medication dose 185 based on vacuum suction from the nozzle. In FIG. 23G, the connected medication dispenser robotic arm 175 ascends to position the gripper to transport the medication dose 185 to a dispensing chute. In FIG. 23H, the exemplary connected medication dispenser robotic arm 175 gripping the medication dose 185 has begun to move toward the dispensing chute. In FIG. 23I, the exemplary connected medication dispenser robotic arm 175 gripping the medication dose 185 continues in motion toward the dispensing chute. In FIG. 23J, the exemplary connected medication dispenser robotic arm 175 gripping the medication dose 185 has reached the dispensing chute in a second illustrative dispensing position distal from the medication dose 185 retained by the exemplary medication container 180. In FIG. 23K, the exemplary connected medication dispenser robotic arm 175 releases the medication dose 185 into the dispensing chute.

FIG. 24 depicts a top perspective view of an exemplary center core robotic arm design. In the embodiment depicted by FIG. 24, the connected medication dispenser 110 includes a center core robotic arm 175 design, wherein the stem or the core can move by substantially 360 degrees on the horizontal plane to position the robotic arm 175 for access to the desired object bin 1425. Each object bin may be retained by a medication bin 1605, depicted at least by FIGS. 16 and 19A-19K. In the illustrated embodiment, the robotic arm 175 including the telescopic arm 1400 and the telescopic arm 1405 configured with the gripper is configured to move up and down on the vertical plane such that the robotic arm 175 can be positioned to grip medications at the upper level of a full object bin 1425, as well as, to go down into the object bin 1425 when any medication may be at the bottom of the bin. The depicted design is applicable with replaceable medication tray (FIG. 21A) and fixed medication tray (FIG. 21B) designs, and other medication tray designs. In the center-core robotic arm design example depicted by FIG. 24, the vertical movement of the arm is controlled by a screw mechanism at the center core, instead of the telescopic concept depicted by FIG. 18. In the depicted center-core design illustrated by FIG. 24, the telescopic arm 1400 may move vertically as well as in a circular fashion on the horizontal plane for positioning on the desired medication vial/bin. Further, the picking arm will have flexibility to position the picking grip to pick medications situated in various angles within the vials. In various implementations, a suction gripper as depicted, for example, by FIG. 15A may be used to grip and pick medications from the vials.

Another exemplary embodiment of a connected medication dispenser 1800 is shown in FIGS. 25-36B. With specific reference to FIG. 25, the connected medication dispenser 1800 is shown as including a display screen 1802 on an outer top surface of a housing. The display screen 1802 may provide visual cues directing the patient/local caregiver through various steps in the medication adherence process, such as logging in, device setup, loading and reloading object bins, and the like. The display screen 1802 may be a touchscreen that may allow patient/caregiver entry of data and may be configured to collect biometric authentication data such as a fingerprint scan.

Figure 25:
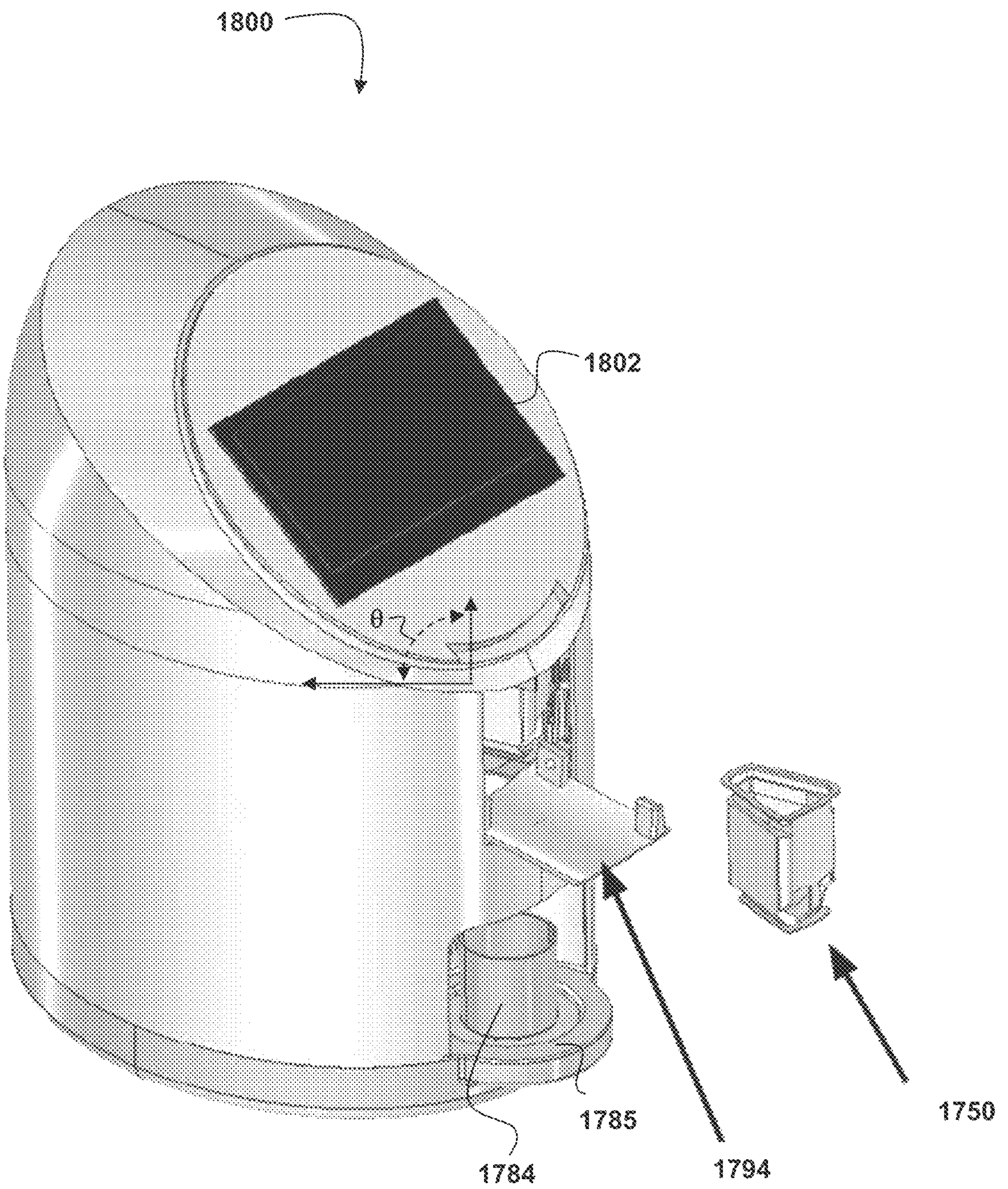
FIG. 25 depicts a perspective view of an exemplary connected medication dispenser according to aspects of the present disclosure, where the refill gate in shown in the open position to accept an object bin to the carousel.

The display screen 1802 may be positioned on a top surface of the connected medication dispenser 1800 and may be oriented at an angle q relative to the horizon that provides easy viewing by a patient/caregiver when the connected medication dispenser 1800 is positioned on a countertop. Exemplary angles q include 10° to 75° with respect to a horizontal surface of the countertop, such as 10° to 60°, or 10° to 45°, or 15° to 30°. The connected medication dispenser 1800 may further include speakers and lights to provide audible and visual reminders, alerts, or to direct actions of the patient/caregiver. Also shown in FIG. 25 are a cup platform 1785 having a medication collecting cup 1784 positioned thereon, and an object bin 1750 ready to be accepted into the connected medication dispenser 1800 through the open refill gate 1794.

A top region of the connected medication dispenser 1800 may further include one or more cameras positioned to capture images of the patient/local caregiver interacting with the device, such as for visual (biometric) identification of the patient/local caregiver and/or confirmation of medication adherence by the patient. That is, the cameras may collect time stamped images or video that may be analyzed through computer vision and/or artificial intelligence algorithms to correlate with or match to image data representative of various patient activity states such as limb positions, hand positions, postures, gestures, or reflexes, associated with medication adherence. The cameras may also provide network enabled video feed, such as video conferencing between the patient/caregiver and a physician, pharmacy, etc.

With reference to FIG. 26, the connected medication dispenser 1800 includes a robotic arm 1700 attached to an inner surface of a housing of the dispenser, such as attached to a floor of the inner surface of the housing via a bracket 1716. The robotic arm 1700 includes a linear actuator that extends and retracts an actuator arm 1718 vertically, i.e., up or down within the housing, to position a vacuum probe 1704 within an object bin 1750, such as to pick a medication. The actuator arm 1718 may be stabilized by attachment to an inner sidewall of the housing, such a via a clip 1710.

Also shown in FIG. 26 is a carousel 1726 configured to support a plurality of object bins 1750 and one dispense bin 1708, a weight station having a linear actuator 1714 that supports a load cell 1712, and a cam arrangement attached to an end of a support arm 1706 useful to assist in releasing picked medications to a medication collecting cup 1784 for patient retrieval.

Figure 27A:
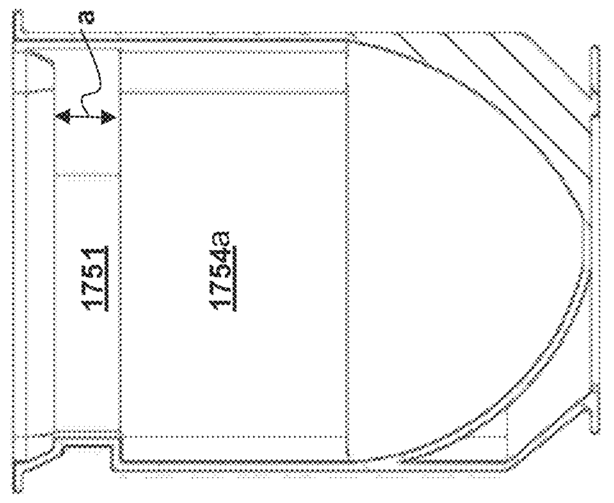
FIGS. 27A-27C depicts various views of an object bin according to the aspects of the present disclosure.
Figure 27B:
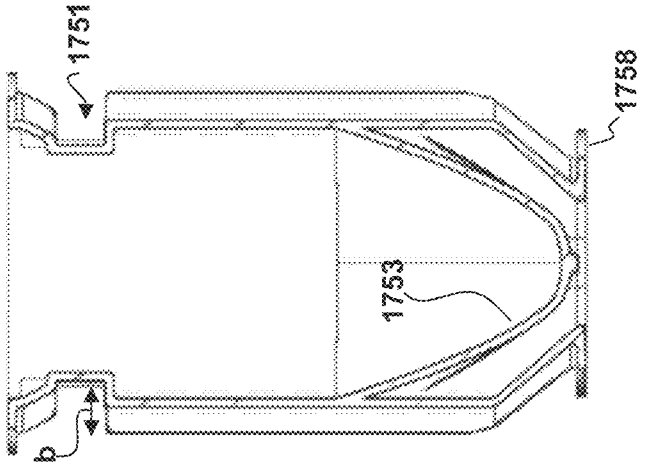
Figure 27C:
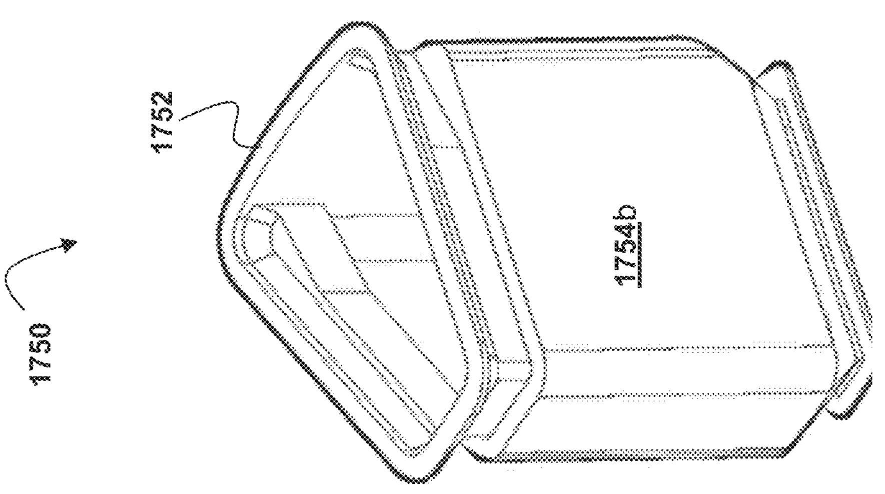
Figure 34A:
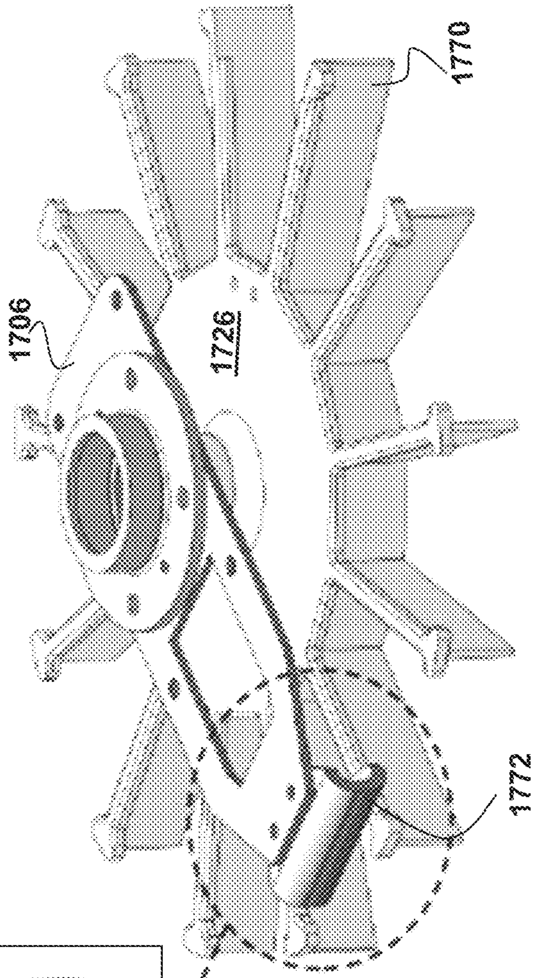
FIG. 34A depicts a bin support frame of the carousel and a fixed cam positioned above the carousel according to aspects of the present disclosure.
Figure 34B:
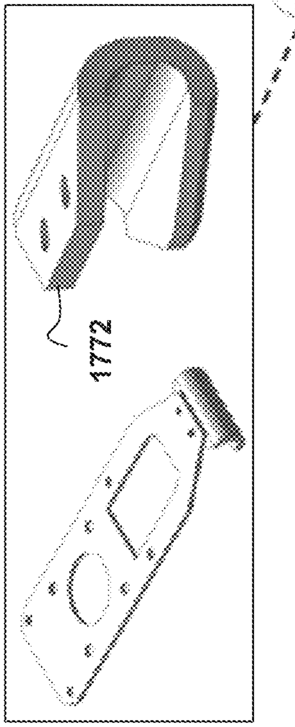
FIG. 34B depicts components of the fixed cam shown in FIG. 34A.
Figure 34C:
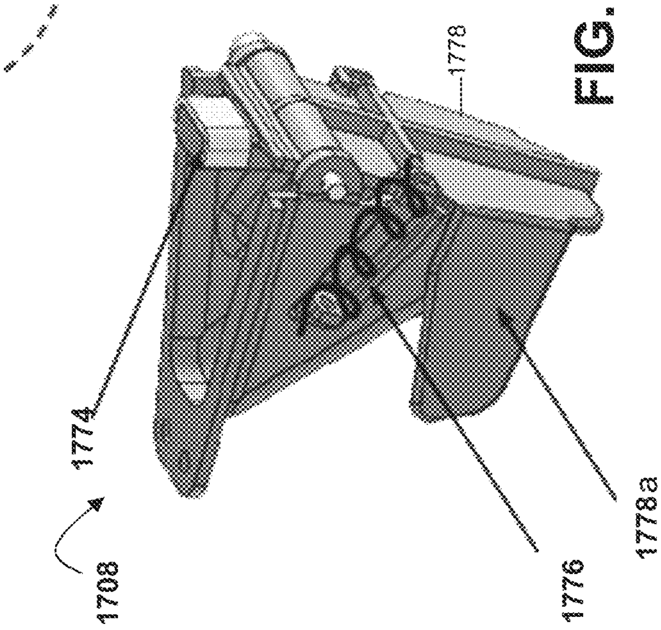
FIG. 34C depicts a dispensing bin according to aspects of the present disclosure, wherein the dispense bin includes a door having a follower tab configured to interact with the fixed cam shown in FIG. 34A to open the door, releasing medicine contained in the dispense bin.

The object bins 1750 are shown in more detail in FIGS. 27A-27C, which depict side and rear cross-sectional views (FIGS. 27A and 27B), and a perspective view (FIG. 27C). In the illustrated embodiment, the object bins 1750 include an inner surface 1754*a* that slopes inward 1753 toward a bottom surface of the bin such that medications positioned therein will naturally fall to the bottom of the object bin 1750. Moreover, the object bin 1750 includes an open top defined by a circumferential rim 1752, below which is an indent or recess 1751 on an outer surface 1754*b* of the bin on at least two sides, such as the left and right sides of the bin. The recess is configured to provide connection with the carousel, even when rotated, i.e., remains secured on the carousel during the centrifugal force of carousel rotation, such as shown and described with reference to FIGS. 34A and 35. Specifically, the recess 1751 has a depth 13' and height 'a' dimensioned to accept adjacent arms 1770 of the carousel 1726 on either side of the object bin 1750 (FIG. 34A). Further, the height 'a' of the recess 1751 allows vertical movement of the object bin, such as when lifted by the weight station 1748 (FIG. 31A and discussion below), without detachment of the object bin 1750 from the carousel 1726.

Figure 31A:
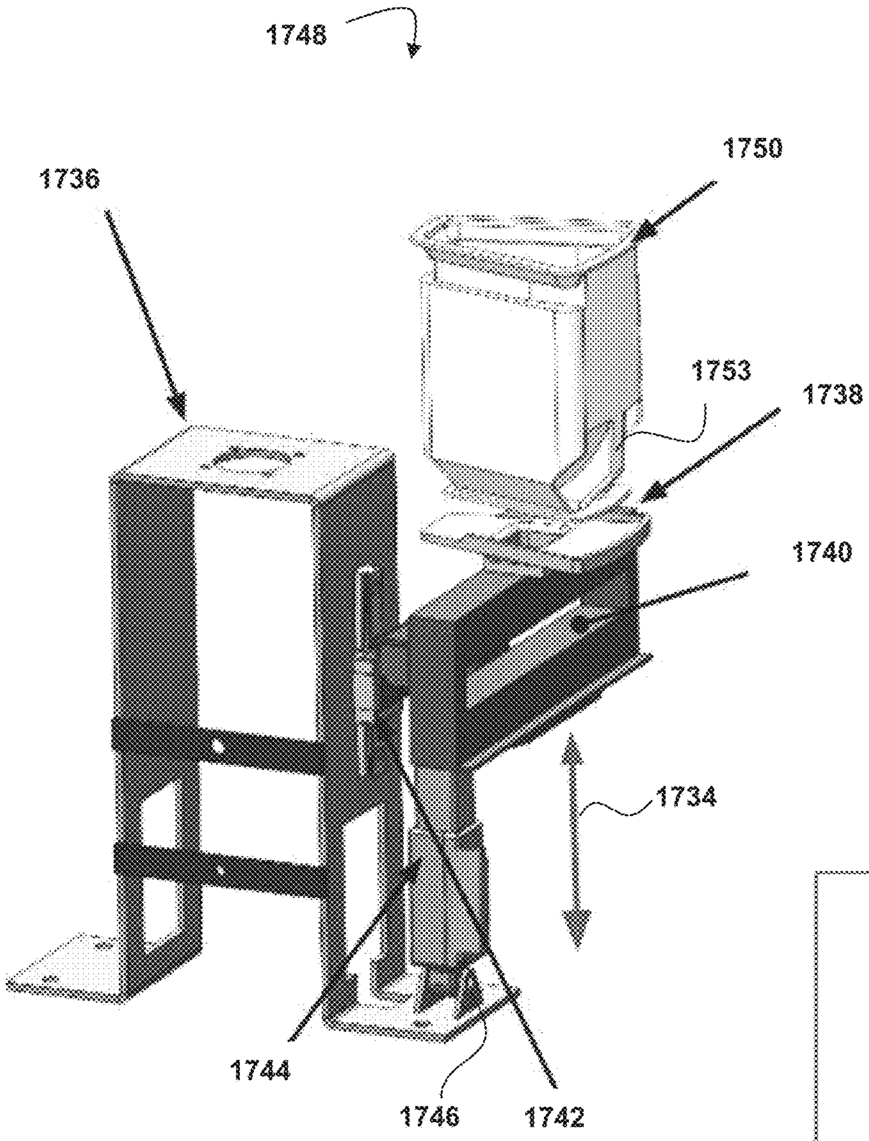
FIG. 31A depicts a perspective view of the weighing station according to aspects of the present disclosure, wherein an actuation, load cell, and bin platform are shown below an object bin.

The object bins may include a "handle" on a rear side thereof (1753 of FIG. 31A). The handle may be sized and shaped to provide a grasp point for the patient/local caregiver when retrieving of replacing the object bin from or to the connected medication dispenser (FIG. 25). The object bins may be configured to hold at least a one-month supply of a medication. For example, in an exemplary embodiment, the object bin may be sized to contain 30 pills having a length of 22 mm. Should a patient dose include multiple of the same pill, or the patient wish to include more than a one-month supply in the dispenser, one than one object bin may be used to contain a single medication.

Each object bin 1750 may include a code or ID on an outer surface of the bin that may be read by a sensor of the connected medication dispenser. When a medication is loaded to an object bin, the connected pill dispenser will link the identity of the medication to the object bin code. The connected medication dispenser may know a unit weight of the loaded medication, such as from a database of medication information, manual input, or via weighing the object bin before and after loading the medication using the weight station and estimating an average unit weight based on the number of units loaded in the object bin. This information may be stored in the memory of the connected medication dispenser and may be shared with the central cloud server. In general, the connected medication dispenser will weight each object bin after refill to record a starting weight of the object bin and an estimated average unit weight of the medication.

Figure 28:
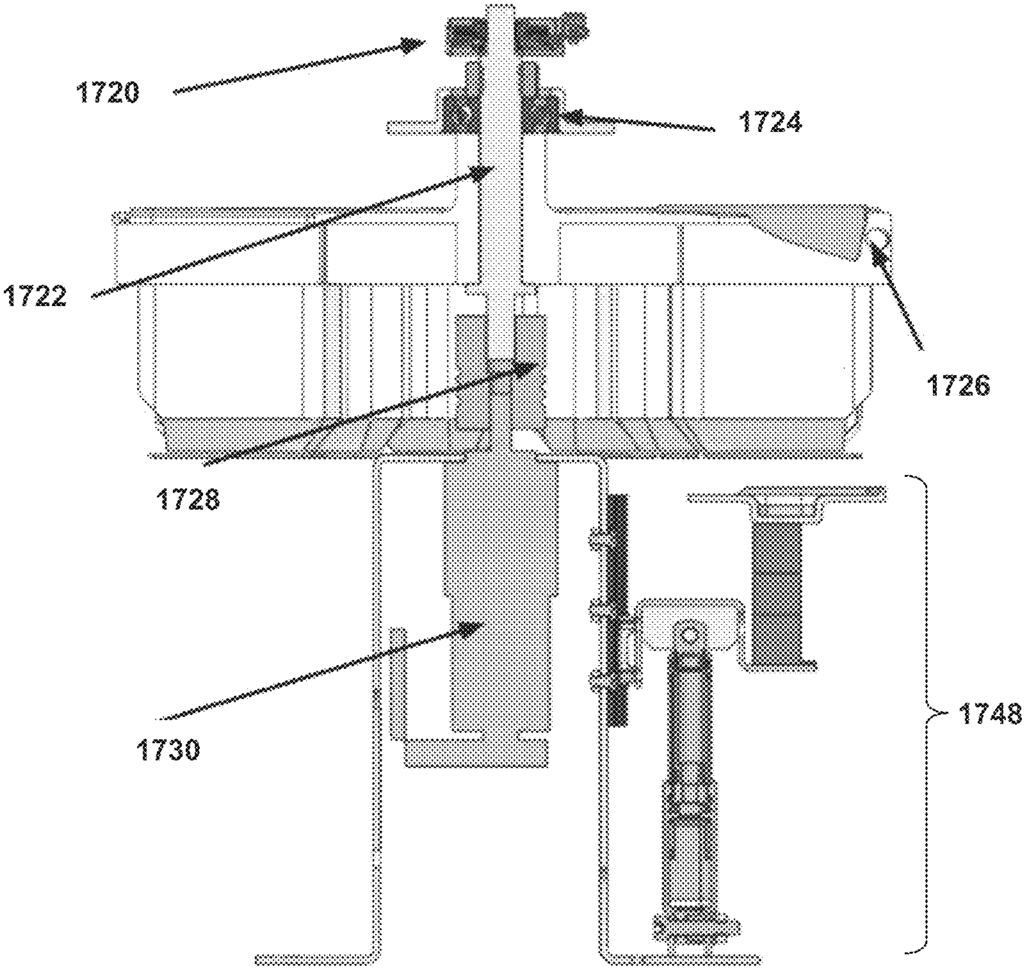
FIG. 28 depicts a cross-sectional view of an exemplary connected medication dispenser showing a central shaft supporting a carousel holding several object bins, a motor to drive rotation of the carousel, and a weighing station according to aspects of the present disclosure.

FIG. 28 illustrates a cross sectional view of the carousel 1726 supported on a coupling 1728 attached to the shaft of a motor 1730. Axial rotation of the shaft, as driven by the motor, is linearly translated to provide an axial rotation of the carousel. The motor may be a DC motor that provides 360-degree rotation of the carousel 1726 in either direction. Also shown is a central spindle 1722 that may support an absolute encoder 1720 near a top end thereof. Also shown in FIG. 28 is a position of the weight station 1748.

Figure 29:
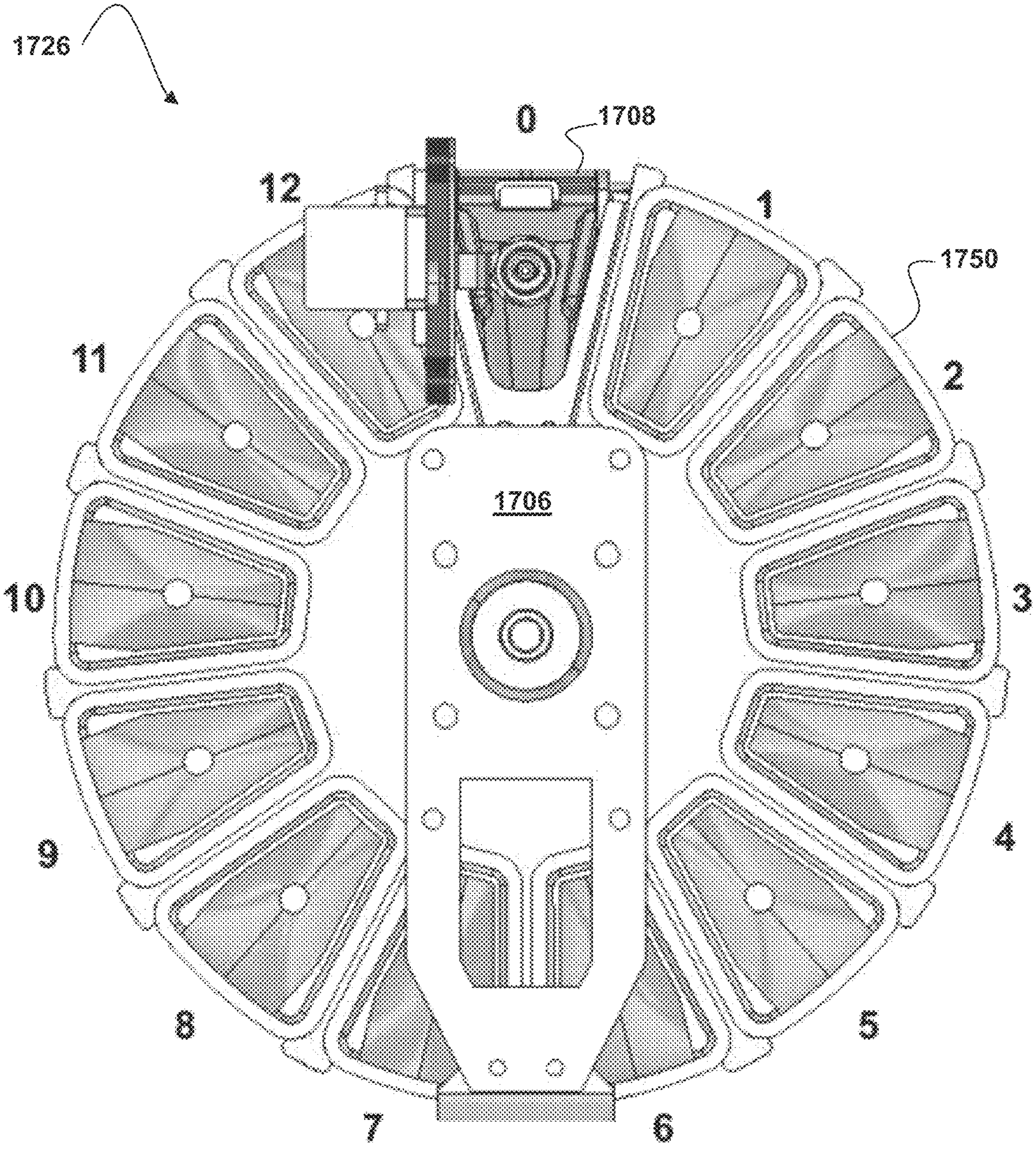
FIGS. 29, 30A, and 30B depict an exemplary arrangement of object bins 1-12 and a dispensing bin 0 in the carousel according to aspects of the present disclosure, wherein the arrows in FIGS. 30A and 30B illustrate the bidirectional rotation of the carousel.

FIG. 29 depicts a top view of the carousel 1726 having twelve object bins 1750 positioned therein, and one dispense bin 1708. The object bins and dispense bin may be of comparable size and shape and may thus be positioned within the carousel equidistant from a central axis of the carousel. For example, in an embodiment of the carousel having thirteen openings configured to contain twelve object bins and one dispense bin, each opening may occupy a sector comprising one thirteenth, i.e., 27.69° of the 360° circumference, of the carousel. The dispense bin is shown at a zero position directly under the robotic arm and directly opposite a dispense position (between bin 6 and 7). At the dispense position is a cam arrangement 1772 at an end of a support arm 1706. When a medication is to be picked from an object bin, the carousel will rotate to position the proper object bin, i.e., any one of the bins 1 through 12, directly under the robotic arm at a start position. The linear actuator of the robotic arm will move vertically downward to position the suction gripper within the object bin to pick a medication (or other medication contained within the object bin, e.g., syringe, etc.) and vertically upward thereafter. The motor will then rotate the carousel to position the dispense bin, shown at the zero position in FIG. 29, directly under the robotic arm, i.e., the start position, so that the picked medication may be released therein.

This process will continue until all medications for a particular dose (i.e., any number of different medications and or medications may be part of a "dose") are picked from respective object bins 1750 and deposited into the dispense bin 1708. Of note, and with reference to FIGS. 34A-C, positioned directly over the carousel is a cam arrangement 1772 supported by an arm 1706. The dispense bin 1708 includes a follower tab 1774 configured to interact with the cam 1772 when the dispense bin is rotated to the dispense position, i.e., directly opposite the start position and under the arm 1706. The cam 1772 pushes the follower 1774 on the dispense bin 1708 downward, thus providing a counterforce to the spring 1776 that holds the door 1778 on the dispense bin 1708 closed. As such, during picking of a dose, the carousel is rotated to pick medications from the various object bins and deposit each picked medication in the dispense bin in both the forward and reverse directions so that the dispense bin does not pass under the cam arrangement until the entire dose is contained in the dispense bin.

Of note, while the dispense bin 1708 is shown as having substantially the same size as the object bins 1750, other arrangements are possible and within the scope of the present disclosure. Further, the shape of the dispense bin 1708 may include a slanted rather than conical inner bottom surface so that the dose contained therein may be encouraged to exit the door 1778 when opened. According to certain implementations, the door 1778 may include portions 1778*a* that extend from opposite lateral sides thereof so that upon opening of the door, the dose exits substantially downward into the hopper and the pill collecting cup (1780 and 1784 of FIG. 35, respectively).

Figure 30A:
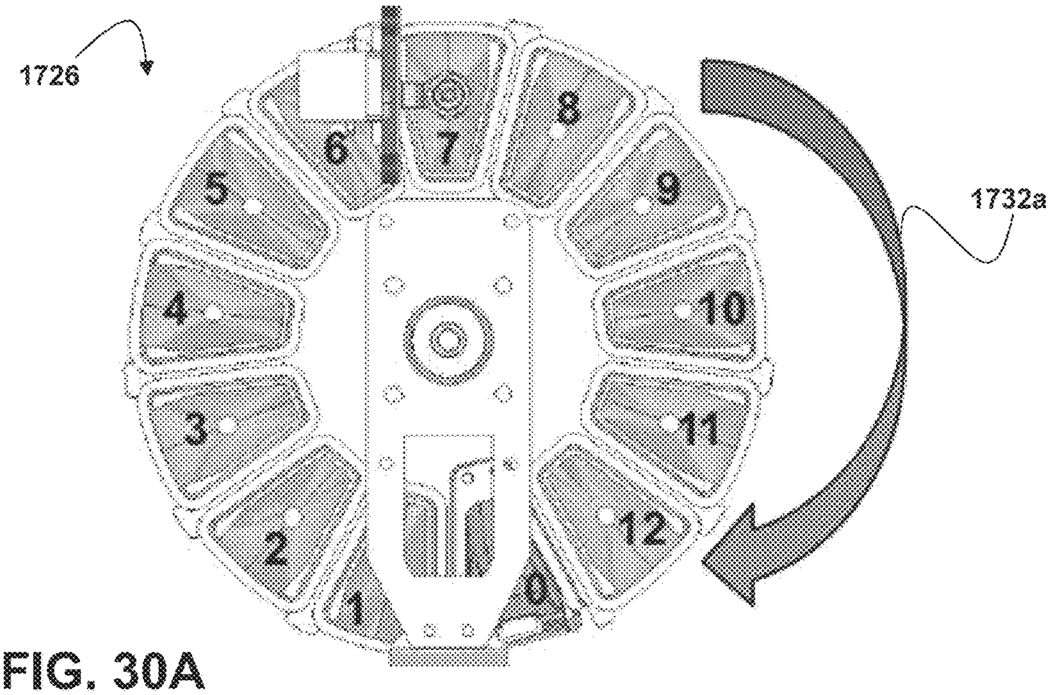
Figure 30B:
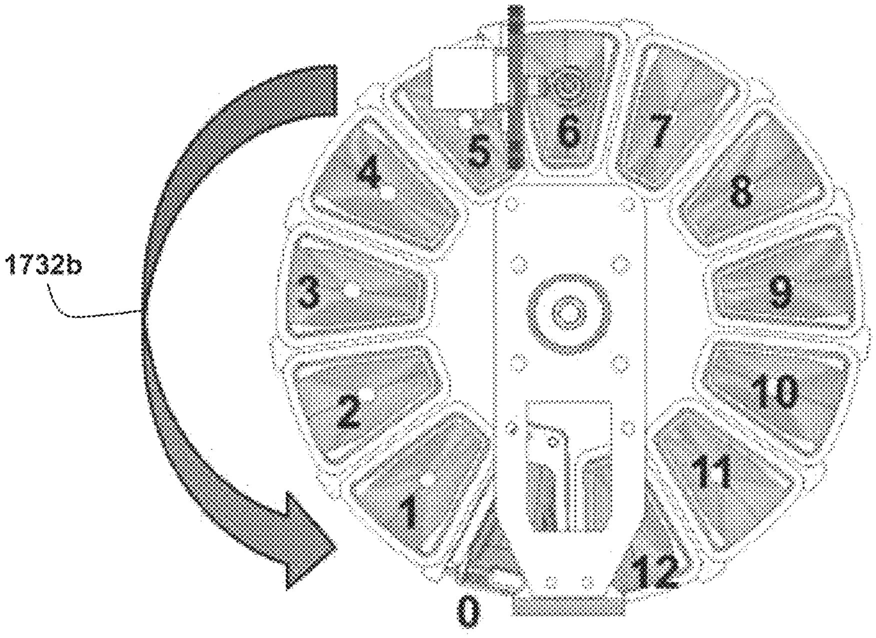

With specific reference to FIGS. 30A and 30B, rotation of the carousel 1726 while picking medications from two object bins, i.e., object bins 7 and 6, is illustrated. In FIG. 30A, the carousel is rotated to the right (arrow 1732*a*) to position object bin 7 at the start position under the robotic arm so that a medication may be picked. The carousel would then rotate back to the left (arrow 1732*b*) to position the dispense bin (0) at the start position under the robotic arm so that the picked medication may be dropped into the dispense bin. In this scenario, the next medication to be picked is in object bin 6. If the carousel were to be rotated to the right (arrow 1732*b*) to get to object bin 6, the dispense bin (0) would pass under the cam arrangement and the follower tab 1774 would cause the door 1778 to open. An absolute position of the carousel is controlled by the motor and information from the encoder 1720. In some implementations, the encoder is an absolute encoder so that the connected pill dispenser will not lose positional information, even in the event of a power loss.

In this scenario, since the dose includes more than one medication type (i.e., medications located in object bins 6 and 7), all medications are deposited in the dispense bin before they are released to the authorized patient or caregiver. As such, the carousel would be rotated back to the left (arrow 1732*b*) to position object bin 6 at the start position under the robotic arm (FIG. 30B). The carousel would then rotate back to the left (arrow 1732*b*) to position the dispense bin (0) at the start position under the robotic arm so that the picked medication may be dropped into the dispense bin. If the dispense bin now contains all of the medications for a dose to be delivered, the connected medication dispenser would wait for patient positive authentication, via either the patient/local caregiver mobile app or the display screen of the connected medication device, before rotating the carousel in either direction to cause the dispense bin to be positioned at the dispense position.

During the pick action described above, the connected medication dispenser may verify that each pick action has been successful, i.e., that a single medication has been picked. With reference to FIG. 31A, the connected medication dispenser includes a weight station 1748 at the start position, i.e., under the robotic arm and vertically aligned therewith. The weight station includes an actuator 1744 that provides vertical motion (arrow 1734) of a load cell 1740. As shown in FIG. 31A, the actuator 1744 may be attached to a bottom inner surface of the housing via a bracket 1746, and to a support stand 1736 via a guide rail 1742. For example, in the illustrated embodiment, the load cell 1740 may be positioned on a mount attached to a top of the actuator 1744, wherein the mount may include an attachment to the guide rail 1742 to provide additional support for the load cell and improve accuracy and robustness of the load cell. Positioned on the load cell 1740 is a bin platform 1738 sized and shaped to stably support an object bin 1750.

Figure 32:
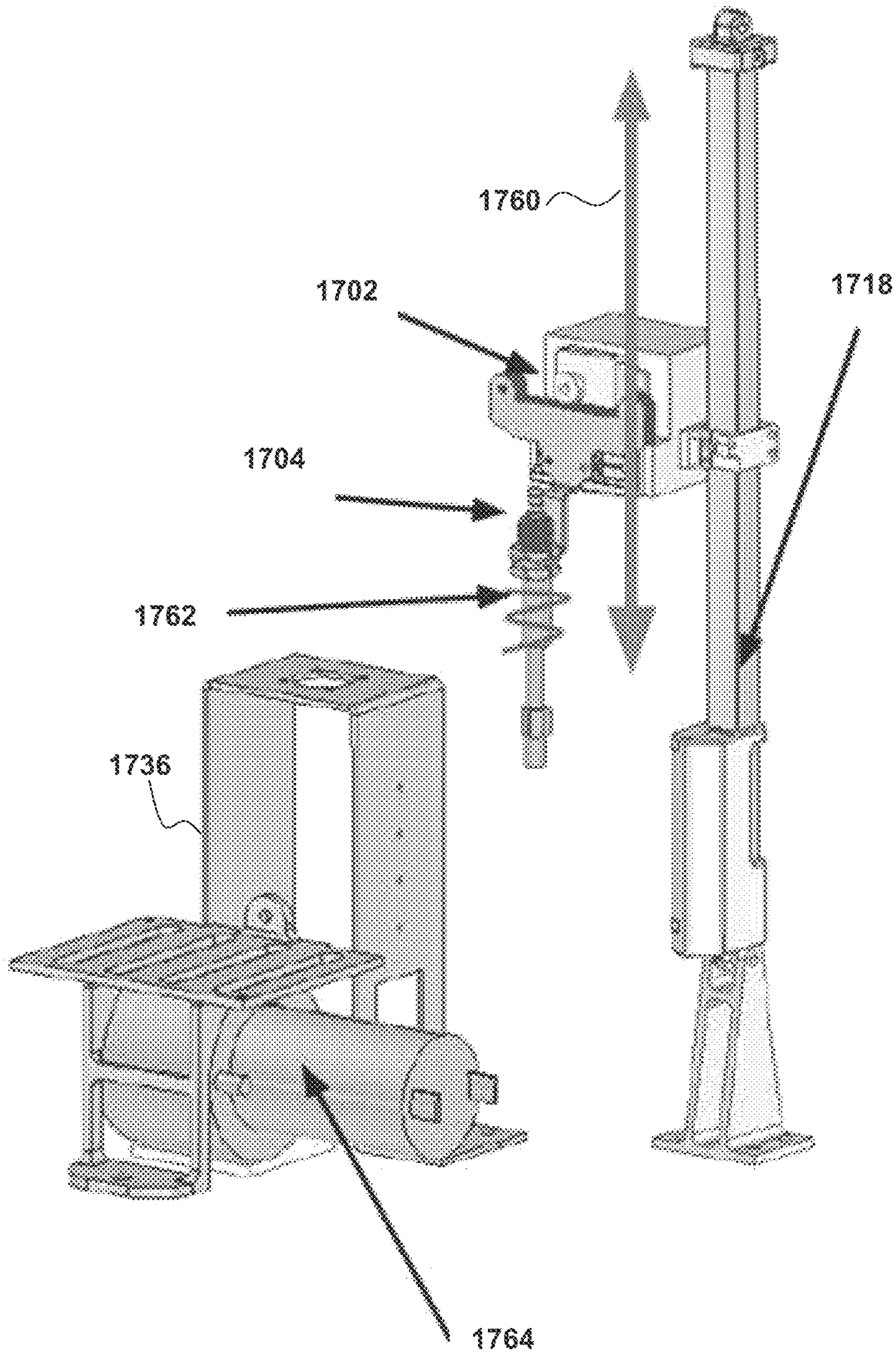
FIG. 32 depicts a robotic arm according to aspects of the present disclosure, wherein the robotic arm is shown as comprising a linear actuation for vertical translation and a rack and pinion system for horizontal translation of a medication gripping element.
Figure 33:
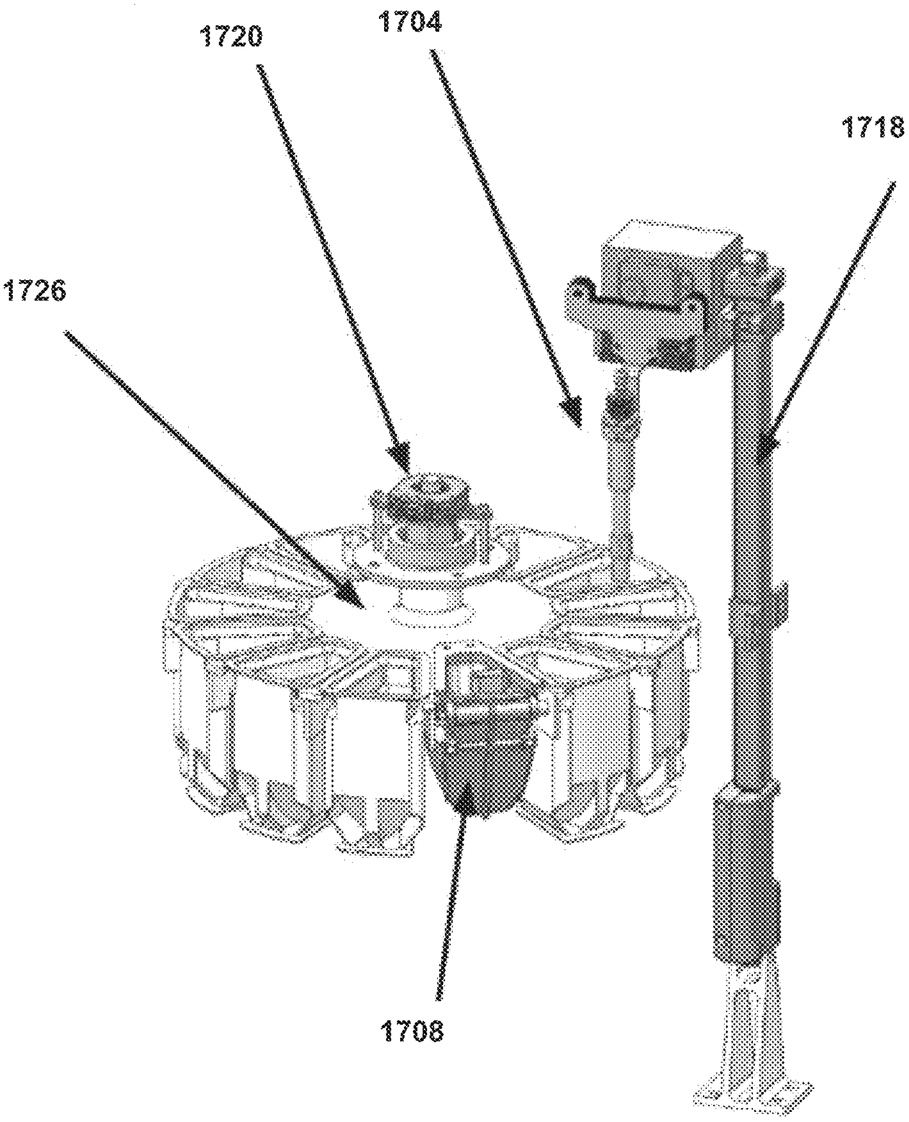
FIG. 33 depicts the robotic arm of FIG. 32 positioned over an object bin held within the carousel according to aspects of the present disclosure.

As such, and with reference to FIGS. 31A, 32, and 33, a typically pick action by the robotic arm includes (i) the actuator 1718 retracts to move the robotic arm downward (arrow 1760), and thus position the suction gripper 1704 within an object bin (1750), wherein suction is provided to the suction gripper by a vacuum pump 1764 so that a unit of medication may be pulled onto a suction cup of the suction gripper, and (ii) the actuator extends to move the suction gripper 1704 having a medication contained thereon upward and out of the object bin. The carousel may then rotate as described above to position the dispense bin directly under the robotic arm, wherein suction to the suction gripper may be interrupted so that the medication falls into the dispense bin.

The connected medication dispenser may verify that a single medication (e.g., pill) has been picked using the weight station 1748. According to one implementation, when a desired object bin is positioned at the start position, i.e., under the robotic arm, the actuator 1744 of the weight station 1748 may move the load cell 1740 upward (arrow 1734) so that a full weight of the load cell is support on the bin platform 1738 (note: the object bin 1750 is not removed from the carousel, but is pushed up an amount not exceeding the height 'a' of the recess 1751 so that a rim 1752 of the object bin no longer rests on the arms 1770 of the carousel). The load cell 1740 may then register a weight of the object bin supported thereon both before and after the robotic arm has attempted to pick a unit of medication as described above and communicate those measured weights to the processor and memory of the connected medication dispenser.

As previously mentioned, an expected weight of the object bin may be known from a previous weighing thereof by the load cell. Moreover, an estimated average weight of a unit of the medication may also be known from a weight of the object bin taken before and after a fill or refill of the object bin divided by the number of units loaded to the object bin. The robotic arm may attempt to pick a unit of medication from the object bin, as described hereinabove, while the object bin is support on the bin platform 1738, and the load cell may register a weight of the object bin during the pick attempt and/or thereafter. Should the weight measured after an attempt to pick a unit of medication differ from an expected weight by more than or less than the expected average weight of the unit of medication, the connected medication dispenser may register a failed pick attempt, i.e., more than one unit is picked, or no unit is picked, respectively. That is, the weight of the object bin is expected to decrease by the estimated average weight of a unit of medication stored in that object bin. For example, if the updated bin weight of the object bin changes by less than 70% or by more than 130% of the calculated average medication weight from a previously registered weight of the object bin, the medicine dispenser registers a failed pick attempt and is configured to repeat the attempt to grip the medication. In certain implementations, a failed pick attempt is recorded when the weight of an object bin measured after a pick attempt changes by less than 80%, 70%, 60%, or 50%, or by more than 120%, 130%, 140%, or 150% of the calculated average weight of a unit of the medication stored in that object bin from a previously registered weight of the object bin.

According to implementations of the disclosed connected medication dispenser, the object bins may be weighed (i) when empty, such as before loading, to provide a tare weight of the object bin, (ii) after loading with medications to provide a total bin starting weight and calculated average medication unit weight, and (iii) after a pick attempt by the robotic arm to provide verification of a successful pick and an updated bin weight, wherein each of the tare weight, total bin starting weight, calculated average medication weight, and updated bin weight are stored to the memory. The weight of an object bin may be measured only before and after a pick attempt by the robotic arm, i.e., the actuator 1744 of the weight station 1748 may move the load cell 1740 upward (arrow 1734) to weigh the object bin and downward to release the object bin 1750 for each collected weight.

Alternatively, the object bin 1750 may remain positioned on the bin platform 1738 and a weight may be collected continuously by the load cell 1740 during the entire pick attempt. In this latter implementation, additional information may be collected during the pick attempt, such as the downward force of the suction gripper within the object bin, which may be used to assist the pick action. That is, the actuator may be controlled to move the suction gripper downward into an object bin until the load cell registers an increased weight, i.e., registers a force applied to the medication in the object bin by the suction gripper (robotic arm). At a predefined increase in the weight measured at the load cell, the actuator may stop the downward movement of the suction gripper.

With reference to FIG. 32, the suction gripper 1704 of the robotic arm may include a pressure sensor (not shown). The pressure sensor may be included on the vacuum tube that connects the vacuum pump 1764 to the end of the suction gripper 1704 that includes a tip configured for gripping a unit of medication. Exemplary tips include a silicon suction cup or tube-shaped rubber skirt such as shown and described with respect to FIGS. 20A-H and 22A-C. The pressure sensor may detect an obstruction in the vacuum tube, i.e., increase in the vacuum pressure, such as when a pill has been pulled onto the tip of the suction gripper by the vacuum pressure supplied by the vacuum pump. In combination with the weight information supplied by the load cell, as described above, the connected medication dispenser may register a successful or failed pick.

For example, when a pressure increase is detected in the vacuum tube (i.e., by the pressure sensor), the actuator on the robotic arm may move the suction gripper upward to at least a position above the medication in the object bin. The weight information supplied by the load cell may then be used to determine if a single or multiple units of the medication have been picked. If more than one unit has been picked, the vacuum supplied to the suction gripper may be interrupted so that the units of medication may be dropped back into the object bin. Accordingly, a failed pick attempt is registered when more than one unit of medication is detected at the suction gripper. A failed pick attempt may also be registered when the suction probe fails to detect an increase in the vacuum pressure for a specific predefined interval, after which the actuator on the robotic arm may move the suction gripper upward to at least a position above the medication in the object bin. In both cases, the rack and pinion system 1702 shown in FIG. 32 may actuate a transverse motion of the suction gripper so that the tip (e.g., silicon suction cup) may move downward into the object bin at a different location during the next pick attempt, such as offset from the center of the object bin. This process may be continued one, two, three, or more times until a successful pick attempt is registered.

Figure 31B:
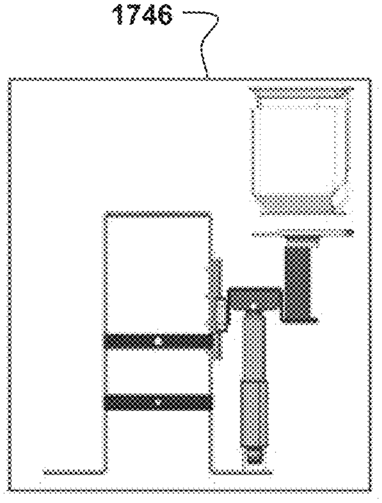
FIG. 31B depicts a side view of the weighing station of FIG. 31A, showing the bin platform below and separated from the object bin.

In some embodiments of the connected pill dispenser, when a successful pick attempt is still not registered after several repositioning actions of the suction gripper using the rack and pinion system 1702, the carousel may be shaken to reposition the units of medication in the object bins. For example, the motor on the carousel used for rotation of the carousel may execute several short, quick forward and backward rotations of the carousel, after which a new pick attempt may be executed as described hereinabove. When the carousel is to be shaken, the load cell of the weight station is lowered to a position below and separated from the object bins, such as shown in FIG. 31B. After the shake action is completed, the load cell may be raised to list the object bin for continued weight measurement by the load cell.

Various implementations may enable one or more pick attempts before and/or after the rack and pinion system is used to reposition the suction gripper, one or more uses of the rack and pinion system to reposition the suction gripper before a pick attempt, and one or more shake actions on the carousel before a pick attempt. The number and order of each action may be standardized, such as one pick attempt before use of the rack and pinion system, one pick attempt after use of the rack and pinion system and before shaking the carousel, and one pick attempt thereafter before the cycle starts again. The number and order of each action may also depend on the type of medication in the object bin, i.e., size and shape, and/or the number of units of medication remaining in the object bin.

Various implementations may enable the vacuum supplied to the suction gripper to be varied, such as based on the size, shape, and/or weight of the medication. For example, with larger and/or heavier medications, the vacuum pressure supplied to the suction gripper may be increased, while with smaller or lighter weight medications, the vacuum pressure may be reduced. In this latter case, the reduced vacuum pressure may reduce the rick that more than one medication is picked. Moreover, the vacuum pressure may be increased or decreased when a first or additional pick attempt has failed.

With continued reference to FIG. 32, the suction gripper 1704 of the robotic arm may include a spring 1762, i.e., the suction gripper may be a spring mounted probe. The spring 1762 may be configured to allow flexible motion of the suction gripper and tip (e.g., silicon suction cup or tube-shaped rubber skirt) in the x, y, and z directions.

Figure 35:
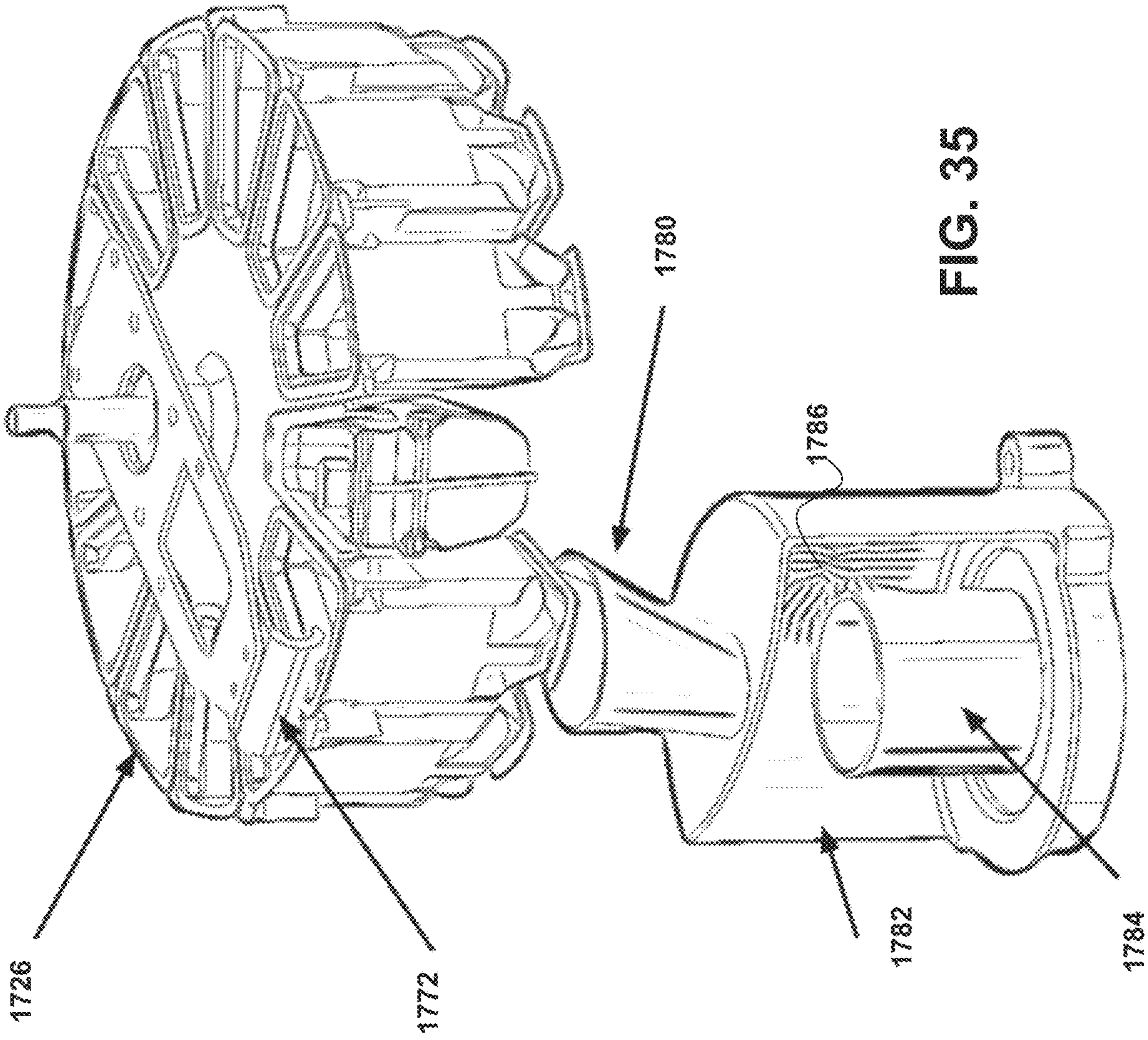
FIG. 35 depicts a door on the dispense bin opening as the carousel positions the dispense bin under the fixed cam, wherein medicine contained in the dispense bin is released into a hopper that directs the medicine to a medication collecting cup for patient retrieval.

With reference to FIGS. 34A-35, the arrangement of the hopper 1780 and pill collecting cup 1784 are depicted. As discussed herein, the dose is not picked and contained in the dispense bin and released therefrom until the patient/local caregiver has provided positive authentication in a timely manner, e.g., such as within a set time after the scheduled dose. When a dose is ready to be dispensed to the patient/local caregiver, i.e., after positive authentication, the carousel may rotate to position the dispense bin under the cam 1772 so that the follower on the door 1774 of the dispense bin is forced open to deliver the dose through the hopper 1780 and into the medication collecting cup 1784. The medication collecting cup 1784 is positioned on a cup platform (1785 of FIG. 25) that includes a limit switch that detects the presence of absence of the medication collecting cup 1784. Should the medication collecting cup 1784 be absent from the cup platform 1785, the connected medication dispenser will not release the dose from the dispense bin, even for an authenticated patient/local caregiver.

Once the dose is delivered to the medication collecting cup 1784, the patient/local caregiver will have a set amount of time to remove the cup from the cup platform 1785 and take their medication dose. Should this step not occur within that time, the connected medication dispenser may communicate with the central cloud server regarding a missed medication dose, i.e., lack of medication adherence. This information may also be communicated to the physician or remote caregiver, e.g., via their mobile device or server, the pharmacy server, the patient/local caregiver mobile device, patient selected third parties, and/or stored to the patient's EHR. A missed dose notification may also be displayed on the display screen 1802 of the connected medication dispenser.

The connected medication dispenser may further include an image sensor configured to capture images of patient medication consumption activity. These images may be analyzed by the medicine dispenser to identify images that correlate with image data representative of various patient activity states associated with medication adherence as discussed herein. Further, the captured images are time stamped based on time of capture to validate timing of medication adherence.

The connected medication dispenser may also include light elements, such as within the cup dispensing area (1786) and/or front of the housing that may provide visual indication(s) of an alert, such as an upcoming scheduled dose, a dose delivered to the medication collecting cup, a missed dose, and the like. The light elements may be programed to display assorted colors representative of various alerts or notification, which may be preset, or user selected. For example, the light elements may display white during setup or diagnostics of the connected medication dispenser; red when the dispenser requires immediate attention for proper functioning; yellow when one or more of the object bins has a low quantity of medication or requires manual attention, such as intervention for issues with the door on the dispensing unit, etc.; and blue as an indication of normal functioning.

The connected medication dispenser may further include a speaker configured to play audio cues, such as to remind a patient/local caregiver of an upcoming scheduled dose or newly added dose (e.g., real-time addition of an additional dose by the physician), time remaining to authenticate for a dose, a dispensed dose, time remaining to take a dispensed dose, or an combination thereof. The integrated speaker may also provide cues to assist the patient/local caregiver in authenticating using the connected pill dispenser, or cue directing authentication via another device (e.g., mobile device); loading the connected pill dispenser with medications and/or for setup of the connected medication dispenser, cues to assist in trouble shooting issues with the connected medication dispenser, and the like. The integrated speaker may also provide audio for video shown on the display screen, such as video help for setup and use of the dispenser; video help through the refiling process, such as when multiple medications are being loaded to different object bins; video help with troubleshooting, and the like.

Figure 36A:
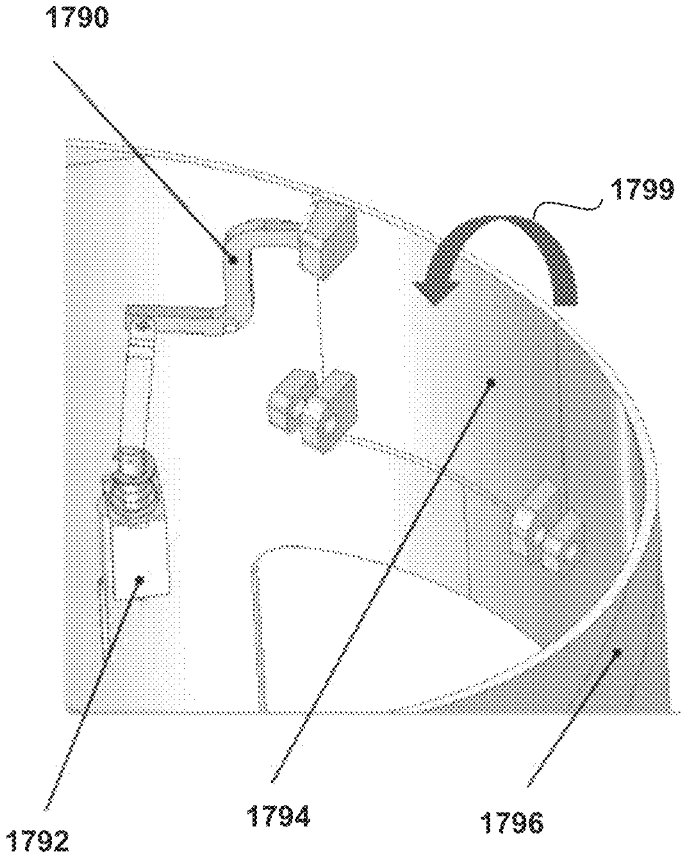
FIGS. 36A and 36B depict a refill gate in the open and closed positions, respectively, and exemplary components of the refill gate providing automated operation according to aspects of the present disclosure.
Figure 36B:
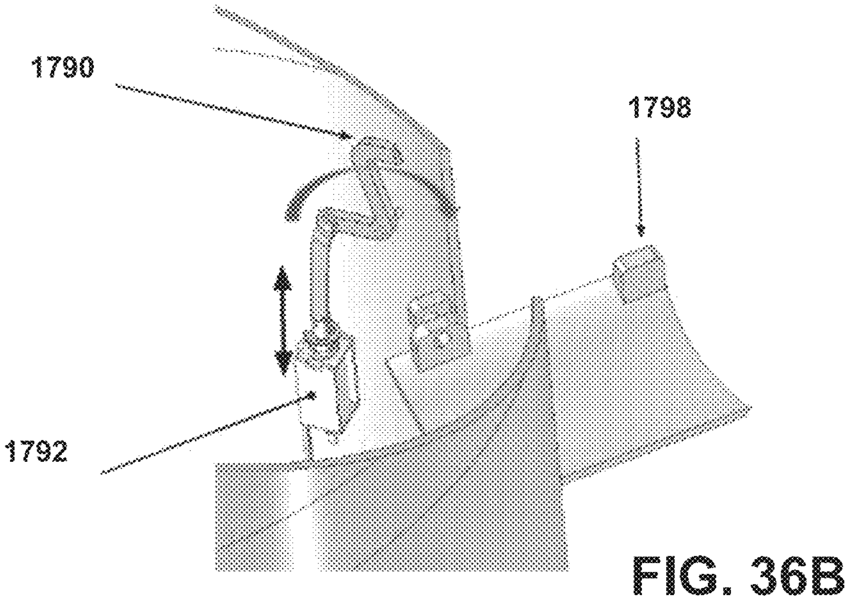
Figure 36C:
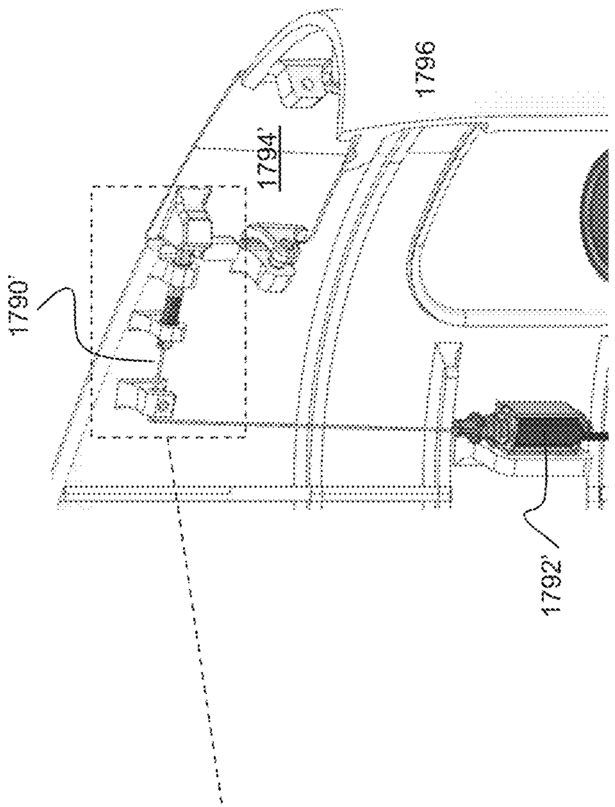
FIGS. 36C and 36D depict a refill gate in the open and closed positions, respectively, and exemplary components of the refill gate providing automated operation according to aspects of the present disclosure.
Figure 36D:
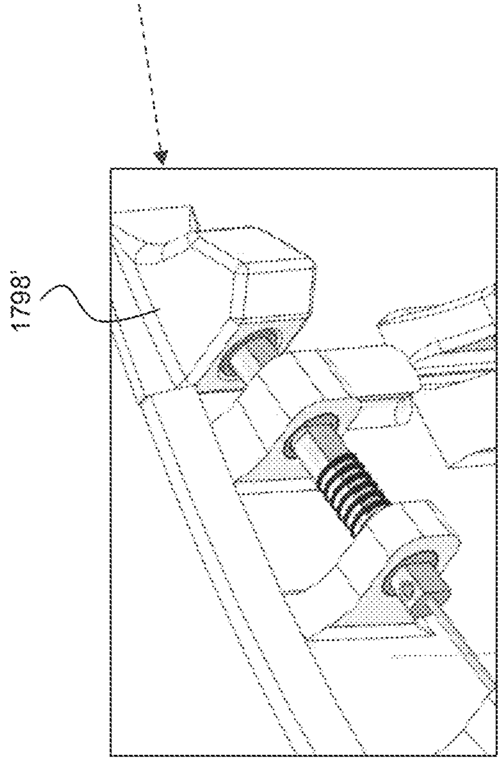

With reference to FIGS. 36A-D, a refilling procedure is discussed. The connected medication dispenser includes a refill gate 1794 positioned on a front of the housing 1796 of the connected medication dispenser that allows removal and replacement of an object bin to the carousel by a patient/caregiver. When the connected medication dispenser receives an authenticated refill command from the patient/caregiver via their mobile app or via the screen of the connected medication dispenser, the carousel will rotate to position an object bin in front of the refill gate. An actuator (1792 of FIG. 36A or 1792' of FIG. 36C) is electronically triggered to release a lock 1790/1790' holding the refill gate 1794/1794' in the closed position (FIGS. 36A and C), which moves the lock away from a cam 1798/1798', allowing the gate to swing open (FIG. 36B). In one implementation, the actuator is a spring-loaded solenoid that moves a pin downward (arrow) against the counterforce of a spring, causing a hinged lock to move away from a cam on the refill gate, and thus allow the refill gate to open. The refill gate may include a hinge biased to the open position.

The patient/caregiver may now remove the object bin from the carousel by pulling the bin horizontally away from the connected medication dispenser, and may refill the object bin. The patient/caregiver may be provided with specific visual and/or audio cues for refill steps and may interact with the connected medication dispenser via their mobile device or the screen of the connected medication dispenser, such as to indicate when a step is completed, the identity of the loaded medication, the number of medication units loaded, and the like. When the object bin is loaded, the patient/caregiver may replace the object bin within the carousel through the refill gate and may close the refill gate (arrow 1799).

A further exemplary design for a connected medication dispenser 1900 is shown in FIGS. 37A-39B. With specific reference to FIG. 37A, the connected medication dispenser 1900 is shown as including a medication retrieval bin 1910, and two object bin carousels 1935. As shown in FIG. 37B, the object bin carousels 1935 include recesses 1945 configured to accept a prescription bottle 1940, such as shown in FIGS. 38A and 38B. The prescription bottles 1940 may be filled by a pharmacy at the physician's or remote caregiver's direction based on a treatment plan, and the patient may simply place the prescription bottle into the recess within the carousel 1935. Also shown is a central support 1925 that provides axial rotation of the carousels, and the robotic arm 1930.

Actions and components of the carousel 1935 may be as described herein above for the connected medication dispenser shown in FIGS. 25-35. Moreover, actions and components of the robotic arm 1930 may be as described herein above for any of the disclosed connected medication dispensers (i.e., includes an actuator, motor, vacuum source), such as the connected medication dispenser shown in FIGS. 25-35.

Figure 37B:
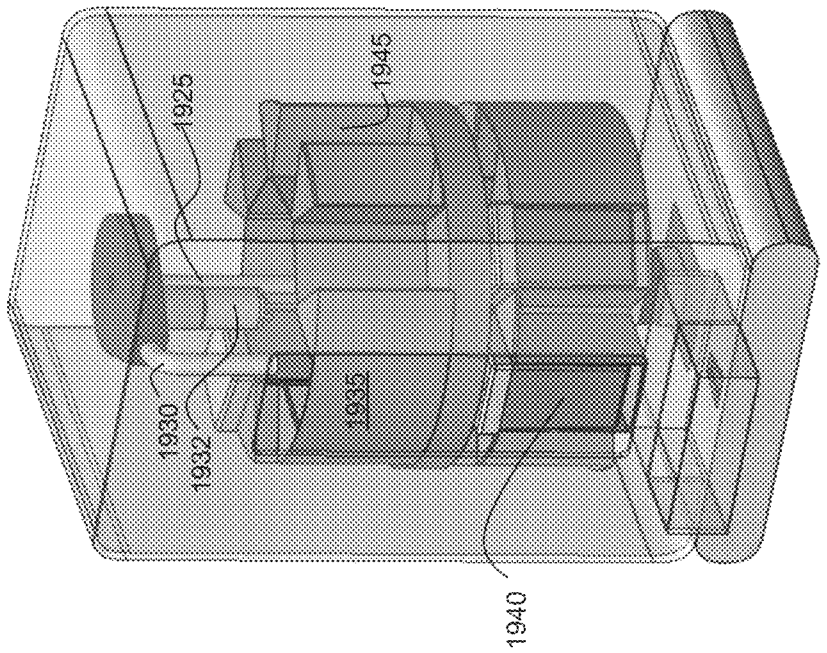
Figure 37A:
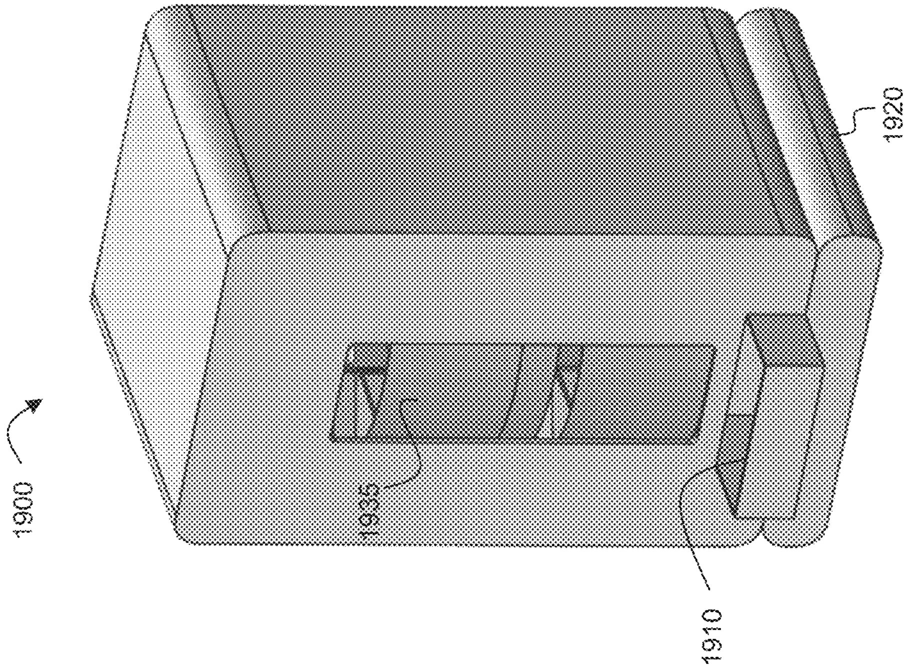

Further, as shown in FIG. 37B, the connected medication dispenser may include a door that opens to provide access to individual object bins, such as for removal or refill. Since the connected medication dispenser 1900 includes two carousels, each may have a region that denies access to object bins contained therein. For example, as shown in FIG. 37B, the upper object bin 1935 has a region that does not include a space for an object bin, i.e., no access region. When an object bin is removed or replaced to the lower carousel, the upper carousel is rotated to position the no access region adjacent the open door of the connected medication dispenser. Similarly, should an object bin be replaced or removed from the upper carousel, the lower carousel would be rotated to position the no access region adjacent the open door of the connected medication dispenser. The region behind the no access region is generally open, i.e., unobstructed, so that the robotic arm may travel vertically up and down to access the upper and lower carousels.

For example, when a medication to be picked is located in the lower carousel, the upper carousel would rotate to position the no access region thereof adjacent the door of the connected medication dispenser so that the robotic arm could travel downward through an open path behind the no access region to access object bins located in the lower carousel. Once a unit of medication has been picked by the robotic arm from an object bin in the lower carousel, it would move upward to a position above the lower carousel, and the lower carousel would rotate to position the no access region thereof adjacent the door. The robotic arm would then be able to move through the open space behind the no access region of the lower carousel to drop the medication in the medication retrieval bin 1910.

Figure 38A:
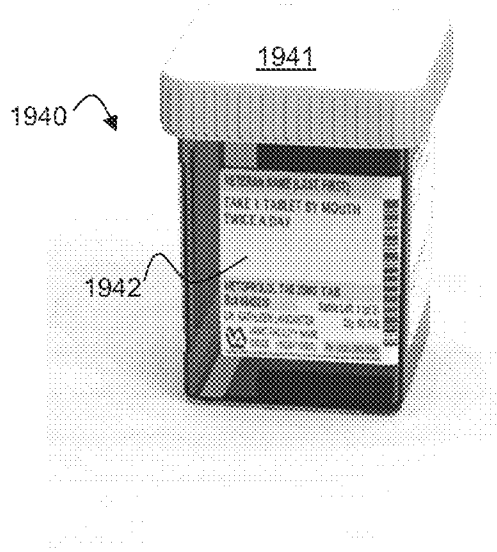
Figure 38B:
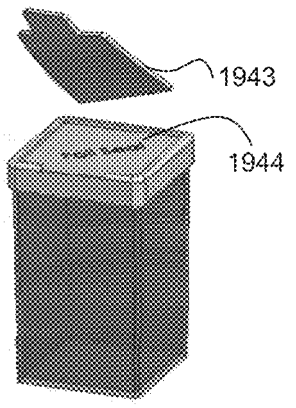
Figure 39A:
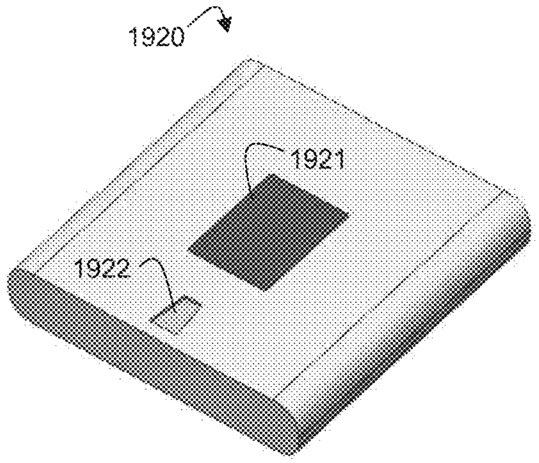
Figure 39B:
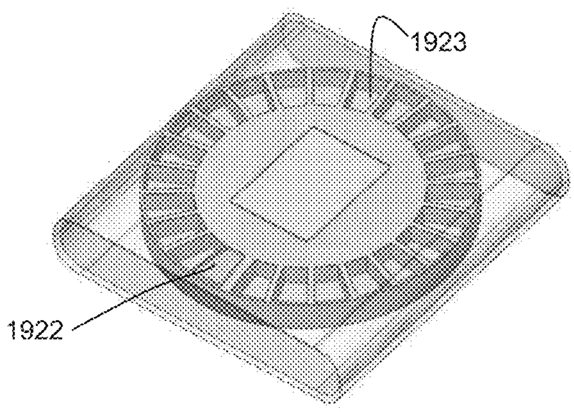

As shown in FIGS. 38A-B, the object bins 1940 useful in the connected medication dispenser may be configured as prescription bottles that may be filled at a pharmacy. The object bins 1940 may include a prescription label 1942 that may provide identifying information to the connected medication dispenser, such as via a scanner (barcode, QR code, RFID, etc.) positioned: on an inside of the housing, on an outer user accessible surface of the housing, or provided by the patient/caregiver mobile device. The object bins 1940 may be include a cap 1941 when provided by the pharmacy, which may be removed to expose one or more seals (1943, 1944). For example, a tamper evident seal 1943 may be removed to expose a foil seal 1944, which may also be tamper evident, wherein the foil seal may be left in place or removed prior to positioning the object bin 1940 in the connected medication dispenser. Such a solution may reduce possible errors in filling/refilling the object bins, such as errors in identifying the medication being loaded or loss of medication units, i.e., dropping pills.

While the objects bins 1940 are shown as having a square profile, other profiles and shapes are possible and within the scope of the present disclosure. For example, the objects bins 1940 may be round, hexagonal, octagonal, or may have a shape substantially the same as the objects bins 1940 shown in at least FIGS. 27A-C. In another exemplary design, the objects bins 1940 may have a substantially square or round shape and may have an inner sloped surface similar to the designs shown in FIGS. 27A-C (see 1753). The objects bins 1940 may be obtained by the pharmacy for prescription fills from standard manufacturers. Alternatively, the objects bins 1940 may be provided to the pharmacy with a code already embedded therein, such as an RFID code. In this latter case, the tracking of medications from manufacturer to pharmacy and to the final user (patient) may be fully enabled.

With reference to FIGS. 37A-B and 39A-B, an additional implementation of the connected medication dispenser is shown. A portable medication dispenser may be included, such as 1920 shown in FIG. 37A, that may be loaded by the connected medication dispenser 1900 to contain enough medication doses for one or more days of travel. The portable medication dispenser 1920 includes a carousel 1923 having individual bins that may be loaded with medication doses, i.e., all pills included for a specific dose, based on commands received by the patient/caregiver mobile app of web portal, and/or based on commands received by the physician server, pharmacy server, etc. Such commends may include the number of days the patient may be traveling, i.e., away from their main connected medication dispenser.

The portable medication dispenser 1920 includes a gate 1922 that may open when an authenticated patient/caregiver request receipt of a scheduled dose. Authentication may occur using a biometric scanner, such as a screen or fingerprint scanner 1921. The portable medication dispenser 1920 further includes a controller and motor to provide rotation of the carousel 1923 and opening of the gate 1922, a processor and memory configured to store schedules and collected medication adherence data, and a screen or fingerprint scanner to allow authentication of the patient/caregiver before dispensing a scheduled dose. In some implementations, the portable medication dispenser 1920 may further include a network interface so that the schedules and collected medication adherence data may be communicated with the central could server, and thus any one or more of the physician server or mobile device, pharmacy server, EHR, and the like as disclosed herein. The network interface may also allow the portable medication dispenser 1920 to receive information and commands from the mobile device of the patient/caregiver, such as authentication via the mobile app on the mobile device, dose schedules, changes to dose schedules and amounts, additional dose, etc. As such, the network interface may allow the portable medication dispenser to send and receive the same types of information to and from the same connected devices and servers as indicated herein for the disclosed connected medication dispensers.

Although various embodiments have been described with reference to the Figures, other embodiments are possible. For example, various embodiments describe a connected medication dispenser, which may be designed for use by a patient with an illness. Various embodiments include an internet-connected electro-mechanical connected medication dispenser that stores patient prescription and non-prescription medications; alerts patients and/or caregivers when doses are due; and dispenses prescribed doses with minimal intervention from the patient. Some exemplary devices may be designed to create value by improving patient adherence and compliance to a medication regime by use of technology as well as behavior management techniques. In an illustrative example, some embodiments can be remotely and dynamically programmed by the pharmacist, or the caregiver based on prescriptions from the patient's physician(s).

Exemplary connected medication dispenser implementations may be designed to perform various operations based on sensor data. The sensor data may be acquired by one or more sensors operably coupled with a processor configured to operate with the connected medication dispenser. The one or more sensors operably coupled with a processor configured in the connected medication dispenser may include sensor(s) of diverse types. The operations performed by an exemplary connected medication dispenser based on sensor data may include, for example, capturing baseline or reference data for comparison with live sensor data, capturing reference data for configuring or training a machine learning or artificial intelligence model or structure to create predictive analytic output representative of a patient outcome based on sensor data, measuring patient physiological parameters, adjusting a dose, determining patient condition, determining medication adherence, or adapting the operation of the connected medication dispenser, in response to the sensor data processed by the connected medication dispenser.

For example, a sensor configured to operate with an exemplary connected medication dispenser may be a device-centric sensor, or a patient-centric sensor. A device-centric sensor may be, for example, a sensor configured in the connected medication dispenser to acquire data associated with the device or the patient. A device-centric sensor may be a sensor configured in the device to detect tampering, to determine when a patient has opened or closed a dispensing chute access door, or a camera configured in the device to capture images of patient medication consumption activity. A patient-centric sensor may be, for example, a sensor configured in the connected medication dispenser or worn by a patient, to acquire data associated with a patient. A patient-centric sensor may be a physiological sensor designed to transduce a patient physiological response acquired by the sensor to a signal data package consumable by a processor. An exemplary signal data package may include one or more signal, noise, or other data. For example, some sensor types may include time stamps correlated with signal data, such as photographs. In any case, a sensor, or the processor, or both, nay be configured to process into useful form the signal data package emitted by the sensor, based on isolating the desired signal from the signal data package.

A device-centric sensor configured in the connected medication dispenser to acquire data associated with a patient may include an image sensor, such as a still picture camera, video camera, infrared camera, time of flight camera, or other imaging device. A still picture camera may be used to capture a patient image useful for authentication, such as, for example, by facial recognition, facial biometric feature identification (for example, matching the geometry of facial features such as displacement and structure of eye sockets, nasal bridge, or mouth or lip geometries, to previously captured images of the patient). In some examples, facial identification and biometric feature identification may be augmented with distance from target data provided by a time-of-flight camera, permitting more accurate identification based on facial features measured with respect to facial distance from the camera.

An image sensor such as a video or still picture camera may facilitate medication adherence determination based on computer vision. For example, captured video or still images of patient activity may be analyzed by a connected medication dispenser to identify images that can be correlated with or matched to image data representative of various patient activity states such as limb positions, hand positions, postures, gestures, or reflexes, associated with medication adherence. For example, a sequence of images of a patient could be captured while the patient consumes a medication dose. The captured images could be time stamped based on time of capture, to validate the timing of patient consumption activity with respect to patient-specific baseline consumption time (for example, compared with the length of time required for the patient to consume the dose in a controlled, or supervised, successful test dose). The time stamped images could be correlated to images captured of the patient consuming medication in the controlled or supervised setup operation, to validate the patient consumption of the medication dose. In some examples, an alert may be triggered, if the dose is not consumed within a threshold period in excess of the patient-specific baseline consumption time.

A device-centric sensor configured in the connected medication dispenser to acquire data associated with a patient may include an audio sensor, such as a microphone. A microphone may be used to capture patient audio representative of patient identification or communication. For example, speaker identification techniques may be used to authenticate a patient based on audio data captured by microphone. Speaker recognition techniques may be used to transform a patient's verbally spoken words to text for processing by an exemplary connected medication dispenser. For example, an embodiment connected medication dispenser may determine a patient condition at least in part by verbally asking a patient if they feel better or worse, if they feel warm or have chills, how many medications they swallowed, the color of the medications swallowed, or if they still have a headache. In response to such questions, a patient may verbally respond with one or more word, 'Better,' 'Warm,' 'Three,' 'Yellow,' or 'No,' and the words may be transformed to text for processing by an exemplary connected medication dispenser. In some examples, patient responses may be used by an embodiment connected medication dispenser to interactively traverse a diagnosis or treatment determination decision tree, based on comparing patient responses with responses encoded by the tree. Various connected medication dispenser designs may employ such a decision tree to prescribe medication, adjust a medication dose, recover from a missed dose, or send a notification. Such a diagnosis or treatment decision tree may be provided for use in the connected medication dispenser by a healthcare or healthcare service provider, such as a physician, payer, or pharmacy. Various connected medication dispenser designs may receive diagnosis or treatment decision tree guidelines that are automatically updated when prescribing or treatment guidelines are revised by pharmaceutical companies, payers, or government regulatory agencies.

Some connected medication dispenser designs may permit a patient's treating physician to customize a diagnosis or treatment decision tree to the patient. In an illustrative example, such a customized patient-specific diagnosis or treatment decision tree may include steps specific to a patient's condition, such as, for example, ensuring a patient has consumed one type of medication, before attempting to provide the patient a dose of another type of medication. Other custom steps could include, for example, determining if the patient is anxious, based on verbally asking the patient if they are anxious, and analyzing the patient verbal response; in response to determining the patient is anxious, measuring the patient's blood pressure to determine if the patient's blood pressure is within normal range; in response to determining the patient's blood pressure is above normal range, dispensing a blood pressure medication dose determined as a function of the blood pressure measurement and prescribing guidelines determined by the patient's physician; and, in response to determining the patient's blood pressure is not above normal range, dispensing an anti-anxiety medication dose prescribed by the patient's physician.

In some examples, the connected medication dispenser may provide the status of traversing such a diagnosis or treatment decision tree to the patient's physician. For example, the patient's physician could customize a patient-specific decision tree configuring an exemplary connected medication dispenser to notify the physician immediately if the patient has a headache, the patient has consumed the prescribed blood pressure medication, and the patient has blood pressure above a predetermined minimum blood pressure level. In such an example, the physician responding to the notification may further interact with the patient by voice or video to determine the next treatment action. In some examples, the physician may remotely direct the exemplary connected medication dispenser to dispense additional blood pressure medication, or headache medication, or both.

In various scenarios, an exemplary connected medication dispenser implementation may adjust a medication dose. A patient's physician may adjust a blood pressure medication dose to be dispensed by the exemplary connected medication dispenser for the next several doses, in response to the patient condition. The patient condition may be determined by the connected medication dispenser 110 based on sensor data. The physician may change the prescription governing the dose to be dispensed by the exemplary connected medication dispenser for all subsequent doses. In some examples, the exemplary connected medication dispenser may be programmed and configured to autonomously adjust the dose of a particular medication specified by the physician in a dose amount varied within limits determined by the physician and prescribing guidelines. For example, the exemplary connected medication dispenser 110 may determine the patient condition based on sensor data, adjust a medication dose based on the patient condition, deliver the dose to the patient, and determine medication adherence based on sensor data.

Some exemplary designs for the connected medication dispenser may adjust a medication dose in accordance with a treatment decision tree encoding dose limits depending on patient physiological parameters. For example, an exemplary connected medication dispenser may measure a patient's heart rate, temperature, and blood pressure physiological parameters, determine, based on the measurements, the physiological parameters are within normal range for the patient, and the exemplary connected medication dispenser may dispense a nominal amount of multiple medications, including a daily, nominal blood pressure medication dose, according to a scheduled dosing regimen. In another example, the exemplary connected medication dispenser may measure a patient's heart rate, temperature, and blood pressure physiological parameters, determine, based on the measurements, the blood pressure parameter is below normal range, and dispense a reduced blood pressure medication dose, based on the low blood pressure measurement. In some examples, the exemplary connected medication dispenser may substitute another medication, for example, a diuretic medication, in place of the blood pressure medication, in response to the low blood pressure measurement. Various exemplary connected medication dispenser implementations may adjust the medication amount of a dose calculated as a function of a patient physiological parameter measured by a sensor, in view of dosing guidelines programmed and configured in the exemplary connected medication dispenser. In some examples, the patient's physician may be notified, and manually adjust the dose. Various implementations may provide capability to perform autonomous dose adjustment by the exemplary connected medication dispenser 110, and manual dose adjustment by a healthcare professional in the treatment loop, facilitated by the exemplary connected medication dispenser.

In an illustrative example, an exemplary connected medication dispenser may be configured as a hub for other patient-wearable sensors, data from which can be utilized to enhance determination of medication adherence. For example, an EKG monitor, blood pressure monitor, thermometer, or other patient-owned device may be wirelessly paired or connected with the connected medication dispenser, to provide additional and/or alternative data sources used to determine medication adherence.

In an illustrative example of automatic dose adjustment by an exemplary connected medication dispenser, a blood-pressure monitor could provide data to the connected medication dispenser that could then automatically adjust the number or schedule of blood-pressure-controlling medications dispensed. The physician could set dose and/or schedule limits that the connected medication dispenser must operate within. The connected medication dispenser could report patient progress to the physician. The connected medication dispenser could also report if the dispenser reaches the allowed dose and/or schedule limits to allow the physician to evaluate the patient, drug selection, and/or drug dosage.

In various scenarios, an exemplary connected medication dispenser implementation may determine medication adherence based on data acquired from one or more sensor. For example, an exemplary connected medication dispenser design may compare captured video, audio, or image data representative of a patient's putative medication consumption activity with baseline or reference data representative of successful medication consumption, to determined medication adherence based on the comparison. Some exemplary connected medication dispenser implementations may be configured with patient-specific machine learning models trained with baseline successful and unsuccessful consumption activity. In an illustrative example, such a patient-specific model may be employed to predict successful medication consumption as a function of live video, audio, or image data representative of a patient's activity attempting to consume medication. Various imaging techniques may be employed to capture the patient and dose delivery environment state before and after the putative dose event. For example, an image of a cup of water used to help swallow a medication may provide a proxy for determining if the medication was swallowed; that is, if the cup water level has declined between start of dose, and end of dose event, and the patient when asked responds they have consumed the dose, a prediction the patient consumed the dose may be made. In some examples, computer vision techniques including object tracking, motion detection, object identification, and optical flow may be employed to determine medication adherence. For example, the patient could be asked to show to the camera their hand holding the medication to be swallowed, then video could be captured of the patient moving their hand to their mouth and showing their empty hand to the camera. In some examples, audio confirmation of the patient swallowing may be obtained by a microphone. In an illustrative example, the exemplary connected medication dispenser may use object identification techniques to identify the medication in the patient's hand, to determine medication adherence based on identifying the medication and the medication location in the patient's hand. The exemplary connected medication dispenser may use object tracking techniques to track and record the path of the patient's hand to the patient's mouth, the path of the patient's hand to pick up a cup of liquid from a table, move the cup to the mouth, swallow the liquid, and return the cup to the table, to determine medication adherence based on comparing the patient's hand motion to predetermined hand motion representative of a successful dose event. Various examples may validate medication adherence based on physiological sensor data; for example, if blood pressure medication is delivered to a patient, and the patient's blood pressure should be expected to decline but does not, such an event characterized in terms of an expected but not realized response in the patient's blood pressure may reduce the probability medication was consumed successfully.

Some exemplary implementations of the connected medication dispenser may verify the patient has taken the prescribed medication dose based on a signal from a medication dose configured to wirelessly report when the dose has been ingested. The connected medication dispenser may incorporate wireless connectivity directly to such a medication dose that wirelessly reports when the dose is ingested. The connected medication dispenser could also incorporate wired or wireless connectivity to the monitoring devices associated with such medication doses that wirelessly signal when the doses are ingested.

In various scenarios, an exemplary connected medication dispenser implementation may compensate for one or more missed medication dose. As disclosed herein, an exemplary connected medication dispenser may determine a patient's medication adherence to a prescribed dosing regimen using various techniques. In an illustrative example, when a patient's lack of medication adherence is determined for a specific dose by an exemplary connected medication dispenser, at least that dose may be considered a missed dose. In some examples, the missed dose may be skipped, and the next scheduled dose may be attempted by the connected medication dispenser in accordance with the prescribed dosing regimen. However, an effective plan to recover from one or more missed dose may enhance patient well-being and reduce risk to patient health. In an illustrative example, different drugs may have different recommendations for how to recover after one or more missed dose, to optimize therapeutic value and reduce risk to the patient's health. In some scenarios, an exemplary connected medication dispenser design may be programmed and configured with drug-specific missed dose recovery protocols based on pharmaceutical manufacturer recommendations. For example, one missed dose recovery response implemented by an exemplary connected medication dispenser based on drug manufacturer recommendations may be to ignore the missed dose and continue the normal schedule.

Another response implemented by an exemplary connected medication dispenser based on drug manufacturer recommendations may be to double the next dose and then return to the normal schedule. In some examples, the connected medication dispenser and/or cloud may store the drug-appropriate recovery and implement the recovery automatically. Alternatively, an embodiment connected medication dispenser may alert a pharmacist and/or physician to define and/or implement the appropriate recovery.

In an illustrative example, various embodiment implementations may facilitate better communication among the pharmacists, the physicians, the caregivers, and the patients and allow for monitoring of patients' adherence and administration of the right dosage of medication, based on use of technology. For example, information gathered on patients' extended medication compliance in turn helps the payer community get visibility into the patient compliance to medication, and subsequently effectiveness of the treatment. In some examples, nudging patients adhering to the prescribed medication, and establishing strong correlation between clinical compliance and treatment effectiveness leads to a better patient outcome, and ultimately reducing the overall healthcare cost.

Various embodiment implementations are positioned as a solution designed with the goal of increasing patient adherence with medicine by addressing the main pain points that other competitive solutions in the market fail to capture. With the innovative use of technology and application of modern techniques of social and behavioral science, the presently disclosed systems drastically simplify medicine adherence for patients. In the process, it creates win-win factors for the eco-system of healthcare providers, payers, and caregivers such that participation into the process rewards all eco-system players and contributes towards reduction of the overall healthcare cost.

In an illustrative example, an object of the present invention is to build the next generation connected healthcare technology platform that improves lives by nudging patients of various illnesses to maintain adherence to medication, leading to a better patient outcome and an overall reduction in ever-rising healthcare cost throughout the world.

According to National Council on Patient Information and Education (NCPIE)-Medication "non-adherence" (also known as "non-compliance") means not taking your medicine as prescribed according to the directions of your healthcare provider and/or the directions on the medicine label.

Lack of prescription medicine adherence and compliance can lead to unnecessary disease progression, disease complications, a lower quality of life, and even possibly premature death. Lack of prescription medicine adherence is a phenomenon that is a major contributor to ever-rising healthcare cost in the US. Approximately half of the estimated 187 million Americans who take one or more prescription medicines do not take their medications as prescribed, according to NCPIE.

The U.S. pays a high price for poor adherence: lack of medication adherence is associated with poorer health outcomes, resulting in approximately 125,000 preventable deaths a year. On a national level, avoidable medical spending (such as ER visits, hospitalizations) resulting directly from non-adherence accounts for up to $290 billion per year, or 13 percent of total healthcare expenditures. In this way, non-adherence to medicine can not only hurt individual patients, but also hurts our healthcare system.

Whether "Tips for keeping track of your medications and remembering to take them" by NCPIE (http://www.bemedwise.org/medication-safety/medication-management-adherence), or "8 Tips to Sticking to Your Medication Routine" by Food and Drugs Administration (FDA) (https://www.fda.gov/Drugs/ResourcesForYou/SpecialFeatures/ucm485545.htm)—it is increasingly challenging for patients to adhere to medicines for multiple factors as further described by NCPIE as below—"Medication "non-adherence" or "non-compliance," either intentionally or inadvertently, can include, for example: Failing to initially fill a prescription; Failing to refill a prescription; Discontinuing a medication before the course of therapy is complete; Taking more or less of a medication than prescribed; or, Taking a dose at the wrong time."

Medicine adherence is a complex issue contributed with behavioral and non-behavioral factors, costing the US healthcare system 100's of billions of dollars every year. What if there is a single solution to address majority of such issues?

Connected Medication Dispenser:

Various embodiment connected medication dispenser designs include an electro-mechanical device, which is remotely connected to central cloud server via cellular and/or Wi-Fi connection. For example, the device may have storage capability of 10-12 different medications for 30-90 days' supply. It can be remotely programmed to schedule auto dispensing of medications. The device provides visual and sound alerts to patients or patients' caregivers when a dose is due. The device dispenses the medications in a hygienic manner (in a cup or an embedded tray) when the patient or the caregiver provides a signal (e.g., patient/caregiver enters a special code, or a biometric signal such as fingerprint is provided by the patient).

In some embodiments, the connected medication dispenser may use a special algorithm to identify if a patient has taken the medication within a certain period after it is dispensed. The inputs to the algorithm are the various information it gathers, such as—time of the alert, the number of times the alerts are generated within a certain period, if the caregiver or the patient has dispensed medicine within a preset time after the alerts are generated etc. Other behavioral measures will be incorporated to get a better and accurate gauge of the adherence of medication.

Some embodiment connected medication dispenser designs may be capable of managing medication counts at all times, generating alerts based on the medication counts for the pharmacy to learn about how long certain medications' supply would last for the patient. This information will be critical for the pharmacy to replenish the drug for the patient on time (that is, for example, via an auto refill reminder).

Web Portal:

In various embodiments, the web portal 165 may be designed primarily for the pharmacist, physician, or remote caregiver to interact with the patients. Some embodiment web portal 165 implementations may enable secure access to each patient's connected medication dispenser and all the information related to its medication configuration, doses programming, medication counts, and patient's information. Some embodiment web portal 165 implementations may enable secure access to each patient's electronic health record and all or relevant portions of the information related to the patient's medical status, treatments, appointments, prescriptions, etc.

In some web portal 165 designs, a pharmacist will be able to program the dose times as per physician's or remote caregiver's prescription using the web portal 165 for each of the patients it serves. Based on a change of prescription, the pharmacist, physician, and/or remote caregiver will be able to program any change of medication regime remotely and dynamically as well.

Various embodiment web portal 165 implementations provide a source for the pharmacist, physician, or remote caregiver to get access to patient's alerts and notification, which will be individualized based on patient's needs and service plans. For example, the web portal 165 may alert the pharmacist when the medications deplete to a pre-determined level (e.g., 25% medications remaining for a refillable medication), such that pharmacist can assist the patients by pro-active scheduling for replenishment of medications and finally replenishing them on time. This also allows pharmacists to maximize their medication dispense revenue. The pharmacists can also get access to weekly/monthly/annual reporting of patient's compliance or adherence information from this portal.

In an illustrative example, a physician or remote caregiver can get access to patient's information via an embodiment web portal 165. This will provide the patient's medication compliance information/report, which can directly assist the physician in assessing the efficacy or effectiveness of the prescribed medication.

Further, the payer can assume access to similar type of information for the patients they indirectly reimburse for.

Mobile App:

In various embodiments, the mobile app 135 may be designed for the patients, the caregivers, the pharmacists, and/or the physicians. An exemplary app 135 may provide patients with information about the medications and their doses. It also synchronizes with pharmacists' portal information dynamically. In an illustrative example, an embodiment app 135 may serve as an alert center to remind patients of medication time or missed doses.

In some examples, an embodiment app 135 may allow the patients to securely communicate with the pharmacists, the caregivers, and with the physicians. It further allows patients to discover friends and family utilizing the same app and create a social network to keep tab of each other's health progress, as well as to provide encouragement to each other via social gaming.

In an illustrative example, caregivers of the patients will have access to patient's medication adherence information. In some examples, a social aspect will be designed in the app for caregivers to encourage patients with their medication regime based on the alerts they will receive regarding the patients' compliance. Similarly, when the patients miss a dose, the caregiver will be notified by the mobile app and can intervene as necessary on a real-time basis. This will further ensure the patient's adherence factor improves by such social interactive techniques via various mobile app 135 designs.

In various embodiments, pharmacists may have access to the mobile app 135 to monitor multiple patients in a secured way. The pharmacists will be able to use the mobile app 135 to establish connection with a particular patient's connected medication dispenser remotely or using NFC wireless communication method while nearby the device. This is to allow the pharmacy representative to identify him/herself to open the locked connected medication dispenser to replenish medications. Some embodiment mobile app 135 implementations may also allow the pharmacists to configure medicine schedule per individual patients and generate alerts when the patients run low on their meds supply.

In various examples, physicians may have access to an embodiment mobile app 135 to monitor individual patients, get notifications based on certain conditional threshold, visibility of the meds schedule, and ability to adjust medication on a dynamic basis.

Application Programing Interfaces (APIs)

In various implementations, a set of RESTful APIs are available for pharmacists to integrate the systems and software disclosed herein with their existing application(s), or to allow for customization and optimization of their patient operations. The APIs may provide similar functions as available via the cloud platform. In some designs, the APIs may be available for both desktop and mobile app.

In various scenarios illustrative of some embodiments' usage, other eco-system entities, such as physician's offices, managed care services, hospitals, rehabilitation centers, and payers, may choose to consume APIs to have authorized and secured access to patient's medication and compliance information from remote applications.

Some exemplary APIs may also be designed for the companies interested in utilizing the systems disclosed herein for clinical studies, such as for monitoring and data gathering purposes. Further, third party companies, working to improve overall healthcare systems, can use the APIs to access aggregated and anonymized medicine adherence and other patient related information as per regulation and patient consents.

Cloud Based Central Server

Some embodiment implementations of the disclosed cloud platforms may include a cloud-based central server configured to act as a hub or the platform for the entire solution, and facilitate policy, configuration, and communication among multiple parties and user interfaces involved in the solution. In various embodiments, the cloud-based central server may be a healthcare regulations compliant system, which will also record patient behavior, adherence factors, and administrative records, among many other functions.

Business Models

In illustrative, non-limiting examples, various business models are disclosed, including a B2B INDIRECT, B2B DIRECT, and B2C DIRECT/INDIRECT business model. An embodiment connected medication dispenser may implement various business model features. Some embodiment business model designs may include features implemented via a connected medication dispenser design.

B2B Indirect

Via the Pharmacies (Medicare/Medicaid/Insurance pays): In an illustrative example, it is an object of such a model to incentivize pharmacies to contribute towards the medicine adherence of the patients. For example, a pharmacy specializing in serving drugs for medical conditions and having an established (or willing to establish) home delivery model can take advantage of this business model.

In an illustrative example, a new Medicare/Medicaid/Insurance (for example, the payer community) code for the eco-system of providers may be created for such a service model, for personalized and preventive care, such that the payer community reimburses the cost of the devices, device support and pharmacists' services.

Based on patients' condition and adherence requirements, physicians may prescribe the connected medication dispenser (that is, the device) to the patients. Pharmacies may fulfill the prescription by filling in the medications and programming the prescription in a new device for the patients. The patients or the caregiver may carry the device home and stay connected by plugging into an electrical outlet. The device may remind patients of the doses, collect adherence events per dispensing of the medications, and inform the pharmacists when the supply runs low.

In some designs, the pharmacists may replenish the medicine supply when electronically notified by the device and charge the payer for the meds. Various device implementations may collect the compliance and adherence report and send the compliance and adherence report to the physicians' offices or to the payers, as necessary. The payers may reimburse the pharmacists for their services. In some scenarios, this facilitation may help the pharmacists earn a service fee on top of the slim margin they may earn by dispensing medicine for the patients.

Physicians may monitor patients with illnesses on a 24×7 basis utilizing technology. In various embodiments, the patients' vital information and medicine adherence report may be sent to physicians on a dynamic basis, for example, triggered on-demand in response to alerts. Various examples may generate alerts and trigger sending vital information and medicine adherence reports to physicians, according to patients' preset thresholds of vital signs and adherence factors. In an illustrative example, reports may be generated utilizing communication of choice (mobile app, email, phone call, text, and visual notification via desktop application). The physician may intervene as necessary to manage the patient condition. For example, the physician may simply adjust the medicine doses according to patient's condition remotely via mobile app or the desktop application, which may include securely accessing the patient's medicine profile.

The physician may request via the presently disclosed mobile or desktop applications, or via a traditional method of calling into the designated pharmacy for a change of medicine—for example, replace a certain medicine, or add a new drug in the patient's prescription. Accordingly, the pharmacy physically delivers the medicine to the patient and fills the connected medication dispenser. The patient or caregiver may choose to bring the connected medication dispenser or the medication tray to the pharmacy, if allowed to manage the connected medication dispenser, for adjustment of medicines. The pharmacy may reprogram the change of prescription.

A physician or nurse may choose to have a telephone call or a video call with the patient by directly reaching to a medical hub of the system, such as supported by a central could server. The patient may utilize the inbuilt calling/video-calling features to have such communications. A physician or nurse may choose to have a communication with the caregiver to discuss patient's condition and prescribe the next course of action for the patient to take. Such communication can happen via a telephone call, text, or alerts/messaging features of the caregiver mobile app.

In some examples, a new Medicare/Medicaid/Insurance code for the physicians may be created for such a service model for personalized and preventive care. Such business model will be a departure from the traditional model, where the physician-patient relationship is transaction based, versus a continuous service-based model. While this new continuous service-based model will allow physicians to have a new form of revenue stream, the overall idea is to enable personalized medicine by better monitoring, medicine adherence, and dynamic adjustments of medicine, such that patients' overall health improves, while the overall long-term health-care cost goes down.

B2B Direct

Patient monitoring by the hospitals may reduce readmission rate, the hospitals may require remote patient monitoring and monitoring of medicine adherence by the patient. In such a model, the hospitals may procure the connected medication dispenser and send the device with discharged patients having had an illness where the chance of readmission is high. The mobile app and/or and web interface access may allow the hospitals to manage the devices remotely and get patients' reports for a period deemed necessary for the hospitals to keep a patient on this program. In an illustrative example, a hospital may purchase the devices and associated support services one time and rotate the device until the end of the device service life. Alternatively, a hospital may rent the device.

Patient monitoring may also be done by rehabilitation centers. Certain rehab centers are compelled to monitor patients' drug intake regimen closely (for example, to facilitate prevention of opioid overdose). In such cases, rehab centers may provide devices on a temporary basis to the patients and regulate as well as monitor their drug usage. A similar business model as in the case of hospitals (2.*a*) may exist to fulfill the business relationship in this model.

Further, home healthcare facilities may use the disclosed software and devices to provide differentiated services. For example, home healthcare services companies can use connected medication dispensers and systems disclosed herein to ensure patient medication compliance.

For a higher degree of accuracy in clinical studies, understanding the subject patients' adherence as well as nudging them to taking the required medicine is critical. The connected medication dispensers and systems disclosed herein can be used for such studies, along with target software specifications to remotely manage patients and doses required for clinical studies use cases.

B2C Direct/Indirect

Direct sell to patients or caregivers (patient or caregiver pays): This is an existing model where the patients and/or caregiver purchases the device, software seats and support service directly. To compete in the marketplace, the device features and services may be customized and differentiated to create compelling value-add for the consumers.

Indirect sell to patients or caregivers via pharmacies, physician's offices etc. (patient or caregiver pays): In this model, the patients or the caregivers can purchase the device, software seats and associated support services indirectly from their pharmacies or physicians.

In the Summary above and in this Detailed Description, and the Claims below, and in the accompanying drawings, reference is made to features of various embodiments of the invention. It is to be understood that the disclosure of embodiments of the invention in this specification is intended to be interpreted as including all possible combinations of such features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted to not unnecessarily obscure the embodiments.

In the present disclosure, various features may be described as being optional, for example, through the use of the verb "may;" or, through the use of any of the phrases: "in some embodiments," "in some implementations," "in some designs," "in various embodiments," "in various implementations," "in various designs," "in an illustrative example," or "for example," or through the use of parentheses. For the sake of brevity and legibility, the present disclosure does not explicitly recite every permutation that may be obtained by choosing from the set of optional features. However, the present disclosure is to be interpreted as explicitly disclosing all such permutations. For example, a system described as having three optional features may be embodied in seven separate ways, namely with just one of the three possible features, with any two of the three possible features or with all three of the three possible features.

In various embodiments, elements described herein as coupled or connected may have an effectual relationship realizable by a direct connection or indirectly with one or more other intervening elements.

In the present disclosure, the term "any" may be understood as designating any number of the respective elements, that is, as designating one, at least one, at least two, each or all of the respective elements. Similarly, the term "any" may be understood as designating any collection(s) of the respective elements, that is, as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation, and form of the invention without departing from the spirit and scope thereof. It is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

In the present disclosure, all embodiments where "comprising" is used may have as alternatives "consisting essentially of," or "consisting of" In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises," and grammatical equivalents thereof are used herein to mean that other components, ingredients, steps, among others, are optionally present. For example, an embodiment "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)–(a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112(f). Specifically, any use of "step of" in the claims herein is not intended to invoke the provisions of 35 U.S.C. § 112(f). Elements recited in means-plus-function format are intended to be construed in accordance with 35 U.S.C. § 112(f).

Recitation in a claim of the term "first" with respect to a feature or element does not necessarily imply the existence of a second or additional such feature or element.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects may lie in a combination of fewer than all features of any single foregoing disclosed embodiment. Thus, the claims following this Detailed Description are hereby expressly incorporated into this Detailed Description, with each claim standing on its own as a separate embodiment. This disclosure is intended to be interpreted as including all permutations of the independent claims with their dependent claims.

According to an embodiment of the present invention, the system and method may be accomplished using one or more computing devices. As depicted, for example, at least in FIGS. 1-6 and 13, one of ordinary skill in the art would appreciate that an exemplary system appropriate for use with embodiments in accordance with the present application may generally include one or more of a Central processing Unit (CPU), Random Access Memory (RAM), a storage medium (e.g., hard disk drive, solid state drive, flash memory, cloud storage), an operating system (OS), one or more application software, a display element, one or more communications means, or one or more input/output devices/means. Examples of computing devices usable with embodiments of the present invention include, but are not limited to, proprietary computing devices, personal computers, mobile computing devices, tablet PCs, mini-PCs, servers, or any combination thereof. The term computing device may also describe two or more computing devices communicatively linked in a manner as to distribute and share one or more resources, such as clustered computing devices and server banks/farms. One of ordinary skill in the art would understand that any number of computing devices could be used, and embodiments of the present invention are contemplated for use with any computing device.

In various embodiments, communications means, data store(s), processor(s), or memory may interact with other components on the computing device, to affect the provisioning and display of various functionalities associated with the system and method detailed herein. One of ordinary skill in the art would appreciate that there are numerous configurations that could be utilized with embodiments of the present invention, and embodiments of the present invention are contemplated for use with any appropriate configuration.

According to an embodiment of the present invention, the communications means of the system may be, for instance, any means for communicating data over one or more networks or to one or more peripheral devices attached to the system. Appropriate communications means may include, but are not limited to, circuitry and control systems for providing wireless connections, wired connections, cellular connections, data port connections, Bluetooth connections, or any combination thereof. One of ordinary skill in the art would appreciate that there are numerous communications means that may be utilized with embodiments of the present invention, and embodiments of the present invention are contemplated for use with any communications means.

Throughout this disclosure and elsewhere, block diagrams and flowchart illustrations depict methods, apparatuses (that is, systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions; by combinations of general-purpose hardware and computer instructions; and so on—any and all of which may be generally referred to herein as a "circuit," "module," or "system."

While the foregoing drawings and description may set forth functional aspects of the disclosed systems, no particular arrangement of software for implementing these functional aspects should be inferred from these descriptions unless explicitly stated or otherwise clear from the context.

Each element in flowchart illustrations may depict a step, or group of steps, of a computer-implemented method. Further, each step may contain one or more sub-steps. For the purpose of illustration, these steps (as well as any and all other steps identified and described above) are presented in order. It will be understood that an embodiment can contain an alternate order of the steps adapted to a particular application of a technique disclosed herein. All such variations and modifications are intended to fall within the scope of this disclosure. The depiction and description of steps in any particular order is not intended to exclude embodiments having the steps in a different order, unless required by a particular application, explicitly stated, or otherwise clear from the context.

Traditionally, a computer program consists of a sequence of computational instructions or program instructions. It will be appreciated that a programmable apparatus (that is, computing device) can receive such a computer program and, by processing the computational instructions thereof, produce a further technical effect.

A programmable apparatus may include one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this disclosure and elsewhere a computer can include any and all suitable combinations of at least one general purpose computer, special-purpose computer, programmable data processing apparatus, processor, processor architecture, and so on.

It will be understood that a computer can include a computer-readable storage medium and that this medium may be internal or external, removable and replaceable, or fixed. It will also be understood that a computer can include a Basic Input/Output System (BIOS), firmware, an operating system, a database, or the like that can include, interface with, or support the software and hardware described herein.

Embodiments of the system as described herein are not limited to applications involving conventional computer programs or programmable apparatuses that run them. It is contemplated, for example, that embodiments of the invention as claimed herein could include an optical computer, quantum computer, analog computer, or the like.

Regardless of the type of computer program or computer involved, a computer program can be loaded onto a computer to produce a particular machine that can perform any and all of the depicted functions. This particular machine provides a means for carrying out any and all of the depicted functions.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Computer program instructions can be stored in a computer-readable memory capable of directing a computer or other programmable data processing apparatus to function in a particular manner. The instructions stored in the computer-readable memory constitute an article of manufacture including computer-readable instructions for implementing any and all of the depicted functions.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

The elements depicted in flowchart illustrations and block diagrams throughout the figures imply logical boundaries between the elements. However, according to software or hardware engineering practices, the depicted elements and the functions thereof may be implemented as parts of a monolithic software structure, as standalone software modules, or as modules that employ external routines, code, services, and so forth, or any combination of these. All such implementations are within the scope of the present disclosure.

Unless explicitly stated or otherwise clear from the context, the verbs “execute” and “process” are used interchangeably to indicate execute, process, interpret, compile, assemble, link, load, any and all combinations of the foregoing, or the like. Therefore, embodiments that execute or process computer program instructions, computer-executable code, or the like can suitably act upon the instructions or code in any and all of the ways just described.

The functions and operations presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will be apparent to those of skill in the art, along with equivalent variations. In addition, embodiments of the invention are not described with reference to any particular programming language.

It is appreciated that a variety of programming languages may be used to implement the present teachings as described herein, and any references to specific languages are provided for disclosure of enablement and best mode of embodiments of the invention. Embodiments of the invention are well suited to a wide variety of computer network systems over numerous topologies. Within this field, the configuration and management of large networks include storage devices and computers that are communicatively coupled to dissimilar computers and storage devices over a network, such as the Internet.

Several implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A system for dispensing medicine to a patient, the system comprising:

a medicine dispenser having an outer housing comprising:

a processor, a memory operably coupled with the processor, wherein the memory encodes processor executable program instructions and data to program and configure the processor to control the medicine dispenser, a network interface configured to provide wired or wireless communication between the processor and a data network, a carousel supported horizontally on a central shaft that includes a carousel motor to provide 360-degree rotation of the carousel in either direction, a plurality of bins supported in respective openings in the carousel, wherein the plurality of bins comprise object bins and a dispense bin, wherein the dispense bin comprises a spring mounted door having a follower tab, a fixed cam located above the carousel at a delivery position, wherein, upon rotation of the carousel to position the dispense bin at the delivery position, the follower tab on the dispense bin interferes with the fixed cam to force the spring mounted door on the dispense bin to open so that medications contained therein may fall into a dispensing chute, a robotic arm having a suction gripper, wherein the robotic arm is configured to move vertically to extend and retract the suction gripper into one of the object bins to grip a medication via the suction gripper, wherein the carousel is configured to rotate to position the dispense bin below the robotic arm so that the medication can be released from the suction gripper into the dispense bin; and a software program product configured to communicate via the data network with one or more of a pharmacy server of a pharmacy, a physician server of a prescribing physician of the patient, a caregiver device, patient selected third parties, and a user device of the patient, wherein the software program product is configured to:

control the medicine dispenser with at least one of the pharmacy server and the physician server to deliver a dose to the patient based on a prescription data, wherein the dose is delivered upon authentication of an authorized user, wherein the authorized user is selected from the patient or an authorized caregiver.

2. The system of claim 1, wherein the medicine dispenser comprises a weighing station positioned below the carousel and configured to weight each of the object bins, wherein the weighing station comprises:

a linear actuator configured for vertical movement, and a load cell position on a top portion of the linear actuator and communicatively coupled to the processor and the memory, wherein the weighing station weights each of the object bins by (i) moving the load cell to a position under the object bin by vertical upward movement of the linear actuator so that a full weight of the object bin rests on the load cell, wherein the load cell registers the full weight of the object bin and communicates the full weight of the object bin to the processor, and (ii) moving the load cell to a position beneath the carousel and separated from the object bin by vertical movement downward of the linear actuator.

3. The system of claim 2, wherein the weighting station includes a bin platform attached to a top of the load cell, wherein the bin platform is sized and shaped to stably receive the object bin thereon when the linear actuator moves vertically upward to the position under the object bin and lifts the object bin so that at least a top rim of the object bin is separated from and positioned above a bin support frame of the carousel.

4. The system of claim 3, wherein the object bins include a recess on opposing sides below a top opening thereof, wherein the recesses are engageable with respective axially extending arms of the bin support frame and are configured to allow vertical movement of the object bin when lifted on the bin support frame without removal of the object bin from the bin support frame.

5. The system of claim 2, wherein the medicine dispenser is configured to weigh each of the object bins (i) before loading to provide a tare weight of the object bin, (ii) after loading with medications to provide a total bin starting weight and calculated average medication weight, and (iii) after gripping the medication to provide verification of a successful pick and an updated bin weight, wherein each of the tare weight, total bin starting weight, calculated average medication weight, and updated bin weight are stored to the memory.

6. The system of claim 5, wherein, if the updated bin weight of the object bin changes by less than 70% or by more than 130% of the calculated average medication weight from a previously registered weight of the object bin, the medicine dispenser registers a failed pick attempt and is configured to repeat the attempt to grip the medication.

7. The system of claim 6, wherein, after one or more failed pick attempts, the robotic arm moves vertically upward and the carousel shakes to rearrange the medications in the object bins, and the robotic arm repeats the attempt to grip the medication.

8. The system of claim 6, wherein, after one or more failed pick attempts, the rack and pinion arrangement of the robotic arm moves the spring mounted probe horizontally within the object bin and the robotic arm repeats the attempt to grip the medication.

9. The system of claim 2, wherein the robotic arm is positioned above the carousel and vertically coincident with the weighting station positioned below the carousel.

10. The system of claim 1, wherein the fixed cam is attached to a distal end of an arm extending radially from the central shaft of the carousel.

11. The system of claim 1, wherein, when the dose comprises a plurality of medications, the carousel does not rotate to place the dispense bin at the delivery position until the dispense bin contains the plurality of medications.

12. The system of claim 1, wherein the carousel rotates bi-directionally to position a selected object bin containing a medication to be gripped at a start position below the robotic arm, and when the dose comprises a plurality of medications, the carousel does not rotate to place the dispense bin at the delivery position until the dispense bin contains the plurality of medications.

13. The system of claim 1, comprising a medication collecting cup positioned below the dispensing chute, wherein the medication collecting cup is positioned on a limit switch to indicate presence or absence of the medication collecting cup, and wherein the carousel will not rotate to position the dispense bin at the delivery location unless the medication collecting cup is present.

14. The system of claim 1, wherein the medicine dispenser comprises an absolute encoder configured to measure a degree of rotation of the carousel to ensure positional accuracy of the carousel when rotated to position one of the plurality of bins at a start position below the robotic arm.

15. The system of claim 1, wherein the outer housing of the medicine dispenser is conical and includes an angled top surface comprising a display screen, wherein the angle of the top surface is 10°-45° relative to a horizontal plane of a floor surface.

16. The system of claim 1, wherein the robotic arm comprises:

a central beam positioned adjacent an outer edge of the carousel, a spring mounted probe attached to the central beam via a rack and pinion arrangement, wherein the rack and pinion arrangement provides transverse movement of the flexible probe, wherein a top portion of the flexible probe is attached to the rack and pinion arrangement, and an actuator positioned at a base of the central beam and configured to move the rack and pinion arrangement vertically along the central beam, wherein the suction gripper is attached to a bottom end of the spring mounted probe.

17. The system of claim 16, wherein the suction gripper of the robotic arm is a vacuum suction gripper including a tube-shaped rubber skirt, and wherein the spring mounted probe comprises a spring configured to allow flexible motion of the suction gripper and tube-shaped rubber skirt in the x, y, and z directions.

18. The system of claim 17, wherein the medicine dispenser includes a vacuum pump connected via conduit to the suction gripper.

19. The system of claim 1, comprising:

an image sensor, wherein the image sensor is configured to capture images of patient medication consumption activity, wherein the captured images are analyzed by the medicine dispenser to identify images that correlate with image data representative of various patient activity states associated with medication adherence, wherein the captured images are time stamped based on time of capture to validate timing of medication adherence, and wherein the software program product is configured to, in response to determining a lack of medication adherence, send a notification of the lack of medication adherence to one or more of the pharmacy server, the physician server, the caregiver device, the user device of the patient, and patient selected third parties.

20. The system of claim 19, comprising:

a biometric sensor, wherein authentication of the authorized user is via the image sensor, the biometric sensor, or both of the image sensor and the biometric sensor.

21. The system of claim 1, wherein the software program product is configured to:

communicate with one or more patient sensors operably couplable with the processor to sense and communicate patient data associated with the patient, transfer the patient data sensed and communicated by the one or more patient sensors to at least one of the pharmacy server and the physician server, and update the prescription data based on the patient data.

22. The system of claim 21, wherein one of the one or more patient sensors is a physiological sensor, and the software program product is configured to determine a patient condition as a function of the patient data acquired from the one or more patient sensor, and wherein the software program product is configurable to initiate audio communication, video communication, or both between the physician server and the user device when the patient data indicates that the patient missed the dose, the patient is experiencing a health crisis, a new dose or dose administration time is recommended, or any combination thereof.

23. The system of claim 22, wherein the physiological sensor is a blood-pressure sensor, blood sugar sensor, blood oxygen level sensor, heart rate sensor, temperature sensor, weight sensor, electrocardiogram, or combination thereof.

24. The system of claim 21, wherein the software program product is configured to adjust the dose in response to input received from the one or more patient sensors, wherein the dose is adjusted in real-time and delivered to the patient from the medicine dispenser immediately or upon a next schedule dose.

25. The system of claim 1, wherein the software program product is configured to;

acquire sensor data associated with the patient using one or more patient sensors operably coupled with the medicine dispenser;

generate predictive analytic output representative of a patient outcome based on the sensor data using an artificial intelligence model;

transmit the predictive analytic output to a healthcare professional; and adjust the dose in response to input received from the healthcare professional, wherein the adjustment is made by the healthcare professional in response to the predictive analytic output, and wherein the dose is adjusted in real-time and delivered to the patient from the medicine dispenser immediately or upon a next scheduled dose.

26. The system of claim 1, wherein the medicine dispenser is linked to an electronic health record of the patient, and medication compliance data collected by the medicine dispenser is shared to the electronic health record of the patient.

* * * * *